(12) United States Patent
Haecker et al.

(10) Patent No.: US 12,270,806 B2
(45) Date of Patent: *Apr. 8, 2025

(54) RAPID ASSAY FOR DETECTION OF SARS-CoV-2 ANTIBODIES

(71) Applicant: UNIVERSITY OF UTAH RESEARCH FOUNDATION, Salt Lake City, UT (US)

(72) Inventors: Hans Haecker, Salt Lake City, UT (US); Vanessa Redecke, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 352 days.

This patent is subject to a terminal disclaimer.

(21) Appl. No.: 17/862,666

(22) Filed: Jul. 12, 2022

(65) Prior Publication Data

US 2023/0025108 A1 Jan. 26, 2023

Related U.S. Application Data

(60) Continuation of application No. 17/478,527, filed on Sep. 17, 2021, now Pat. No. 11,467,165, which is a division of application No. 17/140,321, filed on Jan. 4, 2021, now Pat. No. 11,175,293.

(51) Int. Cl.
| | |
|---|---|
| *C07K 14/165* | (2006.01) |
| *C07K 14/47* | (2006.01) |
| *C07K 16/10* | (2006.01) |
| *C07K 16/30* | (2006.01) |
| *G01N 33/49* | (2006.01) |
| *G01N 33/68* | (2006.01) |

(52) U.S. Cl.
CPC .......... *G01N 33/49* (2013.01); *C07K 14/165* (2013.01); *C07K 14/47* (2013.01); *C07K 16/1003* (2023.08); *C07K 16/3061* (2013.01); *G01N 33/68* (2013.01); *C07K 2319/02* (2013.01); *C07K 2319/30* (2013.01); *C07K 2319/73* (2013.01)

(58) Field of Classification Search
None
See application file for complete search history.

(56) References Cited

U.S. PATENT DOCUMENTS

| | | |
|---|---|---|
| 9,879,090 B2 | 1/2018 | Bertrand et al. |
| 2007/0042350 A1 | 2/2007 | Li et al. |
| 2007/0053878 A1 | 3/2007 | Haagmans et al. |
| 2007/0248616 A1 | 10/2007 | Brownlie et al. |
| 2009/0029924 A1 | 1/2009 | Strongin et al. |
| 2012/0258126 A1 | 10/2012 | Scholler et al. |
| 2014/0120113 A1 | 5/2014 | Kwaks et al. |
| 2015/0110826 A1 | 4/2015 | Bayne et al. |

| | | |
|---|---|---|
| 2017/0269101 A1 | 9/2017 | Yerramilli et al. |
| 2017/0356921 A1 | 12/2017 | Van Roosmalen et al. |
| 2018/0292408 A1 | 10/2018 | Qi |
| 2020/0040042 A1 | 2/2020 | Chappell et al. |

FOREIGN PATENT DOCUMENTS

| | | |
|---|---|---|
| AU | 4876399 A | 11/1999 |
| CN | 108463229 A | 8/2018 |
| CN | 108778308 A | 11/2018 |
| CN | 109503711 A | 3/2019 |
| KR | 20180118175 A | 10/2018 |
| WO | 2007053165 A2 | 5/2007 |
| WO | 2017068352 A1 | 4/2017 |
| WO | 2017070364 A1 | 8/2018 |
| WO | 2019217967 A1 | 11/2019 |
| WO | 2020099922 A1 | 5/2020 |
| WO | 2020163721 A1 | 8/2020 |
| WO | 2021222772 A2 | 11/2021 |

OTHER PUBLICATIONS

Dutta et al., "Search for potential target site of nucleocapsid gene for the design of an epitope-based SARS DNA vaccine," Immunol. Let., vol. 118, 2008, pp. 65-71.
Dutta et al., "The Nucleocapsid Protein of SARS-CoV-2: a Target for Vaccine Development," J. Virol., vol. 94, No. 13, 2020, pp. e00647-20.
Grant et al., "Analysis of the SARS-CoV-2 spike protein glycan shield reveals implications for immune recognition," Sci. Rep., vol. 10, 2020, 12 pages.
Grzelak et al., "A comparison of four serological assays for detecting anti-SARS-CoV-2 antibodies in human serum samples from different populations," Sci. Transl. Med., vol. 12, 2020, eabc3103, 15 pages.
Gudbjartsson et al., "Humoral Immune Response to SARS-CoV-2 in Iceland," N. Engl. J. Med., vol. 383, No. 18, 2020, pp. 1724-1734.
Gupta et al., "Expression, purification, and characterization of an anti-RBCFab-p24 fusion protein for hemagglutination-based rapid detection of antibodies to HIV in whole blood," Protein Expr. Purif., vol. 26, 2002, pp. 162-170.
Gupta et al., "Whole-blood agglutination assay for on-site detection of human immunodeficiency virus infection," J. Clin. Microbiol., vol. 41, No. 7, 2003, pp. 2814-2821.
Habib et al., "V(H)H (nanobody) directed against human glycophorin A: a tool for autologous red cell agglutination assays," Anal. Biochem., vol. 438, 2013, pp. 82-89.
Hachim et al., "ORF8 and ORF3b antibodies are accurate serological markers of early and late SARS-CoV-2 infection," Nat. Immunol., vol. 21,, 2020, pp. 1293-1301.

(Continued)

*Primary Examiner* — Michael D Burkhart
(74) *Attorney, Agent, or Firm* — Michael Best & Friedrich LLP

(57) ABSTRACT

Described herein are diagnostic and control fusion protein reagents and methods for use thereof in simple rapid and inexpensive hemagglutinin assays for the detection of subject antibodies directed to the SARS-CoV-2 virus.

19 Claims, 8 Drawing Sheets

Specification includes a Sequence Listing.

(56) References Cited

OTHER PUBLICATIONS

Huo et al., "Neutralizing nanobodies bind SARS-CoV-2 spike RBD and block interaction with ACE2", Nature Structural & Molecular Biology, vol. 27, 2020, pp. 846-854.
Kemp et al., "Autologous red cell agglutination assay for HIV-1 antibodies: simplified test with whole blood," Science, vol. 241, 1988, pp. 1352-1354.
Kontou et al., "Antibody Tests in Detecting SARS-CoV-2 Infection: A Meta-Analysis," Diagnostics, vol. 10, No. 319, 2020, 15 pages.
Lee et al., "Detection of antibodies against SARS-Coronavirus using recombinant truncated nucleocapsid proteins by Elisa," J. Microbiol. Biotechnol., vol. 18, No. 10, 2008, pp. 1717-1721.
Lee et al., "Production of specific antibodies against SARS-coronavirus nucleocapsid protein without cross reactivity with human coronaviruses 229E and OC43," J. Vet. Sci., vol. 11, No. 2, 2010, pp. 165-167.
Okba et al., "Serologic Detection of Middle East Respiratory Syndrome Coronavirus Functional Antibodies", Emerging Infectious Dis, vol. 26, No. 5, 2020, pp. 1024-1027.
Ravichandran et al., "Antibody signature induced by SARS-COV-2 spike protein immunogens in rabbits," Sci. Transl. Med., vol. 12, 2002, eabc3539, 7 pages.
Redecke et al., "Hematopoietic progenitor cell lines with myeloid and lymphoid potential," Nat. Methods, vol. 10, No. 8, 2013, pp. 795-803.
Sah et al., "Complete Genome Sequence of a 2019 Novel Coronavirus (SARS-CoV-2) Strain Isolated in Nepal", American Society for Microbiology, vol. 9, Issue 11, 2020, 3 pages.
Salvatori et al., "SARS-CoV-2 Spike Protein: an optimal immunological target for vaccines," J. Transl. Med., vol. 18, No. 222, 2020, 3 pages.
Tai et al., "Characterization of the receptor-binding domain (RBD) of 2019 novel coronavirus: implication for development of RBD protein as a viral attachment inhibitor and vaccine," Cell. Mol. Immunol., vol. 17, No. 6, 2020, pp. 613-620.
Tillib et al., "Formatted single-domain antibodies can protect mice against infection with influenza virus (H5N2)", Antiviral Research, vol. 97, 2013, pp. 245-254.
Townsend et al., "A haemagglutination test for rapid detection of antibodies to SARS-CoV-2", Nature Communications, Mar. 2021, pp. 1-6.
Kruse et al., "A rapid, point of care red blood cell agglutination assay for detecting antibodies against SARS-Cov-2," bioRxiv preprint doi: https://doi.org/10.1101/2020.05.13.094490; May 14, 2020.
Kruse et al., "A rapid, point-of-care red blood cell agglutination assay detecting antibodies against SARS-CoV-2," Biochem Biophys Res Commun. 553: 165-171 (May 14, 2021) doi: 10.1016/j.bbrc.2021.03.016. Epub Mar. 15, 2021.
Esmail et al., "Rapid and accurate point-of-care testing for SARS-CoV2 antibodies," medRxiv preprint doi: https://doi.org/10.1101/2020.11.30.20241208; Dec. 2, 2020.
Esmail et al, "Rapid and accurate agglutination-based testing for SARS-CoV-2 antibodies," Cell Reports Methods 1, 100011, Jun. 21, 2021 https://doi.org/10.1016/j.crmeth.2021.100011.

```
                          SEQUENCE LISTING

Sequence total quantity: 67
SEQ ID NO: 1            moltype = DNA  length = 1260
FEATURE                 Location/Qualifiers
misc_feature            1..1260
                        note = Synthetic
source                  1..1260
                        mol_type = other DNA
                        organism = synthetic construct
SEQUENCE: 1
atgaccaaca agtgcctgct gcagattgcc ctgctgctgt gcttcagcac aacagccctg   60
tctatgggcg cgcctcaagt tcagcttcaa gaatctggcg gcggaagcgt tcaggctggc  120
ggatctctga gactgagctg tgtggccagc ggctacaccg atagcacata ctgcgtcggc  180
tggttcagac aggcccctgg caaagagaga gagggcgtcg ccagaatcaa caccatcagc  240
ggcagacctt ggtacgccga ctctgtgaag ggcagattca caatcagcca ggacaacagc  300
aagaacaccg tgtacctgca gatgaacagc ctgaagcctg aggacaccgc catctactac  360
tgcacccctga ccaccgccaa cagcagaggc ttttgttccg gcggctacaa ctacaaaggc  420
cagggcaccc aagtgaccgt gtctggtggt accagcggag gcggaggatc aggtggcgga  480
ggtagtggtg gtggcggtag cgcggccgct agattcccca acatcaccaa tctgtgcccc  540
ttcggcgagg tgttcaacgc cacaagattc gcctctgtgt acgcctggaa ccggaagcgg  600
atcagcaatt gcgtggccga ctacagcgtg ctgtacaaca gcgccagctt ctccaccttc  660
aagtgctacg gcgtgtcccc taccaagctg aacgacctgt gctttaccaa cgtgtacgcc  720
gatagcttcg tgatccgggg agatgaagtg cggcagatcg ctcctggaca gacaggcaag  780
atcgccgact ataactacaa gctgcccgac gacttcaccg gctgtgtgat tgcctggaac  840
agcaacaacc tggacagcaa agtcggcggc aactacaatt acctgtaccg gctgttccgg  900
aagtccaatc tgaagccctt cgagcgggac atcagcaccg agatctatca ggccggcagc  960
accccttgca atggcgtgga aggcttcaac tgctacttcc cactgcagtc ctacggcttc 1020
cagcctacaa acggcgtggg ctaccagcct tacagagtgg tggtcctgag cttcgagctg 1080
ctgcatgccc ctgctacagt gtgcggccct aagaagtcta ccaacctgga attcggcgga 1140
ggcagcggcg gtggaagcgg cggaggctct gcttggagcc acccgcagtt cgaaaaaggt 1200
ggaggttctg gcggtggatc gggaggttca gcgtggagcc acccgcagtt cgagaaatga 1260

SEQ ID NO: 2            moltype = AA  length = 419
FEATURE                 Location/Qualifiers
REGION                  1..419
                        note = Synthetic Construct
source                  1..419
                        mol_type = protein
                        organism = synthetic construct
SEQUENCE: 2
MTNKCLLQIA LLLCFSTTAL SMGAPQVQLQ ESGGGSVQAG GSLRLSCVAS GYTDSTYCVG   60
WFRQAPGKER EGVARINTIS GRPWYADSVK GRFTISQDNS KNTVYLQMNS LKPEDTAIYY  120
CTLTTANSRG FCSGGYNYKG QGTQVTVSGG TSGGGGSGGG GSGGGGSAAA RFPNITNLCP  180
FGEVFNATRF ASVYAWNRKR ISNCVADYSV LYNSASFSTF KCYGVSPTKL NDLCFTNVYA  240
DSFVIRGDEV RQIAPGQTGK IADYNYKLPD DFTGCVIAWN SNNLDSKVGG NYNYLYRLFR  300
KSNLKPFERD ISTEIYQAGS TPCNGVEGFN CYFPLQSYGF QPTNGVGYQP YRVVVLSFEL  360
LHAPATVCGP KKSTNLEFGG GSGGGSGGGS AWSHPQFEKG GGSGGGSGGS AWSHPQFEK   419

SEQ ID NO: 3            moltype = DNA  length = 1899
FEATURE                 Location/Qualifiers
misc_feature            1..1899
                        note = Synthetic
source                  1..1899
                        mol_type = other DNA
                        organism = synthetic construct
SEQUENCE: 3
atgaccaaca agtgcctgct gcagattgcc ctgctgctgt gcttcagcac aacagccctg   60
tctatgggcg cgcctcaagt tcagcttcaa gaatctggcg gcggaagcgt tcaggctggc  120
```

```
ggatctctga gactgagctg tgtggccagc ggctacaccg atagcacata ctgcgtcggc    180
tggttcagac aggcccctgg caaagagaga gagggcgtcg ccagaatcaa caccatcagc    240
ggcagacctt ggtacgccga ctctgtgaag gcagattca caatcagcca ggacaacagc    300
aagaacaccg tgtacctgca gatgaacagc ctgaagcctg aggacaccgc catctactac    360
tgcaccctga ccaccgccaa cagcagaggc ttttgttccg gcggctacaa ctacaaaggc    420
cagggcaccc aagtgaccgt gtctggtggt accagcggag gcggaggatc aggtggcgga    480
ggtagtggtg gtggcggtag cgcggccgcc atgtctgata acggccctca gaaccagcgg    540
aacgccccta gaatcacatt tggcggccct agcgatagca ccggcagcaa tcagaatggc    600
gagagaagcg gcgccagaag caagcagaga aggcctcaag gcctgcctaa caacaccgcc    660
agctggttca cagccctgac acagcacggc aaagaggacc tgaagttccc cagaggacag    720
ggcgtgccca tcaacacaaa cagcagcccc gatgaccaga tcggctacta cagacgggcc    780
accagaagaa tcagaggcgg cgacggcaag atgaaggatc tgagcccag atggtacttc    840
tactacctcg gcacaggacc cgaagccgga cttccttatg gcgccaacaa ggacggcatc    900
atctgggttg caaccgaagg cgccctgaac accctcagg accacatcgg caccagaaat    960
cccgccaaca atgccgccat tgtgctgcag ttgcctcagg gcacaacact gcccaagggc   1020
ttttacgccg agggcagcag aggcggaagc caggcctcta gcagaagctc cagcagaagc   1080
cggaactcca gccggaatag cacacctgga agcagcaggg gcacaagccc tgctagaatg   1140
gctgccaatg gcggagatgc tgctctggcc ctgttgctgc tggaccggct gaatcagctg   1200
gaaagcaaga tgagcggcaa gggccagcaa cagcaggc gagaccgtgac caaaaagtct   1260
gccgccgagg ccagcaagaa gcccagacag aaaagaaccg ccaccaaggc ctacaacgtg   1320
acccaggcct ttggaagaag aggccctgag cagacccagg caacttcgg agatcaagag   1380
ctgatcagac agggcaccga ctacaagcac tggcctcagt tgcccagtt tgcccccatct   1440
gccagcgcct ttttcggcat gagccggatc ggcatggaag tgacacctag cggcacctg   1500
ctgacataca caggcgccat caagctggac gacaaggacc caacttcaa ggaccaagtg    1560
atcctgctga caagcacat cgacgcctac aagacattcc ctccaaccga gcctaagaag   1620
gacaagaaga agaaggccga cgagacacag gccctgcctc agcgccagaa aaagcagcag   1680
acagtgacac tgctgccagc cgccgacctg gacgattttt ctaagcagct gcagcagtcc   1740
atgagcagcg ccgattctac ccaggccgaa ttcggcggag gttcaggcgg tggaagtggt   1800
ggtggatctg cttggagcca tcctcagttc gagaaaggcg gtggtagcgg cggaggaagc   1860
ggtggctcag cttggtcaca cccacagttt gagaagtga                          1899

SEQ ID NO: 4               moltype = AA   length = 632
FEATURE                    Location/Qualifiers
REGION                     1..632
                           note = Synthetic Construct
source                     1..632
                           mol_type = protein
                           organism = synthetic construct
SEQUENCE: 4
MTNKCLLQIA LLLCFSTTAL SMGAPQVQLQ ESGGGSVQAG GSLRLSCVAS GYTDSTYCVG     60
WFRQAPGKER EGVARINTIS GRPWYADSVK GRFTISQDNS KNTVYLQMNS LKPEDTAIYY    120
CTLTTANSRG FCSGGYNYKG QGTQVTVSGG TSGGGGSGGG GSGGGGSAAA MSDNGPQNQR    180
NAPRITFGGP SDSTGSNQNG ERSGARSKQR RPQGLPNNTA SWFTALTQHG KEDLKFPRGQ    240
GVPINTNSSP DDQIGYYRRA TRRIRGGDGK MKDLSPRWYF YYLGTGPEAG LPYGANKDGI    300
IWVATEGALN TPKDHIGTRN PANNAAIVLQ LPQGTTLPKG FYAEGSRGGS QASSRSSSRS    360
RNSSRNSTPG SSRGTSPARM AGNGGDAALA LLLLDRLNQL ESKMSGKGQQ QQGQTVTKKS    420
AAEASKKPRQ KRTATKAYNV TQAFGRRGPE QTQGNFGDQE LIRQGTDYKH WPQIAQFAPS    480
ASAFFGMSRI GMEVTPSGTW LTYTGAIKLD DKDPNFKDQV ILLNKHIDAY KTFPPTEPKK    540
DKKKKADETQ ALPQRQKKQQ TVTLLPAADL DDFSKQLQQS MSSADSTQAE FGGGSGGGSG    600
GGSAWSHPQF EKGGGSGGGS GGSAWSHPQF EK                                  632

SEQ ID NO: 5               moltype = DNA   length = 954
FEATURE                    Location/Qualifiers
misc_feature               1..954
                           note = Synthetic
source                     1..954
                           mol_type = other DNA
                           organism = synthetic construct
SEQUENCE: 5
atgaccaaca gtgcctgct gcagattgcc ctgctgctgt gcttcagcac aacagccctg     60
tctatgggcg cgcctcaagt tcagcttcaa gaatctggcg gcggaagcgt tcaggctggc    120
ggatctctga gactgagctg tgtggccagc ggctacaccg atagcacata ctgcgtcggc    180
tggttcagac aggcccctgg caaagagaga gagggcgtcg ccagaatcaa caccatcagc    240
ggcagacctt ggtacgccga ctctgtgaag gcagattca caatcagcca ggacaacagc    300
aagaacaccg tgtacctgca gatgaacagc ctgaagcctg aggacaccgc catctactac    360
tgcaccctga ccaccgccaa cagcagaggc ttttgttccg gcggctacaa ctacaaaggc    420
cagggcaccc aagtgaccgt gtctggtggt accagcggag gcggaggatc aggtggcgga    480
ggtagtggtg gtggcggtag cgcggccgcc aagaatgta gcctgcagag ctgcacacag    540
caccagcctt acgtggtgga cgaccctgt ctatccact tctacagca gttgtacatc     600
agagtgggcg ccagaaagag cgccccactg attgagctgt gtgtggatga ggccggcagc    660
aagagcccca tccagtacat cgacatcggc aactacaccg tgtcctgcct gccttttcacc    720
atcaactgcc aagagcctaa gctgggctct ctggtcgtgc ggtgcagctt ctacgaggac    780
ttcctggaat accacgacgt gcgcgtggtg ctggatttca tcccgcgggg tgtggtagt    840
ggcggaggaa gtggtggcgg atctgcttgg agccatcctc agttcgagaa aggcggcggt    900
tcaggtggtg gatcaggcgg ttctgcatgg tcacacccac agtttgagaa gtga          954

SEQ ID NO: 6               moltype = AA   length = 317
FEATURE                    Location/Qualifiers
REGION                     1..317
```

```
                        note = Synthetic Construct
source                  1..317
                        mol_type = protein
                        organism = synthetic construct
SEQUENCE: 6
MTNKCLLQIA LLLCFSTTAL SMGAPQVQLQ ESGGGSVQAG GSLRLSCVAS GYTDSTYCVG   60
WFRQAPGKER EGVARINTIS GRPWYADSVK GRFTISQDNS KNTVYLQMNS LKPEDTAIYY  120
CTLTTANSRG FCSGGYNYKG QGTQVTVSGG TSGGGGSGGG GSGGGGSAAA QECSLQSCTQ  180
HQPYVVDDPC PIHFYSKWYI RVGARKSAPL IELCVDEAGS KSPIQYIDIG NYTVSCLPFT  240
INCQEPKLGS LVVRCSFYED FLEYHDVRVV LDFIPRGGGS GGGSGGGSAW SHPQFEKGGG  300
SGGGSGGSAW SHPQFEK                                                 317

SEQ ID NO: 7            moltype = DNA  length = 1635
FEATURE                 Location/Qualifiers
misc_feature            1..1635
                        note = Synthetic
source                  1..1635
                        mol_type = other DNA
                        organism = synthetic construct
SEQUENCE: 7
atgaccaaca agtgcctgct gcagattgcc ctgctgctgt gcttcagcac aacagccctg   60
tctatgggcg cgcctcaagt tcagcttcaa gaatctggcg gcggaagcgt tcaggctggc  120
ggatctctga gactgagctg tgtggccagc ggctacaccg atagcacata ctgcgtcggc  180
tggttcagac aggcccctgg caaagagaga gagggcgtcg ccagaatcaa caccatcagc  240
ggcagacctt ggtacgccga ctctgtgaag ggcagattca atcagcca ggacaacagc    300
aagaacaccg tgtacctgca gatgaacagc ctgaagcctg aggacaccgc catctactac  360
tgcacccctga ccaccgccaa cagcagaggc ttttgttccg gcggctacaa ctacaaaggc  420
cagggcaccc aagtgaccgt gtctggtggt accagcggag gcggaggatc aggtggcgga  480
ggtagtggtg gtggcggtag cgcggccgct agattcccca acatcaccaa tctgtgcccc  540
ttcggcgagg tgttcaacgc cacaagattc gcctctgtgt acgcctggaa ccggaagcgg  600
atcagcaatt gcgtggccga ctacagcgtg ctgtacaaca gcgccagctt ctccaccttc  660
aagtgctacg gcgtgtcccc taccaagctg aacgacctgt gctttaccaa cgtgtacgcc  720
gatagcttcg tgatccgggg agatgaagtg cggcagatcg ctcctggaca gacaggcaag  780
atcgccgact ataactacaa gctgcccgac gacttcaccg gctgtgtgat tgcctggaac  840
agcaacaacc tggacagcaa agtcggcggc aactacaatt acctgtaccg gctgttccgg  900
aagtccaatc tgaagccctt cgagcgggac atcagcaccg agatctatca ggccggcagc  960
accccttgca atgcgtggaa aggcttcaac tgctacttcc cactgcagtc ctacggcttc 1020
cagcctacaa acggcgtggg ctaccagcct tacagagtgt tggtcctgag cttcgagctg 1080
ctgcatgccc ctgctacagt gtgcggccct aagaagtcta ccaacctgga attctctggc 1140
ggcggaggat ctggcggagg tggaagcgga ggcggtggat ctgcggccgc caagaatgtt 1200
agcctgcaga gctgcacaca gcaccagcct tacgtggtgg acgaccctg tcctatccac  1260
ttctacagca agtggtacat cagagtgggc gccagaaaga gcgcccact gattgagctg   1320
tgtgtggatg aggccggcag caagagcccc atccagtaca tcgacatcgg caactacacc 1380
gtgtcctgcc tgcctttcac catcaactgc caagagccta gctgggctc tctggtcgtg  1440
cggtgcagct ctacgagga cttcctggaa taccacgacg tgcgcgtggt gctggatttc  1500
atcccgcggg tggtggtag tggcggagga agtggtggcg gatctgcttg gagccatcct 1560
cagttcgaga aggcggcgg ttcaggtggt ggatcaggcc gttctgcatg gtcacaccca  1620
cagtttgaga agtga                                                  1635

SEQ ID NO: 8            moltype = AA  length = 544
FEATURE                 Location/Qualifiers
REGION                  1..544
                        note = Synthetic Construct
source                  1..544
                        mol_type = protein
                        organism = synthetic construct
SEQUENCE: 8
MTNKCLLQIA LLLCFSTTAL SMGAPQVQLQ ESGGGSVQAG GSLRLSCVAS GYTDSTYCVG   60
WFRQAPGKER EGVARINTIS GRPWYADSVK GRFTISQDNS KNTVYLQMNS LKPEDTAIYY  120
CTLTTANSRG FCSGGYNYKG QGTQVTVSGG TSGGGGSGGG GSGGGGSAAA RFPNITNLCP  180
FGEVFNATRF ASVYAWNRKR ISNCVADYSV LYNSASFSTF KCYGVSPTKL NDLCFTNVYA  240
DSFVIRGDEV RQIAPGQTGK IADYNYKLPD DFTGCVIAWN SNNLDSKVGG NYNYLRLFR   300
KSNLKPFERD ISTEIYQAGS TPCNGVEGFN CYFPLQSYGF YRVVVLSFEL             360
LHAPATVCGP KKSTNLEFSG GGGSGGGGSG GGGSAAAQEC SLQSCTQHQP YVVDDPCPIH  420
FYSKWYIRVG ARKSAPLIEL CVDEAGSKSP IQYIDIGNYT VSCLPFTINC QEPKLGSLVV  480
RCSFYEDFLE YHDVRVVLDF IPRGGGSGGG SGGGSAWSHP QFEKGGGSGG GSGGSAWSHP  540
QFEK                                                               544

SEQ ID NO: 9            moltype = DNA  length = 810
FEATURE                 Location/Qualifiers
misc_feature            1..810
                        note = Synthetic
source                  1..810
                        mol_type = other DNA
                        organism = synthetic construct
SEQUENCE: 9
atgaccaaca agtgcctgct gcagattgcc ctgctgctgt gcttcagcac aacagccctg   60
tctatgggcg cgcctcaagt tcagcttcaa gaatctggcg gcggaagcgt tcaggctggc  120
ggatctctga gactgagctg tgtggccagc ggctacaccg atagcacata ctgcgtcggc  180
```

```
tggttcagac aggcccctgg caaagagaga gagggcgtcg ccagaatcaa caccatcagc    240
ggcagacctt ggtacgccga ctctgtgaag gcagattca caatcagcca ggacaacagc    300
aagaacaccg tgtacctgca gatgaacagc ctgaagcctg aggacaccgc catctactac    360
tgcacccctga ccaccgccaa cagcagaggc ttttgttccg gcggctacaa ctacaaaggc    420
cagggcaccc aagtgaccgt gtctggtggt accagcggag gcggaggatc aggtggcgga    480
ggtagtggtg gtggcggtag cgcggccgct atggcctact gttggagatg caccagctgc    540
tgcttcagcg agcggttcca gaaccacaat cctcagaaag agatggccac cagcacactg    600
cagggctgtt ctctgtgtct gcagctggcc gtggtggtca actctctgct gaccccttc    660
gccagatgct gctggcctga attcggcgga ggcagcggcg gtggaagcgg cggaggctct    720
gcttggagcc acccgcagtt cgaaaaaggt ggaggttctg gcggtggatc gggaggttca    780
gcgtggagcc acccgcagtt cgagaaatga                                     810

SEQ ID NO: 10           moltype = AA  length = 269
FEATURE                 Location/Qualifiers
REGION                  1..269
                        note = Synthetic Construct
source                  1..269
                        mol_type = protein
                        organism = synthetic construct
SEQUENCE: 10
MTNKCLLQIA LLLCFSTTAL SMGAPQVQLQ ESGGGSVQAG GSLRLSCVAS GYTDSTYCVG    60
WFRQAPGKER EGVARINTIS GRPWYADSVK GRFTISQDNS KNTVYLQMNS LKPEDTAIYY   120
CTLTTANSRG FCSGGYNYKG QGTQVTVSGG TSGGGGSGGG GSGGGGSAAA MAYCWRCTSC   180
CFSERFQNHN PQKEMATSTL QGCSLCLQLA VVVNSLLTPF ARCCWPEFGG GSGGGSGGGS   240
AWSHPQFEKG GGSGGGSGGS AWSHPQFEK                                    269

SEQ ID NO: 11           moltype = DNA  length = 1491
FEATURE                 Location/Qualifiers
misc_feature            1..1491
                        note = Synthetic
source                  1..1491
                        mol_type = other DNA
                        organism = synthetic construct
SEQUENCE: 11
atgaccaaca agtgcctgct gcagattgcc ctgctgctgt gcttcagcac aacagccctg     60
tctatgggcg cgcctcaagt tcagcttcaa gaatctggcg gcggaagcgt tcaggctggc    120
ggatctctga gactgagctg tgtggccagc ggctacaccg atagcacata ctgcgtcggc    180
tggttcagac aggcccctgg caaagagaga gagggcgtcg ccagaatcaa caccatcagc    240
ggcagacctt ggtacgccga ctctgtgaag gcagattca caatcagcca ggacaacagc    300
aagaacaccg tgtacctgca gatgaacagc ctgaagcctg aggacaccgc catctactac    360
tgcacccctga ccaccgccaa cagcagaggc ttttgttccg gcggctacaa ctacaaaggc    420
cagggcaccc aagtgaccgt gtctggtggt accagcggag gcggaggatc aggtggcgga    480
ggtagtggtg gtggcggtag cgcggccgct agattccaca acatccacaa tctgtgccg    540
ttcggcgagg tgttcaacgc cacaagattc gcctctgtgt acgcctggaa ccggaagcgg    600
atcagcaatt gcgtggccga ctacagcgtg ctgtacaaca gcgccagctt ctccaccttc    660
aagtgctacg gcgtgtcccc taccaagctg aacgacctgt gctttaccaa cgtgtacgcc    720
gatagcttcg tgatccgggg agatgaagtg cggcagatcg ctcctggaca gacaggcaag    780
atcgccgact ataactacaa gctgcccgac gacttcaccg gctgtgtgat tgcctggaac    840
agcaacaacc tggacagcaa agtcggcggc aactacaatt acctgtaccg gctgttccgg    900
aagtccaatc tgaagccctt cgagcgggac atcagcaccg agatctatca ggccggcagc    960
accccttgca atggcgtgga aggcttcaac tgctacttcc cactgcagtc ctacggcttc   1020
cagcctacaa acggcgtggg ctaccagcct tacagagtgg tggtcctgag cttcgagctg   1080
ctgcatgccc ctgctacagt gtgcggccct aagaagtcta ccaacctgga attctctggc   1140
ggcggaggat ctggcggagg tggaagcgga ggcggtggat ctgcggccgc tatggcctac   1200
tgttggagat gcaccagctg ctgcttcagc agcggttcca gaaccacaa tcctcagaaa   1260
gagatggcca ccagcacact gcagggctgt tctctgtgtc tgcagctggc cgtggtggtc   1320
aactctctgc tgacccctt cgccagatgc tgctggcctg aattcggcgg aggcagcggc   1380
ggtggaagcg gcggaggctc tgcttggagc cacccgcagt cgaaaaaggt ggaggttct   1440
ggcggtggat cgggaggttc agcgtggagc cacccgcagt cgagaaatga                1491

SEQ ID NO: 12           moltype = AA  length = 496
FEATURE                 Location/Qualifiers
REGION                  1..496
                        note = Synthetic Construct
source                  1..496
                        mol_type = protein
                        organism = synthetic construct
SEQUENCE: 12
MTNKCLLQIA LLLCFSTTAL SMGAPQVQLQ ESGGGSVQAG GSLRLSCVAS GYTDSTYCVG    60
WFRQAPGKER EGVARINTIS GRPWYADSVK GRFTISQDNS KNTVYLQMNS LKPEDTAIYY   120
CTLTTANSRG FCSGGYNYKG QGTQVTVSGG TSGGGGSGGG GSGGGGSAAA RFPNITNLCP   180
FGEVFNATRF ASVYAWNRKR ISNCVADYSV LYNSASFSTF KCYGVSPTKL NDLCFTNVYA   240
DSFVIRGDEV RQIAPGQTGK IADYNYKLPD DFTGCVIAWN SNNLDSKVGG NYNYLYRLFR   300
KSNLKPFERD ISTEIYQAGS TPCNGVEGFN CYFPLQSYGF QPTNGVGYQP YRVVVLSFEL   360
LHAPATVCGP KKSTNLEFSG GGGSGGGGSG GGGSAAAMAY CWRCTSCCFS ERFQNHNPQK   420
EMATSTLQGC SLCLQLAVVV NSLLTPFARC CWPEFGGGSG GGSGGGSAWS HPQFEKGGGS   480
GGGSGGSAWS HPQFEK                                                  496

SEQ ID NO: 13           moltype = DNA  length = 579
```

| FEATURE | Location/Qualifiers |
|---|---|
| misc_feature | 1..579 |
| | note = Synthetic |
| source | 1..579 |
| | mol_type = other DNA |
| | organism = synthetic construct |

SEQUENCE: 13

```
atgaccaaca agtgcctgct gcagattgcc ctgctgctgt gcttcagcac aacagccctg   60
tctatgggcg cgcctcaagt tcagcttcaa gaatctggcg gcggaagcgt tcaggctggc  120
ggatctctga gactgagctg tgtggccagc ggctacaccg atagcacata ctgcgtcggc  180
tggttcagac aggcccctgg caaagagaga gagggcgtcg ccagaatcaa caccatcagc  240
ggcagacctt ggtacgccga ctctgtgaag ggcagattca caatcagcca ggacaacagc  300
aagaacaccg tgtacctgca gatgaacagc ctgaagcctg aggacaccgc catctactac  360
tgcacccctga ccaccgccaa cagcagaggc ttttgttcgg gcggctacaa ctacaaaggc  420
cagggcaccc aagtgaccgt gtctggtgaa ttcggcggag gcagcggcgg tggaagcggc  480
ggaggctctg cttggagcca cccgcagttc gaaaaaggtg gaggttctgg cggtggatcg  540
ggaggttcag cgtggagcca cccgcagttc gagaaatga                         579
```

| SEQ ID NO: 14 | moltype = AA length = 192 |
|---|---|
| FEATURE | Location/Qualifiers |
| REGION | 1..192 |
| | note = Synthetic Construct |
| source | 1..192 |
| | mol_type = protein |
| | organism = synthetic construct |

SEQUENCE: 14

```
MTNKCLLQIA LLLCFSTTAL SMGAPQVQLQ ESGGGSVQAG GSLRLSCVAS GYTDSTYCVG   60
WFRQAPGKER EGVARINTIS GRPWYADSVK GRFTISQDNS KNTVYLQMNS LKPEDTAIYY  120
CTLTTANSRG FCSGGYNYKG QGTQVTVSGE FGGGSGGGSG GGSAWSHPQF EKGGGSGGGS  180
GGSAWSHPQF EK                                                      192
```

| SEQ ID NO: 15 | moltype = DNA length = 1776 |
|---|---|
| FEATURE | Location/Qualifiers |
| misc_feature | 1..1776 |
| | note = Synthetic |
| source | 1..1776 |
| | mol_type = other DNA |
| | organism = synthetic construct |

SEQUENCE: 15

```
atgaccaaca agtgcctgct gcagattgcc ctgctgctgt gcttcagcac aacagccctg   60
tctatgggcg cgcctcaggt tcagctggtt gaatctggcg gaggcctgat gcaagctggc  120
ggatctctga gactgagctg tgccgtgtcc ggcagaacct tttctacagc cgccatgggc  180
tggttcagac aggcccctgg aaaagaacgc gagttcgtgg ccgctatccg ttggagcgga  240
ggctctgcct actacgccga ttctgtgaag ggcagattca ccatcagcag agacaaggcc  300
aagaacaccg tgtacctgca gatgaacagc ctgaagtacg aggacaccgc cgtgtactac  360
tgcgccagaa cagagaatgt gcggagcctg ctgagcgact acgccacctg gccttacgat  420
tattggggcc agggcaccca agtgaccgtt tctggtggag gaagcggcgg aggagga    480
tcaggtggcg gtggatctat cgatcaggtg cagctcgtgg aaagcggtgg cggacttatg  540
caggcaggcg gaagcctgag actgtcttgt gctgtgtctg gccggacctt tagcaccgct  600
gctatgggat ggtttaggca ggctccagcc aaagaaaggg aatttgtggc cgccattcgt  660
tggagtggcg gcagcgccta ttatgccgat agcgtgaaag gccggttcac catctctcga  720
gataaggcta agaatacggt ctatctccag atgaactccc tcaaatatga ggatacggcc  780
gtctactatt gtgcccggac cgaaaatgtg cgctccctgc tgtctgatta tgccacatgg  840
ccctatgact actggggaca gggaacacaa gtcacagtgt ccagcggtac cggcggaggt  900
ggaagcggag gcggaggctc tggccgcggt ggatctggat ccgagcctaa gagctgcgac  960
aagacccaca cctgtcctcc atgtcctgct ccagaactgc tcggcggacc ttccgtgttc 1020
ctgtttcctc caaagcctaa ggacaccctg atgatcagca gaaccctgag agtgacctgc 1080
gtggtggtgg atgtgtccca cgaagatccc gaagtgaagt tcaattggta cgtggacggc 1140
gtggaagtgc acaacgccaa gaccaagcct agagaggaac agtacaacag cacctacaga 1200
gtggtgtccg tgctgaccgt gctgcaccag gattggctga acggcaaaga gtacaagtgc 1260
aaggtgtcca acaaggccct gcctgctcct atcgagaaaa ccatcagcaa ggccaagggc 1320
cagcctaggg aacccaggt ttacacactg cctccaagcc gggaagagat gaccaagaac 1380
caggtgtccc tgacctgcct ggtcaagggc ttctacccgt ccgatatcgc cgtggaatgg 1440
gagagcaatg gccagcctga gaacaactac aagacaaccc ctcctgtgct ggacagcgac 1500
ggctcattct tcctgtatag caagctgaca gtggacaaga gcagatggca gcagggcaac 1560
gtgttcagct gcagcgtgat gcacgaggcc ctgcacaacc actacaccca gaagtccctg 1620
agcctgtctc tgggcaagcc gcggggtggt ggttccggcg gaggtagtgg cggcggatct 1680
gcgggccgctt ggagccatcc tcagttcgag aaaggcggag gaagcggcgg aggcagcggt 1740
ggtggctctt ggtcacatcc ccagtttgag aagtga                           1776
```

| SEQ ID NO: 16 | moltype = AA length = 591 |
|---|---|
| FEATURE | Location/Qualifiers |
| REGION | 1..591 |
| | note = Synthetic Construct |
| source | 1..591 |
| | mol_type = protein |
| | organism = synthetic construct |

SEQUENCE: 16

```
MTNKCLLQIA LLLCFSTTAL SMGAPQVQLV ESGGGLMQAG GSLRLSCAVS GRTFSTAAMG   60
```

-continued

```
WFRQAPGKER EFVAAIRWSG GSAYYADSVK GRFTISRDKA KNTVYLQMNS LKYEDTAVYY    120
CARTENVRSL LSDYATWPYD YWGQGTQVTV SGGGGSGGGG SGGGGSIDQV QLVESGGGLM    180
QAGGSLRLSC AVSGRTFSTA AMGWFRQAPG KEREFVAAIR WSGGSAYYAD SVKGRFTISR    240
DKAKNTVYLQ MNSLKYEDTA VYYCARTENV RSLLSDYATW PYDYWGQGTQ VTVSSGTGGG    300
GSGGGGSGGG GSGSEPKSCD KTHTCPPCPA PELLGGPSVF LFPPKPKDTL MISRTPEVTC    360
VVVDVSHEDP EVKFNWYVDG VEVHNAKTKP REEQYNSTYR VVSVLTVLHQ DWLNGKEYKC    420
KVSNKALPAP IEKTISKAKG QPREPQVYTL PPSREEMTKN QVSLTCLVKG FYPSDIAVEW    480
ESNGQPENNY KTTPPVLDSD GSFFLYSKLT VDKSRWQQGN VFSCSVMHEA LHNHYTQKSL    540
SLSPGKPRGG GSGGGSGGGS AAAWSHPQFE KGGGSGGGSG GGSWSHPQFE K             591

SEQ ID NO: 17           moltype = DNA  length = 1215
FEATURE                 Location/Qualifiers
misc_feature            1..1215
                        note = Synthetic
source                  1..1215
                        mol_type = other DNA
                        organism = synthetic construct
SEQUENCE: 17
atgaccaaca agtgcctgct gcagattgcc ctgctgctgt gcttcagcac aacagccctg    60
tctatgggcg cgcctcaggt tcagctggtt gaatctggcg gaggcctgat gcaagctggc    120
ggatctctga gactgagctg tgccgtgtcc ggcagaacct tttctacagc cgccatgggc    180
tggttcagac aggcccctgg aaaagaacgc gagttcgtcg ccgctatccg ttggagcgga    240
ggctctgcct actacgccga ttctgtgaag gcagattca ccatcagcag agacaaggcc     300
aagaacaccg tgtacctgca gatgaacagc ctgaagtacg aggacaccgc cgtgtactac    360
tgcgccagaa cagagaatgt gcggagcctg ctgagcgact acgccacctg gccttacgat    420
tattgggcag agggcaccca agtgaccgtt tctggtggcg gaggaagcgg aggcggagga    480
tcaggtggcg gtggatctat cgatcaggtg cagctcgtgg aaagcggtgg cggacttatg    540
caggcaggcg gaagcctgag actgtcttgt gctgtgtctg gccggacctt tagcaccgct    600
gctatgggat ggtttaggca ggctccaggc aagaaaggg aatttgtggc cgccattcgt     660
tggagtggcg gcagcgccta ttatgccgat agcgtgaag gccggttcac catctctcgc    720
gataaggcta agaatacggt ctatctccag atgaactccc tcaaatatga ggatacggcc    780
gtctactatt gtgcccggac cgaaaatgtg cgctccctgc tgtctgatta tgccacatgg    840
ccctatgact actggggaca gggaacacaa gtcacagtgt ccagcggtac cgagcctaag    900
atccctcagc ctcagccaaa gcctcaacca caaccgcagc cacagcctaa accgcagcct    960
aagccagagc ctgagcagcg gatgaagcag atcgaggaca agatcgaaga gatcctgagc    1020
aaaatctacc acatcgagaa cgagatcgcc cggatcaaga agctcgtcgg cgaaagaccg    1080
cggggtggtg gttccggcgg aggtagtggc ggcggatctg cggccgcttg gagccatcct    1140
cagttcgaga aggcgcgagg aagcggcgga ggcagcggtg gtggctcttg gtcacatccc    1200
cagtttgaga agtga                                                     1215

SEQ ID NO: 18           moltype = AA  length = 404
FEATURE                 Location/Qualifiers
REGION                  1..404
                        note = Synthetic Construct
source                  1..404
                        mol_type = protein
                        organism = synthetic construct
SEQUENCE: 18
MTNKCLLQIA LLLCFSTTAL SMGAPQVQLV ESGGGLMQAG GSLRLSCAVS GRTFSTAAMG    60
WFRQAPGKER EFVAAIRWSG GSAYYADSVK GRFTISRDKA KNTVYLQMNS LKYEDTAVYY    120
CARTENVRSL LSDYATWPYD YWGQGTQVTV SGGGGSGGGG SGGGGSIDQV QLVESGGGLM    180
QAGGSLRLSC AVSGRTFSTA AMGWFRQAPG KEREFVAAIR WSGGSAYYAD SVKGRFTISR    240
DKAKNTVYLQ MNSLKYEDTA VYYCARTENV RSLLSDYATW PYDYWGQGTQ VTVSSGTEPK    300
IPQPQPKPQP QPQPQPKPQP KPEPEQRMKQ IEDKIEEILS KIYHIENEIA RIKKLVGERP    360
RGGGSGGGSG GGSAAAWSHP QFEKGGGSGG GSGGGSWSHP QFEK                     404

SEQ ID NO: 19           moltype = DNA  length = 66
FEATURE                 Location/Qualifiers
misc_feature            1..66
                        note = Synthetic
source                  1..66
                        mol_type = other DNA
                        organism = synthetic construct
SEQUENCE: 19
atgaccaaca agtgcctgct gcagattgcc ctgctgctgt gcttcagcac aacagccctg    60
tctatg                                                                66

SEQ ID NO: 20           moltype = AA  length = 22
FEATURE                 Location/Qualifiers
REGION                  1..22
                        note = Synthetic Construct
source                  1..22
                        mol_type = protein
                        organism = synthetic construct
SEQUENCE: 20
MTNKCLLQIA LLLCFSTTAL SM                                              22

SEQ ID NO: 21           moltype = DNA  length = 369
FEATURE                 Location/Qualifiers
```

```
misc_feature            1..369
                        note = Synthetic
source                  1..369
                        mol_type = other DNA
                        organism = synthetic construct
SEQUENCE: 21
caagttcagc ttcaagaatc tggcggcgga agcgttcagg ctggcggatc tctgagactg   60
agctgtgtgg ccagcggcta caccgatagc acatactgcg tcggctggtt cagacaggcc  120
cctggcaaag agagagggg cgtcgccaga atcaacacca tcagcggcag accttggtac  180
gccgactctg tgaagggcag attcacaatc agccaggaca acagcaagaa caccgtgtac  240
ctgcagatga acagcctgaa gcctgaggac accgccatct actactgcac cctgaccacc  300
gccaacagca gaggcttttg ttccggcggc tacaactaca aaggccaggg cacccaagtg  360
accgtgtct                                                           369

SEQ ID NO: 22           moltype = AA  length = 123
FEATURE                 Location/Qualifiers
REGION                  1..123
                        note = Synthetic Construct
source                  1..123
                        mol_type = protein
                        organism = synthetic construct
SEQUENCE: 22
QVQLQESGGG SVQAGGSLRL SCVASGYTDS TYCVGWFRQA PGKEREGVAR INTISGRPWY   60
ADSVKGRFTI SQDNSKNTVY LQMNSLKPED TAIYYCTLTT ANSRGFCSGG YNYKGQGTQV  120
TVS                                                                 123

SEQ ID NO: 23           moltype = DNA  length = 3822
FEATURE                 Location/Qualifiers
source                  1..3822
                        mol_type = other DNA
                        organism = SARS-CoV-2
SEQUENCE: 23
atgtttgttt ttcttgtttt attgccacta gtctctagtc agtgtgttaa tcttacaacc   60
agaactcaat taccccctgc atacactaat tctttcacac gtggtgttta ttaccctgac  120
aaagttttca gatcctcagt tttacattca actcaggact tgttcttacc tttcttttcc  180
aatgttactt ggttccatgc tatacatgtc tctgggacca atggtactaa gaggtttgat  240
aaccctgtcc taccatttaa tgatggtgtt tattttgctt ccactgagaa gtctaacata  300
ataagaggct ggatttttgg tactacttta gattcgaaga cccagtccct acttattgtt  360
aataacgcta ctaatgttgt tattaaagtc tgtgaatttc aattttgtaa tgatccattt  420
ttgggtgttt attaccacaa aaacaacaaa agttggatgg aaagtgagtt cagagtttat  480
tctagtgcga ataattgcac ttttgaatat gtctctcagc cttttcttat ggaccttgaa  540
ggaaaacagg gtaatttcaa aaatcttagg gaatttgtgt ttaagaatat tgatggttat  600
tttaaaatat atttcaagca cacgcctatt aatttagtgc gtgatctccc tcagggtttt  660
tcggctttag aaccattggt agatttgcca ataggtatta acatcactag gtttcaaact  720
ttacttgctt tacatagaag ttatttgact cctggtgatt cttcttcagg ttggacagct  780
ggtgctgcag cttattatgt gggttatctt caacctagga cttttctatt aaaatataat  840
gaaaatggaa ccattacaga tgctgtagac tgtgcacttg accctctctc agaaacaaag  900
tgtacgttga atccttcac tgtagaaaaa ggaatctatc aaacttctaa ctttagagtc  960
caaccaacag aatctattgt tagatttcct aatattacaa acttgtgccc ttttggtgaa 1020
gtttttaacg ccaccagatt tgcatctgtt tatgcttgga acaggaagag aatcagcaac 1080
tgtgttgctg attattctgt cctatataat tccgcatcat tttccacttt taagtgttat 1140
ggagtgtctc ctactaaatt aaatgatctc tgctttacta atgtctatgc agattcattt 1200
gtaattagag gtgatgaagt cagacaaatc gctccagggc aaactggaaa gattgctgat 1260
tataattata aattaccaga tgattttaca ggctgcgtta tagcttggaa ttctaacaat 1320
cttgatttcta aggttggtgg taattataat acctgtata gattgtttag gaagtctaat 1380
ctcaaacctt ttgagagaga tatttcaact gaaatctatc aggccggtag cacaccttgt 1440
aatggtgttg aaggttttaa ttgttacttt cctttacaat catatggttt ccaacccact 1500
aatggtgttg gttaccaacc atacagagta gtagtacttt cttttgaact tctacatgca 1560
ccagcaactg tttgtggacc taaaaagtct actaatttgg ttaaaaacaa atgtgtcaat 1620
ttcaacttca atggtttaac aggcacaggt gttcttactg agtctaacaa aaagtttctg 1680
cctttccaac aatttggcag agacattgct gacactactg atgctgtccg tgatccacag 1740
acacttgaga tccttgacat tacaccatgt tcttttggtg gtgtcagtgt ataacacca 1800
ggaacaaata cttctaacca ggttgctgtt ctttatcagg atgttaactg cacagaagtc 1860
cctgttgcta ttcatgcaga tcaacttact cctacttggc gtgtttattc tacaggttct 1920
aatgtttttc aaacacgtgc aggctgttta ataggggctg aacatgtcaa caactctat 1980
gagtgtgaca tacccattgg tgcaggtata tgcgctagtt atcagactca gactaattct 2040
cctcggcggg cacgtagtgt agctagtcaa tccatcattg cctacactat gtcacttggt 2100
gcagaaaatt cagttgctta ctctaataac tcttattgcca tacccacaaa tttttactatt 2160
agtgttacca cagaaattct accagtgtct atgaccaaga catcagtaga ttgtacaatg 2220
tacatttgtg gtgattcaac tgaatgcagc aatcttttgt tgcaatatgg cagtttttgt 2280
acacaattaa accgtgcttt aactggaata gctgttgaac aagacaaaaa cacccaagaa 2340
gtttttgcac aagtcaaaca aatttacaaa acaccaccaa ttaaagattt tggtggtttt 2400
aatttttcac aaatattacc agatccatca aaaccaagca gaggtcatt tattgaagat 2460
ctactttttca acaaagtgac acttgcagat gctggcttca tcaaacaata tggtgattgc 2520
cttggtgata ttgctgctag agacctcatt tgtgcacaaa agtttaacgg ccttactgtt 2580
ttgccaccttt tgctcacaga tgaaatgatt gctaatacaa cttctgcact gttagcgggt 2640
acaatcactt ctggttggac ctttggtgca ggtgctgcat tacaaatacc atttgctatg 2700
caaatggctt ataggtttaa tggtattgga gttacacaga tgttctcta tgagaaccaa 2760
aaattgattg ccaaccaatt taatagtgct attggcaaaa ttcaagactc actttcttcc 2820
```

-continued

```
acagcaagtg cacttggaaa acttcaagat gtggtcaacc aaaatgcaca agcttttaaac    2880
acgcttgtta aacaacttag ctccaatttt ggtgcaattt caagtgtttt aaatgatatc    2940
ctttcacgtc ttgacaaagt tgaggctgaa gtgcaaattg ataggttgat cacaggcaga    3000
cttcaaagtt tgcagacata tgtgactcaa caattaatta gagctgcaga aatcagagct    3060
tctgctaatc ttgctgctac taaaatgtca gagtgtgtac ttggacaatc aaaaagagtt    3120
gattttttgtg aaagggctta tcatcttatg tccttccctc agtcagcacc tcatggtgta    3180
gtcttcttgc atgtgactta tgtccctgca caagaaaaga acttcacaac tgctcctgcc    3240
atttgtcatg atggaaaagc acactttcct cgtgaaggtg tctttgtttc aaatggcaca    3300
cactggtttg taacacaaag gaatttttat gaaccacaaa tcattactac agacaacaca    3360
tttgtgtctg gtaactgtga tgttgtaata ggaattgtca acaacacagt ttatgatcct    3420
ttgcaacctg aattagactc attcaaggag gagttagata aatattttaa gaatcataca    3480
tcaccagatg ttgatttagg tgacatctct ggcattaatg cttcagttgt aaacattcaa    3540
aaagaaattg accgcctcaa tgaggttgcc aagaatttaa atgaatctct catcgatctc    3600
caagaacttg gaaagtatga gcagtatata aaatggccat ggtacatttg gctaggtttc    3660
atagctggct tgattgccat agtaatggtg acaattatgc tttgctgtat gaccagttgc    3720
tgtagttgtc tcaagggctg ttgttcttgt ggatcctgct gcaaatttga tgaagacgac    3780
tctgagccag tgctcaaagg agtcaaatta cattacacat aa                       3822

SEQ ID NO: 24          moltype = AA  length = 1273
FEATURE                Location/Qualifiers
source                 1..1273
                       mol_type = protein
                       organism = SARS-CoV-2
SEQUENCE: 24
MFVFLVLLPL VSSQCVNLTT RTQLPPAYTN SFTRGVYYPD KVFRSSVLHS TQDLFLPFFS     60
NVTWFHAIHV SGTNGTKRFD NPVLPFNDGV YFASTEKSNI IRGWIFGTTL DSKTQSLLIV    120
NNATNVVIKV CEFQFCNDPF LGVYYHKNNK SWMESEFRVY SSANNCTFEY VSQPFLMDLE    180
GKQGNFKNLR EFVFKNIDGY FKIYSKHTPI NLVRDLPQGF SALEPLVDLP IGINITRFQT    240
LLALHRSYLT PGDSSSGWTA GAAAYYVGYL QPRTFLLKYN ENGTITDAVD CALDPLSETK    300
CTLKSFTVEK GIYQTSNFRV QPTESIVRFP NITNLCPFGE VFNATRFASV YAWNRKRISN    360
CVADYSVLYN SASFSTFKCY GVSPTKLNDL CFTNVYADSF VIRGDEVRQI APGQTGKIAD    420
YNYKLPDDFT GCVIAWNSNN LDSKVGGNYN YLYRLFRKSN LKPFERDIST EIYQAGSTPC    480
NGVEGFNCYF PLQSYGFQPT NGVGYQPYRV VVLSFELLHA PATVCGPKKS TNLVKNKCVN    540
FNFNGLTGTG VLTESNKKFL PFQQFGRDIA DTTDAVRDPQ TLEILDITPC SFGGVSVITP    600
GTNTSNQVAV LYQDVNCTEV PVAIHADQLT PTWRVYSTGS NVFQTRAGCL IGAEHVNNSY    660
ECDIPIGAGI CASYQTQTNS PRRARSVASQ SIIAYTMSLG AENSVAYSNN SIAIPTNFTI    720
SVTTEILPVS MTKTSVDCTM YICGDSTECS NLLLQYGSFC TQLNRALTGI AVEQDKNTQE    780
VFAQVKQIYK TPPIKDFGGF NFSQILPDPS KPSKRSFIED LLFNKVTLAD AGFIKQYGDC    840
LGDIAARDLI CAQKFNGLTV LPPLLTDEMI AQYTSALLAG TITSGWTFGA GAALQIPFAM    900
QMAYRFNGIG VTQNVLYENQ KLIANQFNSA IGKIQDSLSS TASALGKLQD VVNQNAQALN    960
TLVKQLSSNF GAISSVLNDI LSRLDKVEAE VQIDRLITGR LQSLQTYVTQ QLIRAAEIRA   1020
SANLAATKMS ECVLGQSKRV DFCGKGYHLM SFPQSAPHGV VFLHVTYVPA QEKNFTTAPA   1080
ICHDGKAHFP REGVFVSNGT HWFVTQRNFY EPQIITTDNT FVSGNCDVVI GIVNNTVYDP   1140
LQPELDSFKE ELDKYFKNHT SPDVDLGDIS GINASVVNIQ KEIDRLNEVA KNLNESLIDL   1200
QELGKYEQYI KWPWYIWLGF IAGLIAIVMV TIMLCCMTSC CSCLKGCCSC GSCCKFDEDD   1260
SEPVLKGVKL HYT                                                     1273

SEQ ID NO: 25          moltype = DNA  length = 1260
FEATURE                Location/Qualifiers
source                 1..1260
                       mol_type = other DNA
                       organism = SARS-CoV-2
SEQUENCE: 25
atgtctgata atggacccca aaatcagcga atgcacccc gcattacgtt tggtggaccc      60
tcagattcaa ctggcagtaa ccagaatgga gaacgcagtg gggcgcgatc aaaacaacgt    120
cggccccaag gtttacccaa taatactgcg tcttggttca ccgctctcac tcaacatggc    180
aaggaagacc ttaaattccc tcgaggacaa ggcgttccaa ttaacaccaa tagcagtcca    240
gatgaccaaa ttggctacta ccgaagagct accagacgaa ttcgtggtgg tgacggtaaa    300
atgaaagatc tcagtccaag atggtatttc tactacctag gaactgggcc agaagctgga    360
cttccctatg gtgctaacaa agacgggcat catatggggtt g caactgaggg agccttgaat    420
acaccaaaag atcacattgg cacccgcaat cctgctaaca atgctgcaat cgtgctacaa    480
cttcctcaag gaacaacatt gccaaaaggc ttctacgcag aagggagcag aggcggcagt    540
caagcctctt ctcgttcctc atcacgtagt cgcaacagtt caagaaattc aactccaggc    600
agcagtaggg gaacttctcc tgctagaatg gctggcaatg gtgctcttgc tgctgctgc    660
ttgctgctgc ttgacagatt gaaccagctt gagagcaaaa tgtctggtaa aggccaacaa    720
caacaaggcc aaactgtcac taagaaatct gctgctgagg cttctaagaa gcctcggcaa    780
aaacgtactg ccactaaagc ataacaatgta acacaagctt cggcagacg tggtccagaa    840
caaacccaag gaaattttgg ggaccaggaa ctaatcagac aaggaactta tacaaacat    900
tggccgcaaa ttgcacaatt tgcccccagc gcttcagcgt tcttcggaat gtcgcgcatt    960
ggcatggaag tcacaccttc gggaacgtgg ttgacctaca caggtgccat caaattggat   1020
gacaaagatc caaatttcaa agatcaagtc attttgctga ataagcatat gacgcatac    1080
aaaacattcc caccaacaga gcctaaaaag gacaaaaaga gaaggctga tgaaactcaa    1140
gccttaccgc agagacagaa gaaacagcaa actgtgactc ttcttcctgc tgcagatttg    1200
gatgatttctc caaacaatt gcaacaatcc atgagcagtg ctgactcaac tcaggcctaa    1260

SEQ ID NO: 26          moltype = AA  length = 419
FEATURE                Location/Qualifiers
source                 1..419
                       mol_type = protein
```

```
                        organism = SARS-CoV-2
SEQUENCE: 26
MSDNGPQNQR NAPRITFGGP SDSTGSNQNG ERSGARSKQR RPQGLPNNTA SWFTALTQHG    60
KEDLKFPRGQ GVPINTNSSP DDQIGYYRRA TRRIRGGDGK MKDLSPRWYF YYLGTGPEAG   120
LPYGANKDGI IWVATEGALN TPKDHIGTRN PANNAAIVLQ LPQGTTLPKG FYAEGSRGGS   180
QASSRSSSRS RNSSRNSTPG SSRGTSPARM AGNGGDAALA LLLLDRLNQL ESKMSGKGQQ   240
QQGQTVTKKS AAEASKKPRQ KRTATKAYNV TQAFGRRGPE QTQGNFGDQE LIRQGTDYKH   300
WPQIAQFAPS ASAFFGMSRI GMEVTPSGTW LTYTGAIKLD DKDPNFKDQV ILLNKHIDAY   360
KTFPPTEPKK DKKKKADETQ ALPQRQKKQQ TVTLLPAADL DDFSKQLQQS MSSADSTQA    419

SEQ ID NO: 27           moltype = DNA  length = 366
FEATURE                 Location/Qualifiers
source                  1..366
                        mol_type = other DNA
                        organism = SARS-CoV-2
SEQUENCE: 27
atgaaatttc ttgttttctt aggaatcatc acaactgtag ctgcatttca ccaagaatgt    60
agtttacagt catgtactca acatcaacca tatgtagttg atgaccegtg tcctattcac   120
ttctattcta aatggtatat tagagtagga gctagaaaat cagcaccttt aattgaattg   180
tgcgtggatg aggctggttc taaatcaccc attcagtaca tcgatatcgg taattataca   240
gtttcctgtt tacctttac aattaattgc aggaaccta aattgggtag tcttgtagtg    300
cgttgttcgt tctatgaaga cttttagag tatcatgacg ttcgtgttgt tttagatttc    360
atctaa                                                              366

SEQ ID NO: 28           moltype = AA  length = 121
FEATURE                 Location/Qualifiers
source                  1..121
                        mol_type = protein
                        organism = SARS-CoV-2
SEQUENCE: 28
MKFLVFLGII TTVAAFHQEC SLQSCTQHQP YVVDDPCPIH FYSKWYIRVG ARKSAPLIEL    60
CVDEAGSKSP IQYIDIGNYT VSCLPFTINC QEPKLGSLVV RCSFYEDFLE YHDVRVVLDF   120
I                                                                   121

SEQ ID NO: 29           moltype = DNA  length = 300
FEATURE                 Location/Qualifiers
source                  1..300
                        mol_type = other DNA
                        organism = SARS-CoV-2
SEQUENCE: 29
atggcctact gttggagatg caccagctgc tgcttcagcg agcggttcca gaaccacaat    60
cctcagaaag agatggccac cagcacactg cagggctgtt ctctgtgtct gcagctggcc   120
gtggtgtca actctctgct gacccctttc gccagatgt gctggcctga attcggcgga    180
ggcagcggcg gtggaagcgg cggaggctct gcttggagcc accgcagtt cgaaaaaggt    240
ggaggttctg gcggtggatc gggaggttca gcgtggagcc accgcagtt cgagaaatga    300

SEQ ID NO: 30           moltype = AA  length = 99
FEATURE                 Location/Qualifiers
source                  1..99
                        mol_type = protein
                        organism = SARS-CoV-2
SEQUENCE: 30
MAYCWRCTSC CFSERFQNHN PQKEMATSTL QGCSLCLQLA VVNSLLTPF ARCCWPEFGG    60
GSGGGSGGGS AWSHPQFEKG GGSGGGSGGS AWSHPQFEK                          99

SEQ ID NO: 31           moltype = DNA  length = 378
FEATURE                 Location/Qualifiers
misc_feature            1..378
                        note = Synthetic
source                  1..378
                        mol_type = other DNA
                        organism = synthetic construct
SEQUENCE: 31
caggttcagc tggttgaatc tggcggaggc ctgatgcaag ctggcggatc tctgagactg    60
agctgtgccg tgtccggcag aacctttct acagccgcca tgggctggtt cagacaggcc   120
cctgaaaag aacgcgagtt cgtggccgct atcgttgga gcgaggctc tgcctactac    180
gccgattctg tgaagggcag attcaccatc agcagagaca aggccaagaa caccgtgtac   240
ctgcagatga acagcctgaa gtacgaggac accgccgtgt actactgcgc cagaacagag   300
aatgtgcgga gcctgctgag cgactacgcc acctggcctt acgattattg gggccagggc   360
acccaagtga ccgtttct                                                 378

SEQ ID NO: 32           moltype = AA  length = 126
FEATURE                 Location/Qualifiers
REGION                  1..126
                        note = Synthetic Construct
source                  1..126
                        mol_type = protein
                        organism = synthetic construct
SEQUENCE: 32
```

```
QVQLVESGGG LMQAGGSLRL SCAVSGRTFS TAAMGWFRQA PGKEREFVAA IRWSGGSAYY    60
ADSVKGRFTI SRDKAKNTVY LQMNSLKYED TAVYYCARTE NVRSLLSDYA TWPYDYWGQG   120
TQVTVS                                                             126

SEQ ID NO: 33           moltype = DNA  length = 696
FEATURE                 Location/Qualifiers
misc_feature            1..696
                        note = Synthetic
source                  1..696
                        mol_type = other DNA
                        organism = synthetic construct
SEQUENCE: 33
gagcctaaga gctgcgacaa gacccacacc tgtcctccat gtcctgctcc agaactgctc    60
ggcggacctt ccgtgttcct gtttcctcca aagcctaagg acaccctgat gatcagcaga   120
acccctgaag tgacctgcgt ggtggtggat gtgtcccacg aagatcccga agtgaagttc   180
aattggtacg tggacggcgt ggaagtgcac aacgccaaga ccaagcctag agaggaacag   240
tacaacagca cctacagagt ggtgtccgtg ctgaccgtgc tgcaccagga ttggctgaac   300
ggcaaagagt acaagtgcaa ggtgtccaac aaggccctgc ctgctcctat cgagaaaacc   360
atcagcaagg ccaagggcca gcctagggaa ccccaggttt acacactgcc tccaagccgg   420
gaagagatga ccaagaacca ggtgtccctg acctgcctgg tcaagggctt ctacccttcc   480
gatatcgccg tggaatggga gagcaatggc cagcctgaga caactacaa gacaacccct    540
cctgtgctgg acagcgacgg ctcattcttc ctgtatagca agctgacagt ggacaagagc   600
agatggcagc agggcaacgt gttcagctgc agcgtgatgc acgaggccct gcacaaccac   660
tacacccaga agtccctgag cctgtctcct ggcaag                             696

SEQ ID NO: 34           moltype = AA  length = 232
FEATURE                 Location/Qualifiers
REGION                  1..232
                        note = Synthetic Construct
source                  1..232
                        mol_type = protein
                        organism = synthetic construct
SEQUENCE: 34
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR EEMTKNQVSL TCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 35           moltype = DNA  length = 186
FEATURE                 Location/Qualifiers
misc_feature            1..186
                        note = Synthetic
source                  1..186
                        mol_type = other DNA
                        organism = synthetic construct
SEQUENCE: 35
gagcctaaga tccctcagcc tcagccaaag cctcaaccac aaccgcagcc acagcctaaa    60
ccgcagccta agccagagcc tgagcagcgg atgaagcaga tcgaggacaa gatcgaagag   120
atcctgagca aaatctacca catcgagaac gagatcgccc ggatcaagaa gctcgtcggc   180
gaaaga                                                             186

SEQ ID NO: 36           moltype = AA  length = 62
FEATURE                 Location/Qualifiers
REGION                  1..62
                        note = Synthetic Construct
source                  1..62
                        mol_type = protein
                        organism = synthetic construct
SEQUENCE: 36
EPKIPQPQPK PQPQPQPQPK PQPKPEPEQR MKQIEDKIEE ILSKIYHIEN EIARIKKLVG    60
ER                                                                  62

SEQ ID NO: 37           moltype =     length =
SEQUENCE: 37
000

SEQ ID NO: 38           moltype =     length =
SEQUENCE: 38
000

SEQ ID NO: 39           moltype = DNA  length = 66
FEATURE                 Location/Qualifiers
misc_feature            1..66
                        note = Synthetic
source                  1..66
                        mol_type = other DNA
                        organism = synthetic construct
SEQUENCE: 39
ggtggtacca gcggaggcgg aggatcaggt ggcggaggta gtggtggtgg cggtagcgcg    60
```

```
gccgcc                                                                 66

SEQ ID NO: 40           moltype = AA  length = 22
FEATURE                 Location/Qualifiers
REGION                  1..22
                        note = Synthetic Construct
source                  1..22
                        mol_type = protein
                        organism = synthetic construct
SEQUENCE: 40
GGTSGGGGSG GGGSGGGGSA AA                                               22

SEQ ID NO: 41           moltype = DNA  length = 42
FEATURE                 Location/Qualifiers
misc_feature            1..42
                        note = Synthetic
source                  1..42
                        mol_type = other DNA
                        organism = synthetic construct
SEQUENCE: 41
gaattcggcg gaggcagcgg cggtggaagc ggcggaggct ct                         42

SEQ ID NO: 42           moltype = AA  length = 14
FEATURE                 Location/Qualifiers
REGION                  1..14
                        note = Synthetic Construct
source                  1..14
                        mol_type = protein
                        organism = synthetic construct
SEQUENCE: 42
EFGGGSGGGS GGGS                                                        14

SEQ ID NO: 43           moltype = DNA  length = 45
FEATURE                 Location/Qualifiers
misc_feature            1..45
                        note = Synthetic
source                  1..45
                        mol_type = other DNA
                        organism = synthetic construct
SEQUENCE: 43
atcccgcggg gtggtggtag tggcggagga agtggtggcg gatct                      45

SEQ ID NO: 44           moltype = AA  length = 15
FEATURE                 Location/Qualifiers
REGION                  1..15
                        note = Synthetic Construct
source                  1..15
                        mol_type = protein
                        organism = synthetic construct
SEQUENCE: 44
IPRGGGSGGG SGGGS                                                       15

SEQ ID NO: 45           moltype = DNA  length = 63
FEATURE                 Location/Qualifiers
misc_feature            1..63
                        note = Synthetic
source                  1..63
                        mol_type = other DNA
                        organism = synthetic construct
SEQUENCE: 45
gaattctctg gcggcggagg atctggcgga ggtggaagcg gaggcggtgg atctgcggcc      60
gcc                                                                    63

SEQ ID NO: 46           moltype = AA  length = 21
FEATURE                 Location/Qualifiers
REGION                  1..21
                        note = Synthetic Construct
source                  1..21
                        mol_type = protein
                        organism = synthetic construct
SEQUENCE: 46
EFSGGGGSGG GGSGGGGSAA A                                                21

SEQ ID NO: 47           moltype =    length =
SEQUENCE: 47
000

SEQ ID NO: 48           moltype =    length =
SEQUENCE: 48
```

```
000

SEQ ID NO: 49          moltype = DNA   length = 45
FEATURE                Location/Qualifiers
misc_feature           1..45
                       note = Synthetic
source                 1..45
                       mol_type = other DNA
                       organism = synthetic construct
SEQUENCE: 49
ggtgaattcg gcggaggcag cggcggtgga agcggcggag gctct                          45

SEQ ID NO: 50          moltype = AA   length = 15
FEATURE                Location/Qualifiers
REGION                 1..15
                       note = Synthetic Construct
source                 1..15
                       mol_type = protein
                       organism = synthetic construct
SEQUENCE: 50
GEFGGGSGGG SGGGS                                                           15

SEQ ID NO: 51          moltype = DNA   length = 51
FEATURE                Location/Qualifiers
misc_feature           1..51
                       note = Synthetic
source                 1..51
                       mol_type = other DNA
                       organism = synthetic construct
SEQUENCE: 51
ggtggcggag gaagcggagg cggaggatca ggtggcggtg gatctatcga t                   51

SEQ ID NO: 52          moltype = AA   length = 17
FEATURE                Location/Qualifiers
REGION                 1..17
                       note = Synthetic Construct
source                 1..17
                       mol_type = protein
                       organism = synthetic construct
SEQUENCE: 52
GGGGSGGGGS GGGGSID                                                         17

SEQ ID NO: 53          moltype = DNA   length = 60
FEATURE                Location/Qualifiers
misc_feature           1..60
                       note = Synthetic
source                 1..60
                       mol_type = other DNA
                       organism = synthetic construct
SEQUENCE: 53
agcggtaccg gcggaggtgg aagcggaggc ggaggctctg gcggcggtgg atctggatcc          60

SEQ ID NO: 54          moltype = AA   length = 20
FEATURE                Location/Qualifiers
REGION                 1..20
                       note = Synthetic Construct
source                 1..20
                       mol_type = protein
                       organism = synthetic construct
SEQUENCE: 54
SGTGGGGSGG GGSGGGGSGS                                                      20

SEQ ID NO: 55          moltype = DNA   length = 48
FEATURE                Location/Qualifiers
misc_feature           1..48
                       note = Synthetic
source                 1..48
                       mol_type = other DNA
                       organism = synthetic construct
SEQUENCE: 55
ccgcggggtg gtggttccgg cggaggtagt ggcggcggat ctgcggcc                       48

SEQ ID NO: 56          moltype = AA   length = 16
FEATURE                Location/Qualifiers
REGION                 1..16
                       note = Synthetic Construct
source                 1..16
                       mol_type = protein
                       organism = synthetic construct
```

```
SEQUENCE: 56
PRGGGSGGGS GGGSAA                                                        16

SEQ ID NO: 57           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 57
gcgtggagcc acccgcagtt cgagaaatga                                         30

SEQ ID NO: 58           moltype = AA    length = 9
FEATURE                 Location/Qualifiers
REGION                  1..9
                        note = Synthetic Construct
source                  1..9
                        mol_type = protein
                        organism = synthetic construct
SEQUENCE: 58
AWSHPQFEK                                                                 9

SEQ ID NO: 59           moltype = DNA   length = 90
FEATURE                 Location/Qualifiers
misc_feature            1..90
                        note = Synthetic
source                  1..90
                        mol_type = other DNA
                        organism = synthetic construct
SEQUENCE: 59
gcttggagcc acccgcagtt cgaaaaaggt ggaggttctg gcggtggatc gggaggttca        60
gcgtggagcc acccgcagtt cgagaaatga                                         90

SEQ ID NO: 60           moltype = AA    length = 29
FEATURE                 Location/Qualifiers
REGION                  1..29
                        note = Synthetic Construct
source                  1..29
                        mol_type = protein
                        organism = synthetic construct
SEQUENCE: 60
AWSHPQFEKG GGSGGGSGGS AWSHPQFEK                                          29

SEQ ID NO: 61           moltype = DNA   length = 21
FEATURE                 Location/Qualifiers
misc_feature            1..21
                        note = Synthetic
source                  1..21
                        mol_type = other DNA
                        organism = synthetic construct
SEQUENCE: 61
caccaccacc accaccactg a                                                  21

SEQ ID NO: 62           moltype = AA    length = 6
FEATURE                 Location/Qualifiers
REGION                  1..6
                        note = Synthetic Construct
source                  1..6
                        mol_type = protein
                        organism = synthetic construct
SEQUENCE: 62
HHHHHH                                                                    6

SEQ ID NO: 63           moltype = DNA   length = 75
FEATURE                 Location/Qualifiers
misc_feature            1..75
                        note = Synthetic
source                  1..75
                        mol_type = other DNA
                        organism = synthetic construct
SEQUENCE: 63
caccaccacc accaccacgg tggaggttct ggcggtggat cgggaggttc acatcaccat        60
caccatcacg gttga                                                         75

SEQ ID NO: 64           moltype = AA    length = 24
FEATURE                 Location/Qualifiers
REGION                  1..24
                        note = Synthetic Construct
```

```
source                  1..24
                        mol_type = protein
                        organism = synthetic construct
SEQUENCE: 64
HHHHHHGGGS GGGSGGSHHH HHHG                                              24

SEQ ID NO: 65           moltype = DNA  length = 367
FEATURE                 Location/Qualifiers
misc_feature            1..367
                        note = Synthetic
source                  1..367
                        mol_type = other DNA
                        organism = synthetic construct
SEQUENCE: 65
caagttcagc ttcaagaatc tggcggcgga agcgttcagg ctggcggatc tctgagactg        60
agctgtgtgg ccagcggcta caccgatagc acatactgcg tcggctggtt cagacaggcc      120
cctggcaaag agagagaggg cgtcgccaga atcaacacca tcagcggcag accttggtac      180
gccgactctg tgaagggcag attcacaatc agccaggaca acagcaagaa caccgtgttc      240
ctgcagatga acagcctgaa gcctgaggac accgccatct actactgcac cctgaccacc      300
gccaacagca gaggcttttg ttccggcggc tacaactaca aaggccaggg ccaagtgacc      360
gtgtctg                                                                367

SEQ ID NO: 66           moltype = AA  length = 122
FEATURE                 Location/Qualifiers
REGION                  1..122
                        note = Synthetic Construct
source                  1..122
                        mol_type = protein
                        organism = synthetic construct
SEQUENCE: 66
QVQLQESGGG SVQAGGSLRL SCVASGYTDS TYCVGWFRQA PGKEREGVAR INTISGRPWY        60
ADSVKGRFTI SQDNSKNTVF LQMNSLKPED TAIYYCTLTT ANSRGFCSGG YNYKGQGQVT      120
VS                                                                     122

SEQ ID NO: 67           moltype = DNA  length = 29811
FEATURE                 Location/Qualifiers
source                  1..29811
                        mol_type = genomic DNA
                        organism = SARS-CoV-2
SEQUENCE: 67
cttcccaggt aacaaaccaa ccaactttcg atctcttgta gatctgttct ctaaacgaac        60
tttaaaatct gtgtggctgt cactcggctg catgcttagt gcactcacgc agtataatta      120
ataactaatt actgtcgttg acaggacacg agtaactcga ctatcttctg caggctgctt      180
acggtttcgt ccgtgttgca gccgatcatc agcacatcta gtttcgtccc gggtgtgacc      240
gaaaggtaag atggagagcc ttgtccctgg tttcaacgag aaaacacacg tccaactcag      300
tttgcctgtt ttacaggttc gcgacgtgct cgtacgtggc tttggagact ccgtggagga      360
ggtcttatca gaggcacgtc aacatcttaa agatgcgact tgtgcgttag tagaagttga      420
aaaaggcgtt tgcctcaac ttgaacagcc ctatgtgttc atcaaacgtt cggatgctcg      480
aactgcacct catggtcatg ttatggttga gctggtagca gaactcgaag cattcagta      540
cggtcgtagt ggtgagacac ttggtgtcct tgtccctcat gtgggcgaaa taccagtggc      600
ttaccgcaag gttcttcttc gtaagaacgg taataaagga gctggtggcc atagttacgg      660
cgccgatcta aagtcatttg acttaggcga cgagcttggc actgatcctt atgaagattt      720
tcaagaaaac tggaacacta acatagcag tggtgttacc cgtgaactca tgcgtgagct      780
taacggaggg gcatacactc gctatgtcga taacaacttc tgtggccctg atggctaccc      840
tctttgagtgc attaaagacc ttctagcacg tgctggtaaa gcttcatgca ctttgtccga      900
acaactggac tttattgaca ctaagagggg tgtatactgc tgccgtgaac atgagcatga      960
aattgcttgg tacacggaac gttctgaaaa gagctatgaa ttcagacac cttttgaat      1020
taaattggca agaaatttg acaccttcaa tggggaatgt ccaaattttg tatttccctt      1080
aaattccata atcaagacta ttcaaccaag ggttgaaaag aaaaagcttg atggctttat      1140
gggtagaatt cgatctgtct atccagttgc gtcaccaaat gaatgcaacc aaatgtgcct      1200
ttcaactctc atgaagtgtg atcattgtgg tgaaacttca tggcagacgg gcgattttgt      1260
taaagccact tgcgaatttt gtggcactga atttgact aaagaaggtg ccactacttg      1320
tggttactta ccccaaaatg ctgttgttaa aatttattgt ccagcatgtc acaattcaga      1380
agtaggacct gagcatagtc ttgccgaata ccataatgta tctgccttga aaaccattct      1440
tcgtaagggt ggtcgcacta ttgccttttg aggctgtgtg ttctcttatg ttggttgcca      1500
taacaagtgt gcctattggg ttccacgtgc tagcgctaac ataggttgta accatacagg      1560
tgttgttgga gaaggttccg aagtcttaa tgacaacctt cttgaaatac tccaaaaaga      1620
gaaagtcaac atcaatattat ttggtgactt taaacttgat gaagatcg ccattatttt      1680
ggcatctttt tctgcttcca agtgctttt tgtgaaact gtgaaaggtt tggattataa      1740
agcattcaaa caaattgttg aatcctgtgg taatttttaa gttacaaaag gaaaagctaa      1800
aaaaggtgcc tggaatattg gtgaacagaa atcaatactg agtcctcttt atgcatttgc      1860
atcagaggct gctcgtgttg tacgatcaat ttctcccgc actcttgaaa ctgctcaaaa      1920
ttctgtgcgt gttttacaga aggccgctat aacaatacta gatggaattt cacagtattc      1980
actgagactc attgatgctg tatgttcac atctgatttg ctgttaaca atcagttgg      2040
aatggcctac attacaggtg tgttgttca gttgactcg cagtggctaa ctaacatctt      2100
tggcactgtt tatgaaaaac tcaaacccg ccttgattgg cttgaagaga gtttaagga      2160
aggtgtagag tttcttagag acggttggga aattgttaaa tttatctcaa cctgtgcttg      2220
tgaaattgtc ggtggacaaa ttgtcacctg tgcaaggaa attaaggaga gtgttcagac      2280
attctttaag cttgtaaata aatttttggc tttgtgtgct gactctatca ttattggtgg      2340
```

```
agctaaactt aaagccttga atttaggtga aacatttgtc acgcactcaa agggattgta   2400
cagaaagtgt gttaaatcca gagaagaaac tggcctactc atgcctctaa aagcccccaaa  2460
agaaattatc ttcttagagg gagaaacact tcccacagaa gtgttaacag aggaagttgt   2520
cttgaaaact ggtgatttac aaccattaga acaacctact agtgaagctg ttgaagctcc   2580
attggttggt acaccagttt gtattaacgg gcttatgttg ctcgaaatca aagacacaga   2640
aaagtactgt gcccttgcac ctaatatgat ggtaacaaac aataccttca cactcaaagg   2700
cggtgcacca acaaaggtta cttttggtga tgacactgtg atagaagtgc aaggttacaa   2760
gagtgtgaat atcacttttg aacttgatga aaggattgat aaagtactta atgagaagtg   2820
ctctgcctat acagttgaac tcggtacaga agtaaatgag ttcgcctgtg ttgtggcaga   2880
tgctgtcata aaaactttgc aaccagtatc tgaattactt acaccactgg gcattgattt   2940
agatgagtgg agtatggcta catactactt atttgatgag tctggtgagt ttaaattggc   3000
ttcacatatg tattgttctt tctaccctcc agatgaggat gaagaagaag gtgattgtga   3060
agaagaagag tttgagccat caactcaata tgagtatggt actgaagatg attaccaagg   3120
taaacctttg gaatttggtg ccacttctgc tgctcttcaa cctgaagaga agcaagaaga   3180
agattggtta gatgatgata gtcaacaaac tgttggtcaa caagacggca gtgaggacaa   3240
tcagacaact actattcaaa caattgttga ggttcaacct caattagaga tggaacttac   3300
accagttgtt cagactattg aagtgaatag ttttagtggt tatttaaaac ttactgacaa   3360
tgtatacatt aaaaatgcag acattgtgga agaagctaaa aaggtaaaac caacagtggt   3420
tgttaatgca gccaatgttt accttaaaca tggaggaggt gttgcaggag ccttaaaataa  3480
ggctactaac aatgccatgc aagttgaatc tgatgattac atagctacta atggaccact   3540
taaagtgggt ggtagttgtg ttttaagcgg acacaatctt gctaaacact gtcttcatgt   3600
tgtcggccca aatgttaaca aaggtgaaga cattcaactt cttaagagtg cttatgaaaa   3660
ttttaatcag cacgaagttc tacttgcacc attattatca gctggtattt ttggtgctga   3720
ccctatacat tctttaagag tttgtgtaga tactgttcgc acaaatgtct acttagctgt   3780
ctttgataaa aatctctatg acaaacttgt ttcaagcttt ttggaaatga agagtgaaaa   3840
gcaagttgaa caaaagatcg ctgagattcc taaagaggaa gttaagccat ttataactgaa  3900
aagtaaacct tcagttgaac agagaaaaca agatgataag aaaatcaaag cttgtgttga   3960
agaagttaca acaactctgg aagaaactaa gttcctcaca gaaaacttgt tactttatat   4020
tgacattaat ggcaatcttc atccagattc tgccactctt gttagtgaca ttgacatcac   4080
tttcttaaag aaagatgctc catatatagt gggtgatgtt gttcaagagg gtgttttaac   4140
tgctgtggtt atacctacta aaaggctgtg tggcactact gaaatgctag cgaaagcttt   4200
gagaaaagtg ccaacagaca attatataac cacttacccg ggtcagggtt taaatggtta   4260
cactgtgagg gaggcaaaga cagtgcttaa aaagtgtaaa agtgccttt acattctacc    4320
atctattatc tctaatgaga agcaagaaat tcttggaact gtttcttgga atttgcgaga   4380
aatgcttgca catgcagaag aaacacgcaa attaatgcct gtctgtgtgg aaactaaagc   4440
catagtttca actatacagc gtaaaatata gggtattaaa atacaagagg gtgtggttga   4500
ttatggtgct agattttact tttacaccag taaaacaact gtagcgtcac ttatcaacac   4560
acttaacgat ctaaatgaaa ctcttgttac aatgccactt ggctatgtaa cacatggctt   4620
aaatttggaa gaagctgctc ggtatatgag atctctcaaa gtgccagcta cagtttcgtt   4680
ttcttcacct gatgctgtta cagcgtataa tggttatctt acttcttctt ctaaaacacc   4740
tgaagaacat tttattgaaa ccatctcact tgctggttcc tataaagatt ggtcctattc   4800
tggacaatct acacaactag gtatagaatt tcttaagaga ggtgataaaa gtgtatatta   4860
cactagtaat cctaccacat tccacctaga tggtgaagtt ataccttttg acaatcttaa   4920
gacacttctt tctcttttgagag aagtgaggac tattaaggtg tttacaacag tagacaacat   4980
taacctccac acgcaagttg tggacatgtc aatgacatat ggacaacagt ttggtccaac   5040
ttatttggat ggagctgatg ttactaaaat aaaaacctcat aattcacatg aaggtaaaac   5100
attttatgtt ttacctaatg atgacactct acgtgttgag gctttttgagt actaccacac   5160
aactgatcct agttttctgg gtaggtacat gtcagcatta aatcacacta aaaagtggaa   5220
ataccacaaa gttaatggtt taacttctat taaatgggca gataacaact gttatcttgc   5280
cactgcattg ttaacactcc aacaaataga gttgaagttt aatccacctg ctctacaaga   5340
tgcttattac agagcaaggg ctggtgaagc tgctaacttt tgtgcactta tcttagcctta  5400
ctgtaataag acagtaggtg agttaggtga tgttagagaa acaatgagtt acttgttcca   5460
acatgccaat ttagattctt gcaaaagagt cttgaacgtg gtgtgtaaaa cttgtggaca   5520
acagcagaca acccttaagg gtgtagaagc tgttatgtac atgggcacac tttcttatga   5580
acaatttaag aaaggtgttc agataccttg tacgtgtggt aaacaagcta caaatatct     5640
agtacaacag gagtcacctt ttgttatgat gtcagcacca cctgctcagt atgaacttaa   5700
gcatggtaca tttacttgtg ctagtgagta cactggtaat taccagtgtg gtcactataa   5760
acatataact tctaaagaaa ctttgtattg catagacggt gctttactta caaagtcctc   5820
agaatacaaa ggtcctatta cggatgtttt ctacaaagaa aacagttaca caacaaccat   5880
aaaaccagtt acttataaat tggatggtgt tgtttgtaca gaaattgacc ctaagttgga   5940
caattattat aagaaagaca attcttattt cacagagcaa ccaattgatc ttgtaccaaa   6000
ccaaccatat ccaaacgcaa gcttcgataa ttttaagttt gtatgtgata atatcaaatt   6060
tgctgatgat ttaaaccagt taactggtta taagaaacct gcttcaagag agcttaaagt   6120
tacattttc cctgacttaa atggtgatgt ggtggctatt gattataaac actacacacc   6180
ctcttttaag aaaggagcta aattgttaca taaacctatt gtttggcatg ttaacaatgc   6240
aactaataaa gccacgtata aaccaaatac ctggtgtata cgttgtcttt ggagcacaaa   6300
accagttgaa acatcaaatt cgtttgatgt actgaagtca gaggacgcgc agggaatgga   6360
taatcttgcc tgcgaagatc taaaaccagt ctctgaagaa gtagtggaaa atcctaccat   6420
acagaaagac gttcttgagt gtaatgtgaa aactaccgaa gttgtaggaa acattatact   6480
taaaccagca aataatagtt taaaaattac agaagaggtt ggccacacag atctaatggc   6540
tgcttatgta gacaattcta gtcttactat taagaaacct aatgaattat ctagagtatt   6600
aggtttgaaa accccttgcta ctcatggttt agctgctgtt aatagtgtcc cttgggatac   6660
tatagctaat tatgctaagc ttttcttaa caaagttgtt agtacaacta ctaacatagt   6720
tacacggtgt ttaaaccgtg ttttgtactaa ttatatgcct ttttctttta cttttattgt   6780
acaattgtgt acttttacta gaagtacaaa ttctagaatt aaagcatcta tgccgactac   6840
tatagcaaag aatactgtta agagtgtcgg taaattttgt ctagaggctt catttaatta   6900
tttgaagtca cctaatttt ctaaactgat aaatattata atttggtttt tactattaag    6960
tgtttgccta ggttctttaa tctactcaac cgctgcttta ggtgttttaa tgtctaattt   7020
aggcatgcct tcttactgta ctggttacag agaaggctat ttgaactcta ctaatgtcac   7080
```

```
tattgcaacc tactgtactg gttctatacc ttgtagtgtt tgtccttagtg gtttagattc   7140
tttagacacc tatccttctt tagaaactat acaaattacc atttcatctt ttaaatggga    7200
tttaactgct tttggcttag ttgcagagtg gttttggca tatattcttt tcactaggtt     7260
tttctatgta cttggattgg ctgcaatcat gcaattgttt ttcagctatt ttgcagtaca    7320
ttttattagt aattcttggc ttatgtggtt aataattaat cttgtacaaa tggccccgat    7380
ttcagctatg gttagaatgt acatcttctt tgcatcattt tattatgtat ggaaaagtta   7440
tgtgcatgtt gtagacggtt gtaattcatc aacttgtatg atgtgttaca aacgtaatag   7500
agcaacaaga gtcgaatgta caactattgt taatggtgtt agaaggtcct tttatgtcta   7560
tgctaatgga ggtaaaggct tttgcaaact acacaattgg aattgtgtta attgtgatac   7620
attctgtgct ggtagtacat ttattagtga tgaagttgcg agagacttgt cactacagtt   7680
taaaagacca ataaatccta ctgaccagtc ttcttacatc gttgatagtg ttacagtgaa   7740
gaatggttcc atccatcttt actttgataa agctggtcaa aagacttatg aaagacattc   7800
tctctctcat tttgttaact tagacaacct gagagctaat aacactaaag gttcattgcc   7860
tattaatgtt atagtttttg atggtaaatc aaaatgtgaa gaatcatctg caaaatcagc   7920
gtctgtttac tacagtcagc ttatgtgtca acctatactg ttactagatc aggcattagt   7980
gtctgatgtt ggtgatagtg cggaagttgc agttaaaatg tttgatgctt acgttaatac   8040
gttttcatca acttttaacg taccaatgga aaaactcaaa acactagttg caactgcaga   8100
agctgaactt gcaaagaatg tgtccttaga caatgtctta tctactttta tttcagcagc   8160
tcggcaaggg tttgttgatt cagatgtaga aactaaagat gttgttgaat gtcttaaatt   8220
gtcacatcaa tctgacatag aagttactgg cgatagttgt aataactata tgctcaccta   8280
taacaaagtt gaaaacatga caccccgtga ccttggtgct tgtattgact gtagtgcgcg   8340
tcatattaat gcgcaggtag caaaaagtca caacattgct ttgatatgga cagttaaaga   8400
tttcatgtca ttgtctgaac aactacgaaa acaaatacgt agtgctgcta aaaagaataa   8460
cttacctttt aagttgacat gtgcaactac tagacaagtt gttaatgttg taacaacaaa   8520
gatagcactt aagggtggta aaattgttaa taattggttg aagcagttaa ttaaagttac   8580
acttgtgttc cttttttgttg gtgctatttt ctatttaata acacctgttc atgtcatgtc   8640
taaacatact gactttttcaa gtgaaatcat aggatacaag gctattgatg gtggtgtcac   8700
tcgtgacata gcatctacag atacttgttt tgctaacaaa catgctgatt ttgacacatg   8760
gtttagccag cgtggtggta gttatactaa tgacaaagct tgcccattga ttgctgcagt   8820
cataacaaga gaagtgggtt ttgtcgtgcc tggtttgcct ggcacgatat tacgcacaac   8880
taatggtgac tttttttgcatt tcttacctag agttttttagt gcagttggta acatctgtta   8940
cacaccatca aaacttatag agtacactga ctttgcaaca tcagcttgtg ttttggctgc   9000
tgaatgtaca attttttaaag atgcttctgg taagccagta ccatattgtt atgataccaa   9060
tgtactagaa ggttctgttg cttatgaaag tttacgccct gacacacgtt gttgctcat   9120
ggatggctct attattcaat ttcctaacac ctaccttgaa ggttctgtta gagtggtaac   9180
aactttttgat tctgagtact gtaggcacgg cacttgtgaa agatcagaag ctggtgtttg   9240
tgtatctact agtggtagat gggtacttaa caatgattat tacagatctt taccaggagt   9300
tttctgtggt gtagatgctg taaatttact tactaatatg tttacaccac taattcaacc   9360
tattggtgtc ttgacatat cagcatctat agtagctggt ggtattgtag ctatcgtagt   9420
aacatgcctt gcctactatt ttatgaggtt tagaagagct tttggtgaat acagtcatgt   9480
agttgccttc aatactttac tattccttat gtcattcact gtactctgtt aacaccagt    9540
ttactcattc ttacctggtg tttattctgt tatttacttg tacttgacat tttatcttac   9600
taatgattt tcttttttag cacatattca gtggatggtt atgttcacac ctttagtacc   9660
tttctggata acaattgctt atatcatttg tatttccaca aagcatttct attggttctt   9720
tagtaattac ctaaagagac gtgtagtctt taatggtgtt tcctttagta ctttttgaaga   9780
agctgcgctg tgcaccttttt tgttaaataa agaaatgtat ctaaagttgc gtagtgatgt   9840
gctattacct cttacgcaat ataatagata cttagctctt tataataagt acaagtattt   9900
tagtggagca atggatacaa ctagctacag agaagctgct tgttgtcatc tcgcaaaggc   9960
tctcaatgac ttcagtaact caggttctga tgttcttttac caaccaccac aaacctctat   10020
cacctcagct gttttgcaga gtggttttag aaaaatggca ttcccatctg gtaaagttga   10080
gggttgtatg gtacaagtaa cttgtggtac aactacactt aacggtcttt ggcttgtga    10140
cgtagtttac tgtccaagac atgtgatctg cacctctgaa gacatgctta accctaatta   10200
tgaagattta ctcattcgta agtctaatca atttcttgt gtacaggctg gtaatgttca    10260
actcaggtt attggacatt ctatgcaaaa ttgtgtactt aagcttaagg ttgatacagc   10320
caatcctaag acacctaagt ataagtttgt tcgcattcaa ccaggacaga cttttttcagt   10380
gttagcttgt tacaatggtt caccatctgg tgttttaccaa tgtgctatga ggcccaatttt  10440
cactattaag ggttcattcc ttaatggttc atgtggtagt gttggtttta cattaagatta  10500
tgactgtgtc tcttttttgtt acatgcacca tatggaatta ccaactggag ttcatgctgg  10560
cacagactta gaaggtaact tttatgtgacc ttttttgttgac aggcaaacag cacaagcagc  10620
tggtacggac acaactatta cagttgaatgt tttagcttgg ttgtacgctg ctgtttataaa   10680
tggagacagg tggttttctca atcgattttac cacaactctt aatgacttta accttgtggc   10740
tatgaagtac aattatgaac ctctaacaca agaccatgtt gacatactag gacctctttc   10800
tgctcaaact ggaattgccg ttttagatat gtgtgctcca ttaaaagaat tactgcaaaa   10860
tggtatgaat ggacgtacca tattgggtag tgcttttatta gaagatgaat ttacacccttt  10920
tgatgttgtt agacaatgct caggtgttac tttccaaagt gcagtgaaaa gaacaatcaa    10980
gggtacacac cactgttgt tactcacaat tttgacttca cttttagttt tagtccagag    11040
tactcaatgg tctttgttct tttttttgta tgaaaatgcc ttttacctt ttgctatggg     11100
tattattgct atgtctgctt ttgcaatgat gtttgtcaaa cataagcatg catttctctg    11160
tttgttttttg ttaccttctc ttgccactgt agcttattt aatatggctt atatgcctgc    11220
tagttgggtg atgcgtatta tgacatggtt ggatatggtt gatactagtt tgtctggttt    11280
taagctaaaa gactgtgtta tgtatgcatc actgtagtg ttactaatcc ttatgacagc    11340
aagaactgtg tatgatgatg gtgtgctagg agtgtggaca cttgttgaatg tcttgacact   11400
cgttatataaa gttattatg taatgcttt agatcaagcc atttccatgt gggctctttat   11460
aatctctgtt acttctaact actcaggtgt agttaaccat catgttttt ggccagagg    11520
tattgttttttt atgtgtcttg tgtatatttctc ataactggta atacttctta gtgtttttct  11580
gtgtataatgc ctagtttatt gtttcttagg ctattttgt acttgttact ttggcctctt   11640
ttgtttactc aaccgctact ttagactgac tcttggtgtt tatgattact agttttctac    11700
acaggagttt agatatatga attcacaggg actactccca cccaagaata gcatagatgc   11760
cttcaaactc aacattaaat tgttgggtgt tggtggcaaa cctttgtatca aagtagccac   11820
```

```
tgtacagtct aaaatgtcag atgtaaagtg cacatcagta gtcttactct cagttttgca   11880
acaactcaga gtagaatcat catctaaatt gtgggctcaa tgtgtccagt tacacaatga   11940
cattctctta gctaaagata ctactgaagc ctttgaaaaa atggtttcac tactttctgt   12000
tttgctttcc atgcagggtg ctgtagacat aaacaagctt tgtgaagaaa tgctggacaa   12060
cagggcaacc ttacaagcta tagcctcaga gtttagttcc cttccatcat atgcagcttt   12120
tgctactgct caagaagctt atgagcaggc tgttgctaat ggtgattctg aagttgttct   12180
taaaaagttg aagaagtctt tgaatgtggc taaatctgaa tttgaccgtg atgcagccat   12240
gcaacgtaag ttggaaaaga tggctgatca agctatgacc caaatgtata aacaggctag   12300
atctgaggac aagagggcaa aagttactag tgctatgcaa acaatgcttt tcactatgct   12360
tagaaagttg gataatgatg cactcaacaa cattatcaac aatgcaagag atggttgtgt   12420
tcccttgaac ataatacctc ttacaacagc agccaaacta atggttgtca taccagacta   12480
taacacatat aaaaatacgt gtgatggtac aacatttact tatgcatcag cattgtggga   12540
aatccaacag gttgtagatg cagatagtaa aattgttcaa cttagtgaaa ttagtatgga   12600
caattcacct aatttagcat ggcctcttat tgtaacagct ttaagggcca attctgctgt   12660
caaattcagt aataatgagc ttagtcctgt tgcactacga cagatgtctt gtgctgccgg   12720
tactacacaa actgcttgca ctgatgacaa tgcgttagct tactacaaca caacaaaggg   12780
aggtaggttt gtacttgcac tgttatccga tttacaggat ttgaaatggg ctagattccc   12840
taagagtgat ggaactggta ctatctatac agaactggaa ccaccttgta ggtttgttac   12900
agacacacct aaaggtccta aagtgaagta tttatacttt attaaaggat taaacaacct   12960
aaatagaggt atggtacttg gtagtttagc tgccacagta cgtctacaag ctggtaatgc   13020
aacagaagtg cctgccaatt caactgtatt atctttctgt gcttttgctg tagatgctgc   13080
taaagcttac aaagattatc tagctagtgg gggacaacca atcactaatt gtgttaagat   13140
gttgtgtaca cacactggta ctggtcaggc aataacagtt acaccggaag ccaatatgga   13200
tcaagaatcc tttggtggtg catcgtgttg tctgtactgc cgttgccaca tagatcatcc   13260
aaatcctaaa ggattttgtg acttaaaagg taagtatgta caaatcccta acttgtgc    13320
taatgaccct gtgggtttta cacttaaaaa cacagtctgt accgtctgcg gtatgtggaa   13380
aggttatggc tgtagttgtg atcaactccg cgaaccatg cttcagtcag ctgatgcaca    13440
atcgttttta aacgggtttg cggtgtaagt gcagcccgtc ttacaccgtg cggcacaggc   13500
actagtactg atgtcgtata cagggctttt gacatctaca atgataaagt agctggtttt   13560
gctaaattcc taaaaactaa ttgtgtcgc ttccaagaaa aggacgaaga tgacaattta    13620
attgattctt actttgtagt taagagacac actttctcta actaccaaca tgaagaaaca   13680
atttataatt tacttaagga ttgtccagct gttgctaaac atgactttt taagtttaga    13740
atagacggta catggtacc acatatatca cgtcaacgtc ttactaaata cacaatggca   13800
gacctcgtct atgcttttaag gcattttgat gaaggtgtca tgtgacactt aaaaagaata   13860
cttgtcacat acaattgttg tgatgatgat tatttcaata aaaaggactg gtatgatttt   13920
gtagaaaacc cagatatatt acgcgtatac gccaacttag gtgaacgtgt acgcaagct    13980
ttgttaaaaa cagtacaatt ctgtgatgcc atgcgaaatg ctggtattgt tggtgtactg   14040
acattagata atcaagatct caatggtaac tggtatgatt tcggtgattt catacaaacc   14100
acgccaggta gtgagttcc tgttgtagat tcttatatt cattgttaat gcctatatta    14160
accttgacca gggctttaac tgcagagtca catgttgaca ctgacttaac aaagccttac   14220
attaagtggg atttgttaaa atgacttc acggaagaga ggtaaaaact ctttgaccgt    14280
tatttaaat attgggatca gacataccac ccaaattgtg ttaactgttt ggatgacaga   14340
tgcattctgc attgtgcaaa ctttaatgtt ttattctca cagtgttccc acctacaagt    14400
tttggaccac tagtgagaaa aatatttgtt gatggtgttc catttgtagt ttcaactgga   14460
taccacttca gagagctagg tgttgtacat aatcaggatg taaacttaca tagctctaga   14520
cttagtttta aggaattact tgtgtatgct gctgaccctg ctatgcacgc tgcttctggt   14580
aatctattac tagataaacg cactacgtgc ttttcagtag ctgcacttac taacaatgtt   14640
gcttttcaaa ctgtcaaacc cggtaatttt aacaaagact tctatgactt tgctgtgtct   14700
aaggggtttct ttaaggaagg aagttctgtt gaattaaaac acttcttctt tgctcaggat   14760
ggtaatgctg ctatcagcga ttatgactac tatcgttata atcctaccaac aatgtgtgat   14820
atcagacaac tactatttgt agttgaagtt gttgataagt actttgattg ttacgatggt   14880
ggctgtatta atgctaacca agtcatcgtc aacaacctag acaaatcagc tggttttcca   14940
tttaataaat ggggtaaggc tagacttat tatgattcaa tgagttatga ggatcaagat   15000
gcacttttcg catatacaaa acgtaatgtc atccctacta taactcaaat gaatcttaag   15060
tatgccatta gtgcaaagaa tagagctcgc accgtagctg gtgtctctat ctgtagtact   15120
atgaccaata cacagtttca tcaaaaatta ttgaaatcaa tagccgccac tagaggagct   15180
actgtagtaa ttggaacaag caaattctat ggtggttggc acaacatgtt aaaaactgtt   15240
tatagtgatg tagaaaaccc tcaccttatg ggttgggatt atcctaaatg tgatagagcc   15300
atgcctaaca tgcttagaat tatggcctca cttgttcttg ctcgcaaaca tacaacgtgt   15360
tgtagcttgt cacaccgttt ctatagatta gctaatgagt gtgctcaagt attgagtgaa   15420
atggtcatgt gtggcggttc actatatgtt aaaccaggtg gaacctcatc aggagatgcc   15480
acaactgctt atgctaatag tgttttttaac atttgtcaag ctgtcacggc caatgttaat   15540
gcactttat ctactgatgg taacaaaatt gccgataagt atgtccgcaa tttacaacac   15600
agactttatg agtgtctcta tagaaataga cagttgtgca gcttttgt gaatgagttt   15660
tacgcatatt tgcgtaaaca tttctcaatg atgatactct ctgacgatgc tgttgtgtgt   15720
ttcaatagca cttatgcatc tcaaggtcta gtggctagca taaagaactt aagtcagtt    15780
ctttattatc aaaacaatgt ttttatgtct gaagcaaaat gttggactga gactgacctt   15840
actaaaggac ctcatgaatt ttgctctcaa catacaatgc tagttaaaca gggtgatgat   15900
tatgtgtacc ttccttaccc agatccatca agaatcctag gggccggctg ttttgtagat   15960
gatatcgtaa aaacagatgg tacacttatg attgaacggt tcgtgtcttt agctatagat   16020
gcttacccac ttactaaaca tcctaatcag gagtatgctg atgtctttca tttgtactta   16080
caatacataa gaaagctaca tgatgagtta acaggacaca tgttagacat gtattctgtt   16140
atgcttacta atgataacac ttcaaggtat tgggaacctga gttttatga ggctatgtac   16200
acaccgcata cagtcttaca gtgtgttggg gcttgtgttt tgtgcaattc acagacttca   16260
ttaagatgtg gtgcttgcat acgtagacca ttcttatgtt gtaaatgctg ttacgaccat   16320
gtcatatcaa catcacataa attagtcttg tctgttaatc cgtatgtttg caatgctcca   16380
ggttgtgatg tcagagatgt gactcaactt tacttaggag gtatgagcta ttattgtaaa   16440
tcacataaac caccattag tttttccattg tgtgctaatg acaagttt tggtttatat   16500
aaaaatacat gtgttggtag cgataatgtt actgacttta atgcaattgc aacatgtgac   16560
```

```
tggacaaatg ctggtgatta cattttagct aacacctgta ctgaaagact caagctttt   16620
gcagcagaaa cgctcaaagc tactgaggag acatttaaac tgtcttatgg tattgctact   16680
gtacgtgaag tgctgtctga cagagaatta catctttcat gggaagttgg taaacctaga   16740
ccaccactta accgaaatta tgtctttact ggttatcgtg taactaaaaa cagtaaagta   16800
caaataggag agtacacctt tgaaaaaggt gactatggtg atgctgttgt ttaccgaggt   16860
acaacaactt acaaattaaa tgttggtgat tattttgtgc tgacatcaca tacagtaatg   16920
ccattaagtg cacctacact agtgccacaa gagcactatg ttagaattac tggcttatac   16980
ccaacactca atatctcaga tgagttttct agcaatgttg caaattatca aaaggttggt   17040
atgcaaaagt attctacact ccagggacca cctggtactg gtaagagtca ttttgctatt   17100
ggcctagctc tctactaccc ttctgctcgc atagtgtata cagcttgctc tcatgccgct   17160
gttgatgcac tatgtgagaa ggcattaaaa tatttgccta tagataaatg tagtagaatt   17220
atacctgcac gtgctcgtgt agagtgtttt gataaattca aagtgaattc aacattagaa   17280
cagtatgtct tttgtactgt aaatgcattg cctgagacga cagcagatat agttgtcttt   17340
gatgaaattt caatggccac aaattatgat ttgagtgttg tcaatgccag attacgtgct   17400
aagcactatg tgtacattgg cgaccctgct caattacctg caccacgcac attgctaact   17460
aagggcacac tagaaccaga atatttcaat tcagtgtgta gacttatgaa actataggt    17520
ccagacatgt tcctcggaac ttgtcggcgt tgtcctgctg aaattgttga cactgtgagt   17580
gctttggttt atgataataa gctaaagca cataaagaca aatcagctca atgcttaaa     17640
atgttttata agggtgttat cacgcatgat gtttcatctg caattaacag cccacaaata   17700
ggcgtggtaa gagaattcct tacacgtaac cctgcttgga gaaaagctgt ctttatttca   17760
ccttataatt cacagaatgc tgtagcctca aagattttgg gactaccaac tcaaactgtt   17820
gattcatcac agggctcaga atatgactat gtcatattca ctcaaaccac tgaaacagct   17880
cactcttgta atgtaaacag atttaatgtt gctattacca gagcaaaagt aggcatactt   17940
tgcataatgt ctgatagaga cctttatgac aagttgcaat ttacaagtct tgaaattcca   18000
cgtaggaatg tggcaacttt acaagctgaa aatgtaacag gactctttaa agattgtagt   18060
aaggtaatca ctgggttaca tcctacacag gcacctacac acctcagtgt tgacactaaa   18120
ttcaaaactg aaggtttatg tgttgacata cctggcatac taaggacat gacctataga    18180
agactcatct ctatgatggg ttttaaaatg aattatcaag ttaatggtta ccctaacatg   18240
tttatcaccc gcgaagaagc tataagacat gtacgtgcat ggattggctt cgatgtcgag   18300
gggtgtcatg ctactagaga agctgttggt accaatttac ctttacagct aggtttttct   18360
acaggtgtta acctagttgc tgtacctaca ggttatgttg atacacctaa taatacagat   18420
ttttccagag ttagtgctaa accaccgcct ggagatcaat ttaaacacct cataccactt   18480
atgtacaaag gacttccttg gaatgtagtg cgtataaaga ttgtacaaat gttaagtgac   18540
acacttaaaa atctctctga cagagtcgta tttgtcttat gggcacatgg ctttgagttg   18600
acatctatga gtatttttgt gaaaatagga cctgagcgca cctgttgtct atgtgataga   18660
cgtgccacat gcttttccac tgcttcgaca acttatgcct gttggcatca ttctattgga   18720
tttgattacg tctataatcc gtttatgatt gatgttcaac aatgggggtt tacaggtaac   18780
ctacaaagca accatgatct gtattgtcaa gtccatggta atgcacatgt agctagtgt    18840
gatgcaatca tgactaggtg tctagctgtc cacgagtgct ttgttaagcg tgttgactgg   18900
actattgaat atccctataat tggtgatgaa ctgaagatta tgcggcttg tagaaaggtt    18960
caaacacatg ttgttaaagc tgcattatta gcagacaaat tcccagtct tcacgacatt    19020
ggtaacccta aagctattaa gtgtgtacct caagctgatg tagaatggaa gttctatgat    19080
gcacagcctt gtagtgacaa agcttataaa atagaagaat tattctatte ttatgccaca   19140
cattctgaca aattcacaga tggtgtatgc ctatttggg attgcaatgt cgatagatat   19200
cctgctaatt ccattgtttg tagatttgac actagagtgc tatctaacct taacttgcct   19260
ggttgtgatg gtggcagttt gtatgtaaat aaacatgcat tccacacacc agcttttgat   19320
aaaagtgctt ttgttaattt aaaacaaatta ccattctga cagtccatg                19380
gagtctcatg gaaaacaagt agtgtcagat ataagattatg taccactaaa gtctgctacg   19440
tgtataacac gttgcaattt aggtggtgct gtctgtagac atcatgctaa tgagtacaga   19500
ttgtatctcg atgcttataa catgatgatc tcagctggct ttagcttgtg ggtttacaaa   19560
caatttgata cttataacct ctggaacact tttacaagac ttcagagttt agaaaatgtg   19620
gcttttaatg ttgtaaataa gggacacttt gatggacaac agggtgaagt accagtttct   19680
atcattaata acactgtta cacaaaagtt gatggtgttg atgtagaatt gtttgaaaat   19740
aaaacaacat tacctgttaa tgtagcattt gagctttggg ctaagcgcaa cattaaacca   19800
gtaccagagg tgaaaatact caataatttg ggtgtggaca ttgctgctaa tactgtgatc   19860
tgggactaca aaagagatgc tccagcacat atatctacta ttggtgtttg ttctatgact   19920
gacatagcca agaaccaac tgaaacgatt tgtgcaccac tcactgtctt ttttgatggt   19980
agagttgatg gtcaagtaga cttatttaga aatgcccgta atggtgttct tattacagaa   20040
ggtagtgtta aggtttaca accatcgtta ggtcccaaac aagctagtct taatggagtc   20100
acattaattg gagaagccgt aaaaacacag ttcaattatt ataagaaagt tgatggtgtt   20160
gtccaacaat tacctgaaac ttactttact cagagtagaa atttacaaga atttaaaccc   20220
aggagtcaaa tggaaattga tttcttagaa ttagctatgg atgaattcat tgaacggtat   20280
aaattagaag gctatgcctt cgaacatatc gtttatggag attttagtca tagtcagtta   20340
ggtggtttac atctactgat tggactagct aaacgtttta aggaaccctt ttgaatta    20400
gaagattta ttcctatgga cagtacagtt aaaaactatt tcataacaga tgcgcaaaca   20460
ggttcatcta gtgtgtgtg ttctgttatt gattattac ttgatgattt tgttgaaata    20520
ataaaatccc aagatttatc tgtagtttct aaggttgtca aagtgactat tgactataca   20580
gaaattcat ttatgctttg gtgtaaagat ggccatgtag aaacatttc cccaaaatta     20640
caatcagtc aagcgtggca accgggtgtt gctatgccta atcttacaa aatgcaaaga   20700
atgctattag aaaagtgtga ccttcaaaat tatggtgata gtgcaacatt acctaaaggc   20760
ataatgatga atgtcgcaaa atatactcaa ctgtgtcaat atttaaacac attaacatta   20820
gctgtaccct ataatatgag agttatacat tttggtgctg ttctgataa aggagttgca   20880
ccaggtacag ctgttttaag acagtggttg cctacgggta cgctgcttgt cgattcagat   20940
cttaatgact tgtctctga tgcagattca actttgattg gtgattgtgc aactgtacat   21000
acagctaata aatgggatct cattattagt gatatgtacg accctaagac taaaaatgtat   21060
acaaagaaa atgactctaa agaggggtttt tcacttaca tttgtggtt tatacaacaa    21120
aagctagctc ttgagggttc cgtggctata agataacag aacattcttg gaatgctgat   21180
ctttataagc tcatgggaca cttcgcatgg tggacagcct tgttactaa tgtgaatgcg    21240
tcatcatctg aagcattttt aattggatgt aattatcttg gcaaaccacg cgaacaaata   21300
```

```
gatggttatg tcatgcatgc aaattacata ttttggagga atacaaatcc aattcagttg   21360
tcttcctatt ctttatttga catgagtaaa tttcccctta aattaagggg tactgctgtt   21420
atgtctttaa aagaaggtca aatcaatgat atgattttat ctcttcttag taaaggtaga   21480
cttataatta gagaaaacaa cagagttgtt atttctagtg atgttcttgt taacaactaa   21540
acgaacaatg tttgtttttc ttgttttatt gccactgtc tctagtcagt gtgttaatct   21600
tacaaccaga actcaattac cccctgcata cactaattct ttcacacgtg gtgtttatta   21660
ccctgacaaa gttttcagat cctcagtttt acattcaact caggacttgt tcttaccttt   21720
cttttccaat gttacttggt tccatgctat acatgtctct gggaccaatg gtactaagag   21780
gtttgataac cctgtcctac catttaatga tggtgtttat tttgcttcca ctgagaagtc   21840
taacataata agaggctgga ttttggtac tacttagat tcgaagaccc agtccctact   21900
tattgttaat aacgctacta atgttgttat taaagtctgt gaatttcaat tttgtaatga   21960
tccattttg ggtgtttatt accacaaaaa caacaaaagt tggatggaaa gtgagttcag   22020
agtttattct agtgcgaata attgcacttt tgaatatgtc tctcagcctt ttcttatgga   22080
ccttgaagga aaacagggta attttcaaaaa tcttaggtga tttgtgttta agaatattga   22140
tggttatttt aaaatatatt ctaagcacac gccttataat ttagtgcgtg atctccctca   22200
gggtttttcg gctttagaac cattggtaga tttgccaata ggtattaaca tcactaggtt   22260
tcaaactta cttgctttac atagaagtta tttgactcct ggtgattctt cttcaggttg   22320
gacagctggt gctgcagcgt attatgtggg ttatcttcaa cctaggactt ttctattaaa   22380
atataatgaa aatggaacca ttacagatgc tgtagactgt gcacttgacc ctctctcaga   22440
aacaaagtgt acgttgaaat ccttcactgt agaaaaagga atctatcaaa cttctaactt   22500
tagagtccaa ccaacagaat ctattgttag atttcctaat attacaaact gtgcccttt    22560
tggtgaagtt tttaacgcca ccagatttgc atctgtttat gcttggaaca ggaagagaat   22620
cagcaactgt gttgctgatt attctgtcct atataattcc gcatcatttt ccacttttaa   22680
gtgttatgga gtgtctccta ctaaattaaa tgatctctgc tttactaatg tctatgcaga   22740
ttcatttgta attagaggtg atgaagtcag acaaatcgct ccagggcaaa ctggaaagat   22800
tgctgattat aattataaat taccagatga ttttacaggc tgcgttatag cttggaattc   22860
taacaatctt gattctaagg ttggtggtaa ttataattac ctgtatagat tgtttaggaa   22920
gtctaatctc aaacctttg agagagatat ttcaactgaa atctatcagg ccggtagcac   22980
accttgtaat ggtgttgaag gttttaattg ttactttcct ttacaatcat atggtttcca   23040
acccactaat ggtgttggtt accaaccata cagagtagta gtactttctt ttgaacttct   23100
acatgcacca gcaactgttt gtggacctaa aaagtctact aatttggtta aaaacaaatg   23160
tgtcaatttc aacttcaatg gtttaacagg cacaggtgtt cttactgagt ctaacaaaaa   23220
gtttctgcct ttccaacaat tggcagagac attgctgac actactgatg ctgtccgtga   23280
tccacagaca cttgagattc ttgacattac accatgttct tttggtggtg tcagtgttat   23340
aacaccagga acaaatactt ctaaccaggt tgctgttctt tatcaggatg ttaactgcac   23400
agaagtccct gttgctattc atgcagatca acttactcct acttggctgt tttattctac   23460
aggttctaat gtttttcaaa cacgtgcagg ctgtttaata ggggctgaac atgtcaacaa   23520
ctcatatgag tgtgacatac ccattggtgc aggtatatgc gctagttatc agactcagac   23580
taattctcct cggcgggcac gtagtgtagc tagtcaatcc atcattgcct acactatgtc   23640
acttggtgca gaaaattcag ttgcttactc taataactct attgccatac ccacaaattt   23700
tactattagt gttaccacag aaattctacc agtgtctatg accaagacat cagtagattg   23760
tacaatgtac atttgtggtg attcaactga atgcagcaat cttttgttgc aatatggcag   23820
tttttgtaca caattaaacc gtgctttaac tggaatagct gttgaacagg acaaaaacac   23880
ccaagaagtt tttgcacaag tcaaacaaat ttacaaaaca ccaccaatta agattttgg    23940
tggttttaat ttttcacaaa tattaccaga tccatcaaaa ccaagcaaga ggtcatttat   24000
tgaagatcta ctttcaata aagtgacact tgcagatgct ggcttcatca acaatatgg    24060
tgattgcctt ggtgatattg ctgctagaga cctcatttgt gcacaaaagt ttaacggcct   24120
tactgttttg ccacctttgc tcacagatga aatgattgct caatacactt ctgcactgtt   24180
agcgggtaca atcacttctg gttggacctt tggtgcaggt gctgcattac aaataccatt   24240
tgctatgcaa atggcttata ggtttaatgg tattggagtt acacagaatg ttctctatga   24300
gaaccaaaaa ttgattgcca accaatttaa tagtgctatt ggcaaaattc aagactcact   24360
ttcttccaca gcaagtgcac ttggaaaact tcaagatgtg gtcaaccaaa atgcacaagc   24420
tttaaacacg cttgttaaac aacttagctc caattttggt gcaatttcaa gtgttttaaa   24480
tgatatcctt tcacgtcttg acaaagttga ggctgaagtg caaattgata ggttgatcac   24540
aggcagactt caaagtttgc agacatatgt gactcaacaa ttaattagag ctgcagaaat   24600
cagagcttct gctaatcttg ctgctactaa aatgtcagag tgtgtacttg acaatcaaa    24660
aagagttgat ttttgtggaa agggctatca tcttatgtcc ttccctcagt cagcacctca   24720
tggtgtagtc ttcttgcatg tgacttatgt ccctgcacaa gaaaagaact tcacaactgc   24780
tcctgccatt tgtcatgatg gaaaagcaca ctttcctcgt gaaggtgtct ttgtttcaaa   24840
tggcacacac tggtttgtaa cacaaaggaa ttttatgaa ccacaaatca ttactacaga   24900
caacacattt gtgtctggta actgtgatgt tgtaatagga attgtcaaca acacagttta   24960
tgatccttg caacctgaat tagactcatt caaggaggag ttagataaat attttaagaa   25020
tcatacatca ccagatgttg attaggtga catctctggc attaatgctt cagttgtaaa   25080
cattcaaaaa gaaattgacc gcctcaatga ggttgccaag aatttaaatg aatctctcat   25140
cgatctccaa gaacttggaa agtatgagca gtatataaaa tggccatggt acatttggct   25200
aggttttata gctggcttga ttgccatagt aatggtgaca attatgcttt gctgtatgac   25260
cagttgctgt agttgtctca agggctgttg ttcttgtgga tcctgctgca aatttgatga   25320
agacgactct gagccagtgc tcaaaggagt caaattacat tacacataaa cgaacttatg   25380
gatttgttta tgagaatctt cacaattgga actgtaactt tgaagcaagg tgaaatcaag   25440
gatgctactc cttcagattt tgttcgcgct actgcaacga taccgataca gcctcactc    25500
cctttcggat ggcttattgt tggcgttgca cttcttgctg tttttcagag cgcttccaaa   25560
atcataaccc tcaaaagag atggcaacta gcactctcca gggtgttca ctttgtttgc    25620
aacttgctgt tgttgtttgt aacagtttac tcacaccttt gctcgttgc tgctggcctt   25680
gaagccccct tctctatct ttatgcttta gtctagagtat tcagagtat aactttgta   25740
agaataataa tgaggctttg gctttgctgg aaatgccgtt ccaaaaaccc attactttat   25800
gatgccaact atttttcttg ctggcatact aattgttacg actattgtat accttacaat   25860
agtgtaactt cttcaattgt cattacttca ggtgatggca caacaagtcc tatttctgaa   25920
catgactacc agattggtgg ttatactgaa aaatgggaat ctgagtaaa agactgtgtt    25980
gtattacaca gttacttcac ttcagactat taccagctgt actcaactca attgagtaca   26040
```

```
gacactggtg ttgaacatgt taccttcttc atctacaata aaattgttga tgagcctgaa  26100
gaacatgtcc aaattcacac aatcgacggt tcatccggag ttgttaatcc agtaatggaa  26160
ccaatttatg atgaaccgac gacgactact agcgtgcctt tgtaagcaca agctgatgag  26220
tacgaactta tgtactcatt cgtttcggaa gagacaggta cgttaatagt taatagcgta  26280
cttcttttc ttgctttcgt ggtattcttg ctagttacac tagccatcct tactgcgctt  26340
cgattgtgtg cgtactgctg caatattgtt aacgtgagtc ttgtaaaacc ttctttttac  26400
gtttactctc gtgttaaaaa tctgaattct tctagagttc ctgatcttct ggtctaaacg  26460
aactaaaatat tatattagtt tttctgtttg gaactttaat tttagccatg gcagattcca  26520
acggtactat taccgttgaa gagcttaaaa agctccttga acaatggaac ctagtaatag  26580
gtttcctatt ccttacatgg atttgtcttc tacaatttgc ctatgccaac aggaataggt  26640
ttttgtatat aattaagtta attttcctct ggctgttatg gccagtaact ttagcttgtt  26700
ttgtgcttgc tgctgtttac agaataaatt ggatcaccgg tggaattgct atcgcaatgg  26760
cttgtcttgt aggcttgatg tggctcagct acttcattgc ttctttcaga ctgtttgcgc  26820
gtacgcgttc catgtggtca ttcaatccag aaactaacat tcttctcaac gtgccactcc  26880
atggcactat tctgaccaga ccgcttctag aaagtgaact cgtaatcgga gctgtgatcc  26940
ttcgtggaca tcttcgtatt gctggacacc atctaggacg ctgtgacatc aaggacctgc  27000
ctaaagaaat cactgttgct acatcacgaa cgctttctta ttacaaattg ggagcttcgc  27060
agcgtgtagc aggtgactca ggtttgctg catacagtcg cataggtagg gcaactata  27120
aattaaacac agaccattcc agtagcagtg acaatattgc tttgcttgta cagtaagtga  27180
caacagatgt ttcatctcgt tgactttcag gttactatag cagagatatt actaattatt  27240
atgaggactt ttaaagttc catttggaat cttgattaca tcataaacct cataattaaa  27300
aatttatcta agtcactaac tgagaataaa tattctcaat tatatgaaga gacaaccaatg  27360
gagattgatt aaacgaacat gaaaattatt cttttcttgg cactgataac actcgctact  27420
tgtgagcttt atcactacca agagtgtgtt agaggtacaa cagtactttt aaaagaacct  27480
tgctcttctg gaacatacga gggcaattca ccatttcatc ctctagctga taacaaattt  27540
gcactgactt gctttagcac tcaatttgct tttgcttgtc ctgacggcgt aaaacagtc  27600
tatcagttac gtgccagatc agtttcaccc aaactgttca tcagacaaga ggaagttcaa  27660
gaactttact ctccaatttt tcttattgtt gcggcaatag tgtttataac actttgcttc  27720
acactcaaaa gaaagacaga atgattgaac tttcattaat tgacttctat ttgtgctttt  27780
tagccttct gctattcctt gttttaatta tgcttattat cttttggttc tcacttgaac  27840
tgcaagatca taatgaaact tgtcacgcct aaacgaacat gaaatttctt gttttcttag  27900
gaatcatcac aactgtagct gcatttcacc aagaatgtag tttacagtca tgtactcaac  27960
atcaaccata tgtagttgat gacccgtgtc ctattcactt ctattctaaa tggtatatta  28020
gagtaggagc tagaaaatca gcaccttttaa ttgaattgtg cgtggatgag gctggttcta  28080
aatcacccat tcagtacatc gatatcggta attatacagt ttcctgttta ccttttacaa  28140
ttaattgcca ggaacctaaa ttgggtagtc ttgtagtgcg ttgttcgttc tatgaagact  28200
ttttagagta tcatgacgtt cgtgttgttt tagatttcat ctaaacgaac aaactaaaat  28260
gtctgataat ggaccccaaa atcagcgaaa tgcacccccgc attacgtttg gtggaccctc  28320
agattcaact ggcagtaacc agaatggaga acgcagtggg gcgcgatcaa aacaacgtcg  28380
gccccaaggt ttacccaata atactgcgtc ttggttcacc gctctcactc aacatggcaa  28440
ggaagacctt aaattccctc gaggacaagg cgttccaatt aacaccaata gcagtccaga  28500
tgaccaaatt ggctactacc gaagagctac cagacgaatt cgtggtggtg acggtaaaat  28560
gaaagatctc agtccaagat ggtatttcta ctacctagga aagctggact  28620
tccctatggt gctaacaaag acggcatcat atgggttgca actgagggag ccttgaatac  28680
accaaaagat cacattggca cccgcaatcc tgctaacaat gctgcaatcg tgctacaact  28740
tcctcaagga acaacattgc caaaggcttc ctacgcagaa gggagcagag gcggcagtca  28800
agcctcttct cgttcctcat cacgtagtcg caacagttca agaaattcaa ctccaggcag  28860
cagtagggga acttctcctg ctagaatggc tggcaatggc ggtgatgctg ctcttgcttt  28920
gctgctgctt gacagattga accagcttga gagcaaaatg tctggtaaag gccaacaaca  28980
acaaggccaa actgtcacta agaaatctgc tgctgaggct tctaagaagc ctcggcaaaa  29040
acgtactgcc actaaagcat acaatgtaac acaagctttc ggcagacgtg gtccagaaca  29100
aacccaagga aattttgggg accaggaact aatcagacaa ggaactgatt acaaacattg  29160
gccgcaaatt gcacaatttg cccccagcgc ttcagcgttc ttcggaatgt cgcgcattgg  29220
catgaagtc acaccttcgg gaacgtggtt gacctacaca ggtgccatca aattggatga  29280
caaagatcca aatttcaaag atcaagtcat tttgctgaat aagcatattg acgcatacaa  29340
aacattccca ccaacagagc ctaaaaagga caaaagaag aaggctgatg aaactcaagc  29400
cttaccgcag agacagaaga aacagcaaac tgtgactctt cttcctgctg cagatttgga  29460
tgatttctcc aaacaattgc aacaatccat gagcagtgct gactcaactc aggcctaaac  29520
tcatgcagac cacacaaggc agatgggcta tataaacgtt ttcgctttc cgtttacgat  29580
atatagtcta ctcttgtgca gaatgaattc tcgtaactac atagcacaag tagatgtagt  29640
taactttaat ctcacatagc aatctttaat cagtgtgtaa cattagggag gacttgaaag  29700
agccaccaca ttttcaccga ggccacgcgg agtacgatcg agtgtacagt gaacaatgct  29760
agggagagct gcctatatgg aagagcccta atgtgtaaaa ttaattttag t  29811
```

RAPID ASSAY FOR DETECTION OF SARS-CoV-2 ANTIBODIES

CROSS REFERENCE TO RELATED APPLICATIONS

This application is a continuation of U.S. patent application Ser. No. 17/478,527, filed Sep. 17, 2021, which is a divisional of U.S. patent application Ser. No. 17/140,321, filed on Jan. 4, 2021, now U.S. Pat. No. 11,175,293, each of which is incorporated by reference herein in its entirety.

REFERENCE TO SEQUENCE LISTING

This application was filed with a Sequence Listing XML in ST.26 XML format in accordance with 37 C.F.R. § 1.821. The Sequence Listing XML file submitted in the USPTO Patent Center, "026389-9305-US03_sequence_listing_xml_22-SEP-2022.xml," was created on Sep. 22, 2022, contains 67 sequences, has a file size of 129 Kbytes, and is incorporated by reference in its entirety into the specification.

TECHNICAL FIELD

Described herein are diagnostic and control fusion protein reagents and methods for use thereof in simple rapid and inexpensive hemagglutinin assays for the detection of subject antibodies directed to the SARS-CoV-2 virus.

BACKGROUND

The COVID19 pandemic caused by SARS-CoV-2 approaches its first anniversary with close to one million deaths worldwide. At this point, countermeasures are largely restricted to symptomatic therapeutic interventions and prophylactic social distancing. Without a clear timeline for the availability of better therapeutic options and just starting vaccination efforts, it is clear that proper pandemic management hinges on the availability of diagnostic tests, including those revealing the presence of the virus itself to identify infectious carriers as well as those detecting antibody responses to assess the kinetics of the pandemic and the susceptibility of individual patients and the population at large. The latter aspect will also be relevant for evaluation and guidance of large-scale vaccination efforts.

Proper management of the pandemic caused by SARS-CoV-2 (COVID19) depends on laboratory tests that reliably detect (i) active virus, to identify virus carriers and (ii) SARS-CoV-2-specific antibodies, to identify individuals who were previously exposed to SARS-CoV-2, are at risk for infection or have successfully been vaccinated.

As investigated in detail in a comparative meta-analysis study, a significant (and growing) number of antibody tests are currently available, including various ELISAs (enzyme-linked immunosorbent assay) and related technologies, such as ECLIA (electrochemiluminescence immunoassay), FMIA (fluorescent microsphere Immunoassay), CMIA (chemiluminescent microparticle immunoassay) and ELFA (enzyme-linked fluorescent assay) [1]. Most of these tests exhibit appropriate specificity and sensitivity and are suitable for high throughput format in diagnostic laboratories [1]. Disadvantages include their restriction to special equipment and professional laboratories, relatively high costs and long turn-around times from sample acquisition to results. An alternative technology is the lateral flow immuno-assay (LVIA), which in principle can be conducted with minimal laboratory equipment. However, as also analyzed directly in referenced study, LFIAs typically exhibit appropriate specificity but restricted sensitivity, usually below 80%, and are relatively expensive (~$18 per test) [1].

While small, short-term studies indicated that antibody responses in asymptomatic patients may wean after weeks, at least two large scale studies have now demonstrated that antibody levels in symptomatic patients against the Spike protein and the Nucleocapsid (N) protein (NP) remain sustained at relatively high levels for at least 4-6 months [2]. These studies suggest that assessment of SARS-CoV-2-specific antibodies represents a proper tool for epidemiological studies and, likely, at least intermediate-term protection of convalescent patients. While studies so far are based on tests using the Spike or Nucleocapsid proteins as antigens, a recent study using luciferase-immunoprecipitation highlighted additional immunogenic proteins of SARS-CoV-2, in particular a small protein encoded by the open reading frame (ORF) 8 (ORF8), a known pathogenicity factor [3].

What is needed are simple, rapid, and inexpensive field tests for the detection of SARS-CoV-2-specific antibodies.

SUMMARY

One embodiment described herein is a nucleotide sequence encoding a polypeptide, wherein the polypeptide comprises a human red blood cell binding antibody domain (RBD) and a SARS CoV-2 virus protein domain (CVD). In one aspect, the RBD comprises a glycophorin A-binding nanobody comprising 90-99% identity to SEQ ID NO: 22. In another aspect, the CVD comprises one or more of a spike protein, a nucleocapsid protein, ORF8 protein, ORF3b protein, or envelope protein comprising 90-99% identity to all or a portion of SEQ ID NO: 24, 26, 28, or 30. In another aspect, the polypeptide has the structure: SS-GAP-RBD-GL2-CVD-GL3-AFT or SS-GL1-RBD-GL2-CVD-GL3-CVD-GL4-AFT, wherein: SS is a secretion signal domain; RBD is a glycophorin A-binding nanobody domain; GAP, GL1, GL2, GL3, and GL4 are linker domains; CVD is a SARS CoV-2 virus polypeptide domain comprising a spike protein, nucleocapsid protein, ORF8 protein, ORF3b protein, or envelope protein domains; and AFT is an affinity purification tag sequence. In another aspect, the SS comprises 90-99% identity to SEQ ID NO: 20. In another aspect, the GAP, GL1, GL2, GL3, or GL4 comprises 90-99% identity to one or more of SEQ ID NO: 38, 40, 42, 44, or 46. In another aspect, the AFT comprises 90-99% identity to one or more of SEQ ID NO: 58, 60, 62, or 64. In another aspect, the nucleotide sequence has 90% to 99% identity to SEQ ID NO: 1, 3, 5, 7, 9, or 11. In another aspect, the nucleotide sequence is one of SEQ ID NO: 1, 3, 5, 7, 9, or 11.

Another embodiment described herein is a polynucleotide vector comprising a nucleotide sequence described herein.

Another embodiment described herein is a cell comprising a polynucleotide vector comprising a nucleotide sequence described herein.

Another embodiment described herein is a polypeptide encoded by a nucleotide sequence described herein.

Another embodiment described herein is a polypeptide encoded by a nucleotide sequence described herein, wherein the polypeptide has 90% to 99% identity to SEQ ID NO: 2, 4, 6, 8, 10, or 12.

Another embodiment described herein is a polypeptide encoded by a nucleotide sequence described herein, wherein the polypeptide is SEQ ID NO: 2, 4, 6, 8, 10, or 12.

Another embodiment described herein is a diagnostic reagent or research tool comprising a polypeptide encoded by the nucleotide sequence described herein.

Another embodiment described herein is a method or means for manufacturing a nucleotide sequence as described herein or a polypeptide encoded by the nucleotide sequence, the process comprising: transforming or transfecting a cell with a nucleic acid comprising the nucleotide sequence; growing the cells; optionally, harvesting the cells and isolating quantities of the nucleotide sequence; inducing expression of a polypeptide encoded by the nucleotide sequence; harvesting the cells; and isolating and purifying the polypeptide.

Another embodiment described herein is a nucleotide sequence or a polypeptide encoded by the nucleotide sequence, each produced by a method or means described herein.

Another embodiment described herein is a nucleotide sequence encoding a diagnostic control polypeptide, wherein the polypeptide comprises: (a) a glycophorin A-binding nanobody domain comprising 90-99% identity to SEQ ID NO: 22; (b) one or more anti-SARS Co-V-2 nanobody domains comprising 90-99% identity to SEQ ID NO: 32 and one or more multimerization domains comprising 90-99% identity to SEQ ID NO: 34 o4 36. In one aspect, the polypeptides have the structure: SS-GAP-RBD-GL5-AFT, SS-GAP-anti-CVD-GL6-anti-CVD-GL7-IgGFC-GL8-AFT, or SS-GAP-anti-CVD-GL6-anti-CVD-SGT-HIZD-GL8-AFT; wherein: SS is a secretion signal domain; RBD is a glycophorin A-binding nanobody domain; GAP, GL5, GL6, GL7, GL8, and SGT are linker domains; Anti-CVD is an anti-SARS CoV-2 surface glycoprotein receptor binding domain nanobody domain; IgGFC is a human immunoglobulin FC dimerization domain; HIZD is a Hinge-isoleucine zipper trimerization domain; and AFT is an affinity purification tag sequence. In another aspect, the SS comprises 90-99% identity to SEQ ID NO: 20. In another aspect, the GAP, SGT, GL5, GL6, GL7, or GL8 comprises 90-99% identity to one or more of SEQ ID NO: 38, 48, 50, 52, 54, or 56. In another aspect, the AFT comprises 90-99% identity to one or more of SEQ ID NO: 58, 60, 62, or 64. In another aspect, the nucleotide sequence has 90% to 99% identity to SEQ ID NO: 13, 15, or 17. In another aspect, the nucleotide sequence is one of SEQ ID NO: 13, 15, or 17.

Another embodiment described herein is a polynucleotide vector comprising a nucleotide sequence encoding a diagnostic control polypeptide as described herein.

Another embodiment described herein is a cell comprising a polynucleotide vector comprising a nucleotide sequence encoding a diagnostic control polypeptide as described herein.

Another embodiment described herein is a diagnostic control polypeptide as described herein.

Another embodiment described herein is a diagnostic control polypeptide having 90% to 99% identity to SEQ ID NO: 14, 16, or 18.

Another embodiment described herein is a diagnostic control polypeptide having the polypeptide sequence of SEQ ID NO: 14, 16, or 18.

Another embodiment described herein is a diagnostic reagent or research tool comprising a polypeptide encoded by a nucleotide sequence described herein.

Another embodiment described herein is a diagnostic or control polypeptide comprising the amino acid sequence of SEQ ID NO: 2, 4, 6, 8, 10, 12, 14, 16, or 18.

Another embodiment described herein is a method for evaluating whether a subject is infected or has been infected with SARS-CoV-2, the method comprising: (a) providing a sample of a biological fluid from a subject in need of diagnosis; (b) combining the biological fluid with a diagnostic polypeptide comprising 90 to 99% identity to the amino acid sequence of SEQ ID NO: 2, 4, 6, 8, 10, 12 to form a subject sample; (c) optionally, combining a negative control reagent or a positive control polypeptide comprising 90 to 95% identity to the amino acid sequence of SEQ ID NO: 14 (negative control) or SEQ ID NO: 16 or 18 (positive controls), with the biological fluid and a diagnostic polypeptide comprising 90 to 99% identity to the amino acid sequence of SEQ ID NO: 2, 10, or 12 to form one or more control samples; (d) permitting the subject sample and control samples to incubate for a period of time; (e) evaluating the results by visualization, imaging, optical density, impedance, or microscopy; and (f) optionally, comparing the subject sample and control samples to validate the subject sample results; wherein the presence of hemagglutination in the subject sample is a positive diagnostic indication of SARS-CoV-2 infection, and the absence of hemagglutination in the subject sample is a negative diagnostic indication of SARS-CoV-2 infection. In one aspect, the biological fluid is whole blood, plasma, or serum. In another aspect, when the biological fluid is plasma or serum, washed human red blood cells of blood group O are combined with the subject sample and the diagnostic or control polypeptides in steps (b) or (c). In another aspect, wherein the diagnostic or control polypeptides have a concentration of about 10 μg/mL to about 100 μg/mL. In another aspect, the subject sample and/or control samples in steps (b) and/or (c) are dispensed on a test card, glass slide, microtiter plate, or other substrate prior to step (d). In another aspect, when the subject sample has a positive diagnostic indication of SARS-CoV-2 infection, the method further comprises: (g) administering one or more therapeutics or treatments to the subject.

Another embodiment described herein is a kit comprising: (a) one or more diagnostic or control polypeptides comprising the amino acid sequence of SEQ ID NO: 2, 4, 6, 8, 10, 12, 14, 16, or 18; (b) a test substrate; and (c) optionally, a label or instructions for use. In one aspect, the kit further comprises one or more of alcohol saturated towelettes; finger prick lances, capillaries, or gloves.

Another embodiment described herein is the use of a polypeptide comprising 90 to 99% identity to the amino acid sequence of SEQ ID NO: 2, 4, 6, 8, 10, 12, 14, 16, or 18 for the diagnosis of SARS-CoV-2 in a subject in need of diagnosis thereof.

Figure 1:
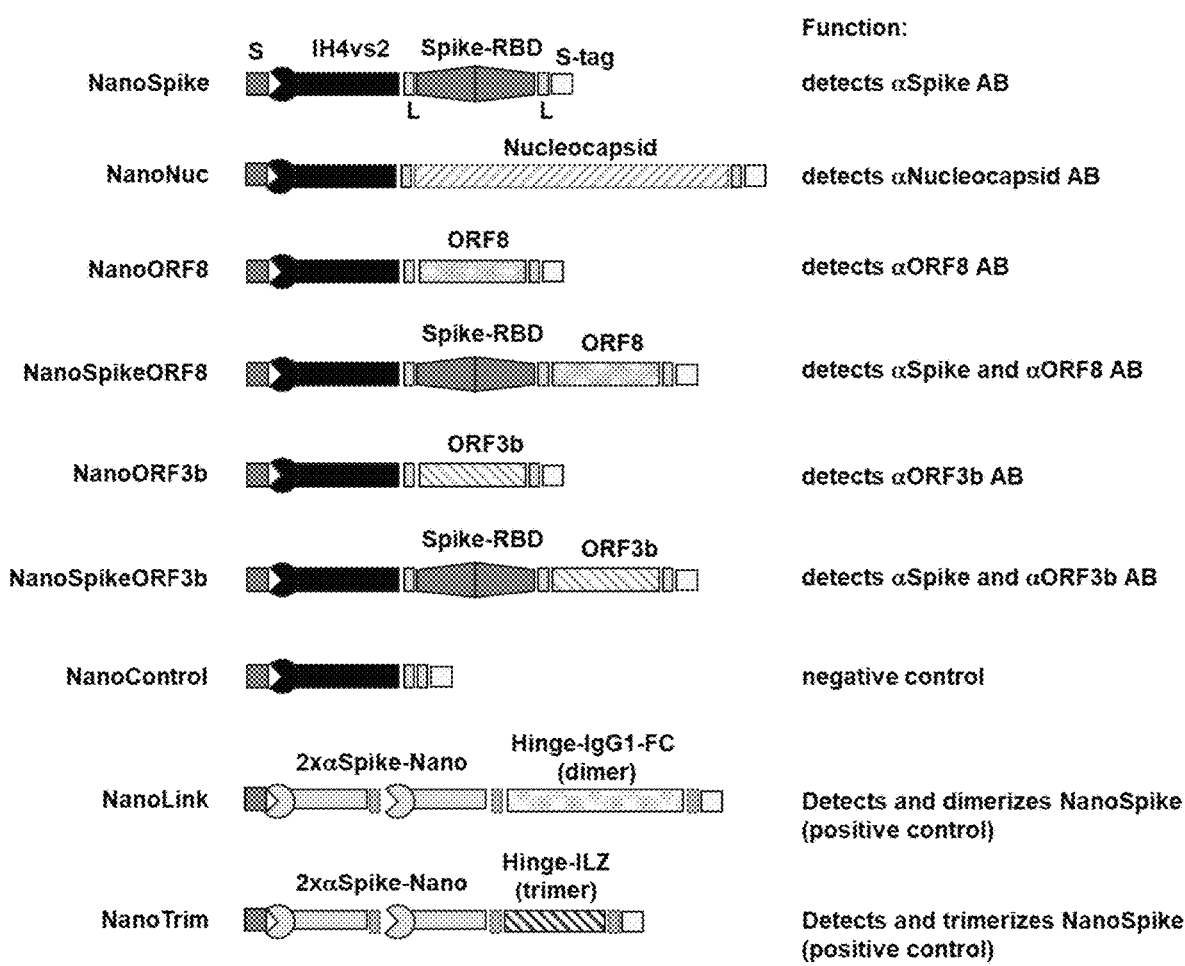
FIG. 1 shows schematic representations of the diagnostic and control fusion protein constructs. Key: S, secretion signal (IFNβ); IH4vs2, GPA-specific nanobody IH4vs2, which is efficiently secreted from mammalian cells (as opposed to the original IH4 nanobody); L, flexible linker; Spike, Spike-RBD of SARS-CoV-2; S-tag, Tandem-Strep-tag mediating binding to StrepTactin® matrix (IBA) for affinity purification; Nucleocapsid, Nucleocapsid protein of SARS-CoV-2, ORF8, ORF8 of SARS-CoV-2, ORF3b, ORF3b of SARS-CoV-2; 2×αSpike-Nano, tandem-fusion construct of two Spike-RBD-binding H11-D4 nanobodies, separated by flexible linker, Hinge-IgG1-FC, dimerizing Hinge-FC moiety of IgG1, Hinge-ILZ, trimerizing hinge-isoleucin-zipper domain. Polypeptide sequences are shown in Table 1.
Figure 2:
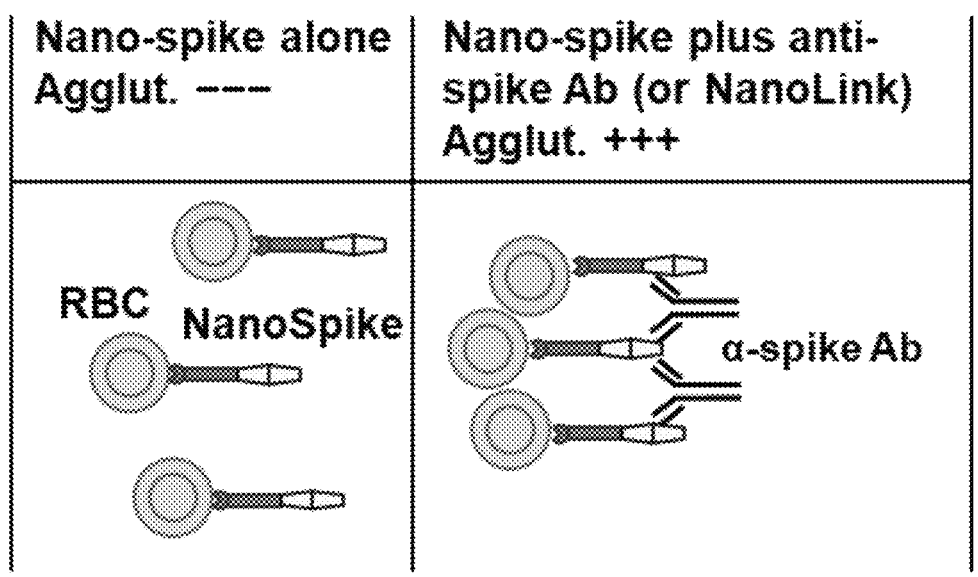
FIG. 2 shows the principle of Nano-spike-mediated hemagglutination in the presence of virus-specific (e.g., Spike-specific) antibodies (or the positive control nanobody, such as NanoLink).

As used herein a subject is "in need of diagnosis" if such subject would benefit biologically, medically, or in quality of life from such diagnosis. In one embodiment a subject needs diagnosis of SARS-CoV-2. In one aspect the subject may be presenting symptoms of SARS-CoV-2, may have been exposed to another individual presenting symptoms of SARS-CoV-2, may be a "carrier" of SARS-CoV-2 (without clinical presentation or symptoms), or may have previously been infected with SARS-CoV-2 and is in need of confirmation of such infection.

As used herein, the terms "inhibit," "inhibition," or "inhibiting" refer to the reduction or suppression of a given biological process, condition, symptom, disorder, or disease, or a significant decrease in the baseline activity of a biological activity or process.

As used herein, "treatment" or "treating" refers to prophylaxis of, preventing, suppressing, repressing, reversing, alleviating, ameliorating, or inhibiting the progress of biological process including a disorder or disease, or completely eliminating a disease. A treatment may be either performed in an acute or chronic way. The term "treatment" also refers to reducing the severity of a disease or symptoms associated with such disease prior to affliction with the disease. "Repressing" or "ameliorating" a disease, disorder, or the symptoms thereof involves administering a cell, composition, or compound described herein to a subject after clinical appearance of such disease, disorder, or its symptoms. "Prophylaxis of" or "preventing" a disease, disorder, or the symptoms thereof involves administering a cell, composition, or compound described herein to a subject prior to onset of the disease, disorder, or the symptoms thereof. "Suppressing" a disease or disorder involves administering a cell, composition, or compound described herein to a subject after induction of the disease or disorder thereof but before its clinical appearance or symptoms thereof have manifest. In one embodiment, after diagnosis of a subject being infected with SARS-CoV-2, a variety of treatments may be administered to target the virus, ameliorate symptoms, or provide palliative care.

Coronaviruses (CoVs), are enveloped positive-sense RNA viruses, which are surrounded by crown-shaped, club-like spikes projection on the outer surface. Coronaviruses' spike proteins are glycoproteins that are embedded over the viral envelope. This spike protein attaches to specific cellular receptors and initiates structural changes of spike protein, and causes penetration of cell membranes, which results in the release of the viral nucleocapsid into the cell. These spike proteins determine host trophism. Coronaviruses have a large RNA genome, ranging in size from 26 to 32 kilobases and capable of obtaining distinct ways of replication. Like other RNA viruses, coronaviruses under-go replication of the genome and transcription of mRNAs upon infection. Coronavirus infection in a subject can result in significant and long-term damage of the lungs, leading to possibly sever respiratory issues.

As used herein "SARS-CoV-2" is a beta-coronavirus (Beta-CoV or β-CoV). In particular, SARS-CoV-2 is a Beta-CoV of lineage B. SARS-CoV-2 may also be known as "2019-nCoV" or 2019 novel coronavirus. The disease associated with SARS-CoV-2 is known as COVID-19. Beta-coronaviruses are one of four genera of coronaviruses and are enveloped, positive-sense, single-stranded RNA viruses of zoonotic origin. Beta-coronaviruses mainly infect bats, but they also infect other species like humans, camels, and rabbits. SARS-CoV-2 may be transferable between animals, such as between humans. As used herein "viral transmission" is the process by which viruses spread between host subjects. Transmission occurs from person to person by direct or indirect contact or exposure. Examples of direct contact include, but are not limited to, the exchange of body fluids between a subject infected with the virus and someone else. Indirect contact includes, but is not limited to, exposure to bodily fluid droplets produced by a subject infected by the virus during coughing and/or sneezing. Beta-CoVs may induce fever and respiratory symptoms in humans. The SARS-CoV-2 receptor binding domain (RBD) of the spike protein binds to the human angiotensin-converting enzyme 2 (ACE2) receptor as a means for entering cells.

Diagnosis of SARS-CoV-2 may comprise a positive test for SARS-CoV-2 virus, viral RNA, subject antibodies against SARS-CoV-2 antigens, and/or onset of SARS-CoV-2 symptoms, or combinations thereof. The reagents and method described herein permit the diagnosis of infection of SARS-CoV-2 by reacting with antibodies produced by the subject in response to the SARS-CoV-2 infection. Symptoms of SARS-CoV-2 infection (COVID-19) include, but are not limited to, one or more of the following symptoms: nasal congestion, sore throat, fever, body aches, exhaustion, dry cough, difficulty breathing, or a combination thereof. Subjects at higher risk of developing complications may be immunocompromised (e.g., undergoing cancer treatment, bone marrow or organ transplantation, immune deficiencies, poorly controlled HIV or AIDS, prolonged use of corticosteroids or immune weakening medications), have an underlying medical condition (e.g., diabetes, renal failure, liver disease), are pregnant, are at least 65 years of age, have a chronic lung disease, have a heart disease, or combinations thereof.

Given the urgent need for evaluation of SARS-CoV-2-specific antibodies in a population for individual patients and the currently available tests with noted limitations, there is a significant need for rapid, simple, and affordable antibody tests with appropriate specificity and sensitivity. Such tests will allow decentralized testing of patients for SARS-CoV-2-specific antibodies, thus facilitating epidemiological management and vaccination efforts required to manage this pandemic effectively. Described herein is an assay based on (a) recombinant protein(s) that trigger(s) visible hemagglutination instantly in the presence of SARS-CoV-2 antibodies. The data provided herein establish proof of principle for this method.

The methods described herein are based on one or more recombinant fusion proteins containing at least three domains, i.e., a small camelid-derived antibody (nanobody) that binds to Glycophorin A (GYPA) on the surface of red blood cells (RBC) with high affinity, a SARS-CoV-2-specific immunogenic protein, such as the surface glycoprotein receptor "Spike" protein that serves as antigen for Corona-virus-directed antibodies, and an epitope-tag that is used for protein purification. The polypeptides also have an INF-β secretion sequence at the N-terminus to permit secretion from the expression cells. One embodiment described herein is the "NanoSpike," (SEQ ID NO: 2) which refers to the respective nanobody and SARS-CoV-2 surface glycoprotein receptor "Spike" domains of the fusion protein (FIG. 1; Table 1). As described herein NanoSpike can efficiently be expressed in various mammalian cell lines and binds to the glycophorin protein on the surface of human red blood cells. Importantly, when added to whole blood containing SARS-CoV-2-specific antibodies of subjects infected with or convalescing from SARS-CoV-2, NanoSpike triggers instant hemagglutination that is easily detected by visual observation or other means such as optical density, impedance, microscopy, imaging, or applications developed for this purpose. Other embodiments useful in the assay include "NanoNuc" (SEQ ID NO: 4), "NanoORF8" (SEQ ID NO: 6), "NanoSpikeORF8" (SEQ ID NO: 8), "NanoORF3b" (SEQ ID NO: 10), and "NanoSpikeORF3b" (SEQ ID NO: 12), which refer to the nanobody and SARS-CoV-2 nucleocapsid, ORF 8, surface glycoprotein receptor binding domain and ORF 8, ORF 3b, and ORF 3b and surface glycoprotein receptor binding domains, respectively. Each of these fusion proteins permits the detection of subject antibodies against these various SARS-CoV-2 antigens. Polypeptide sequences of these constructs are shown in Table 1. The complete SARS-CoV-2 genome is disclosed in SEQ ID NO: 65 (GenBank: MT072688.1). Other SARS-CoV-2 viral polypeptides are potentially useful for alternative embodiments of the diagnostic or control polypeptides described herein.

Also described herein are fusion proteins that can serve as negative or positive controls for the method or assay described herein. In one embodiment, the fusion protein "NanoControl" (SEQ ID NO: 14) can be used as a negative control. NanoControl comprises the Glycophorin A nanobody domain, but no COVID domain. This polypeptide will not react with SARS-CoV-2-specific antibodies of subjects infected with or convalescing from SARS-CoV-2 when added to a sample of the subject's blood. This construct serves as a negative control.

Alternatively, the "NanoLink" (SEQ ID NO: 16) and "NanoTrim" (SEQ ID NO: 18) fusion proteins can be used as positive controls for the method or assay described herein. NanoLink and NanoTrim fusion proteins both contain two repeated SARS-CoV-2-specific nanobody (H11-D4) domains that recognize the receptor binding domain of SARS-CoV-2 spike protein [4]. NanoLink also contains a hinge region of an IgG FC domain (from the Etanercept sequence) which permits dimerization. Similarly, the NanoTrim fusion protein contains a hinge-isoleucine zipper domain which permits trimerization [5]. These control polypeptides also have an INF-6 secretion sequence at the N-terminus to permit secretion from the expression cells.

The nanobody region of the NanoLink (SEQ ID NO: 16) and NanoTrim (SEQ ID NO: 18) constructs binds to the SARS-CoV-2 surface glycoprotein receptor biding domain (RBD) of the NanoSpike construct (or the NanoSpikeORF8 or NanoSpikeORF3b constructs, each of which contains the SARS-CoV-2 spike proteins RBD domain) and can cause hemagglutination (in the absence of a subject's anti-SARS-CoV-2 antibodies) and permits a side-by-side comparison of the assay results with assays conducted with NanoNuc (SEQ ID NO: 4), NanoORF8 (SEQ ID NO: 6), NanoSpikeORF8 (SEQ ID NO: 8), NanoORF3b (SEQ ID NO: 10), NanoSpikeORF3b and NanoControl (as a negative control). Collectively, these constructs permit across-validated assay that can be used to assess the presence of anti-SARS-CoV-2 antibodies in a subject's blood.

Polypeptide sequences of the NanoSpike, NanoNuc NanoORF8, NanoSpikeORF8, NanoORF3b, NanoSpikeORF3b, NanoControl, NanoLink, and NanoTrim constructs are shown in Table 1. Nucleic acid sequences are provided in the sequence listing (odd SEQ ID NOs of the even number polypeptide SEQ ID NOs).

TABLE 1

Polypeptide Constructs

NanoSpike (SEQ ID NO: 1-2)
*MTNKCLLQLALLLCFSTTALSM*GAPQVQLQESGGGSVQAGGSLRLSCVASGYTDSTYCVGWFRQAPGKEREGVARI
NTISGRPWYADSVKGRFTISQDNSKNTVYLQMNSLKPEDTAIYYCTLTTANSRGFCSGGYNYKGQGTQVTVSGGTS
GGGGSGGGGSGGGGSAAARFPNITNLCPFGEVFNATRFASVYAWNRKRISNCVADYSVLYNSASFSTFKCYGVSPT
KLNDLCFTNVYADSFVIRGDEVRQIAPGQTGKIADYNYKLPDDFTGCVIAWNSNNLDSKVGGNYNYLYRLFRKSNL
KPFERDISTEIYQAGSTPCNGVEGFNCYFPLQSYGFQPTNGVGYQPYRVVVLSFELLHAPATVCGPKKSTNLEFGG
GSGGGSGGGSAWSHPQFEKGGGSGGGSGGSAWSHPQFEK

*INF-β Secretion Sequence*: Residues 1-22
Linkers: Residues 23-25; 149-170; 377-390
RBC Binding Domain: 26-148
COVID Spike Domain: 171-376
Dual Strep Tag: 391-419

NanoNuc (SEQ ID NO: 3-4)
*MTNKCLLQLALLLCFSTTALSM*GAPQVQLQESGGGSVQAGGSLRLSCVASGYTDSTYCVGWFRQAPGKEREGVARI
NTISGRPWYADSVKGRFTISQDNSKNTVYLQMNSLKPEDTAIYYCTLTTANSRGFCSGGYNYKGQGTQVTVSGGTS
GGGGSGGGGSGGGGSAAAMSDNGPQNQRNAPRITFGGPSDSTGSNQNGERSGARSKQRRPQGLPNNTASWFTALTQ
HGKEDLKFPRGQGVPINTNSSPDDQIGYYRRATRRIRGGDGKMKDLSPRWYFYYLGTGPEAGLPYGANKDGIIWVA
TEGALNTPKDHIGTRNPANNAAIVLQLPQGTTLPKGFYAEGSRGGSQASSRSSSRSRNSSRNSTPGSSRGTSPARM
AGNGGDAALALLLLDRLNQLESKMSGKGQQQQGQTVTKKSAAEASKKPRQKRTATKAYNVTQAFGRRGPEQTQGNF
GDQELIRQGTDYKHWPQIAQFAPSASAFFGMSRIGMEVTPSGTWLTYTGAIKLDDKDPNFKDQVILLNKHIDAYKT
FPPTEPKKDKKKADETQALPQRQKKQTVTLLPAADLDDFSKQLQQSMSSADSTQAEFGGGSGGGSGGGSAWSHP

QFEKGGGSGGGSGGSAWSHPQFEK

*INF-β Secretion Sequence*: Residues 1-22
Linkers: Residues 23-25; 149-170; 590-603
RBC Binding Domain: 26-148
COVID Nucleocapsid Domain: 171-589
Dual Strep Tag: 604-632

NanoORF8 (SEQ ID NO: 5-6)
*MTNKCLLQIALLLCFSTTALSM*GAPQVQLQESGGGSVQAGGSLRLSCVASGYTDSTYCVGWFRQAPGKEREGVARI
NTISGRPWYADSVKGRFTISQDNSKNTVYLQMNSLKPEDTAIYYCTLTTANSRGFCSGGYNYKGQGTQVTVSGGTS TABLE 1-continued Polypeptide Constructs GGGGSGGGGSGGGGSAAAQECSLQSCTQHQPYVVDDPCPIHFYSKWYIRVGARKSAPLIELCVDEAGSKSPIQYID
IGNYTVSCLPFTINCQEPKLGSLVVRCSFYEDFLEYHDVRVVLDF<u>IPRGGGSGGGSGGGSAWSHPQFEKGGGSGGG</u>
<u>SGGGSAWSHPQFEK</u>

*INF-β Secretion Sequence*: Residues 1-22
Linkers: Residues 23-25; 149-170; 274-288
RBC Binding Domain: 26-148
COVID ORF 8 Domain: 171-273
Dual Strep Tag: 289-317

NanoSpikeORF8 (SEQ ID NO: 7-8)
*MTNKCLLQIALLLCFSTTALSM*<u>GAP</u>QVQLQESGGGSVQAGGSLRLSCVASGYTDSTYCVGWFRQAPGKEREGVARI
NTISGRPWYADSVKGRFTISQDNSKNTVYLQMNSLKPEDTAIYYCTLTTANSRGFCSGGYNYKGQGTQVTVS<u>GGTS</u>
<u>GGGGSGGGGSGGGGSAAA</u>RFPNITNLCPFGEVFNATRFASVYAWNRKRISNCVADYSVLYNSASFSTFKCYGVSPT
KLNDLCFTNVYADSFVIRGDEVRQIAPGQTGKIADYNYKLPDDFTGCVIAWNSNNLDSKVGGNYNYLRLFRKSNL
KPFERDISTEIYQAGSTPCNGVEGFNCYFPLQSYGFQPTNGVGYQPYRVVVLSFELLHAPATVCGPKKSTNL<u>EFSG</u>
<u>GGGSGGGGSGGGGSAAA</u>QECSLQSCTQHQPYVVDDPCPIHFYSKWYIRVGARKSAPLIELCVDEAGSKSPIQYID
IGNYTVSCLPFTINCQEPKLGSLVVRCSFYEDFLEYHDVRVVLDF<u>IPRGGGSGGGSGGGSAWSHPQFEKGGGSGGGS</u>
<u>GGSAWSHPQFEK</u>

*INF-β Secretion Sequence*: Residues 1-22
Linkers: Residues 23-25; 149-170; 377-397; 501-515
RBC Binding Domain: 26-148
COVID Spike Domain: 171-376
COVID ORF 8 Domain: 398-500

Dual Strep Tag: 516-544

NanoORF3b (SEQ ID NO: 9-10)
*MTNKCLLQIALLLCFSTTALSM*<u>GAP</u>QVQLQESGGGSVQAGGSLRLSCVASGYTDSTYCVGWFRQAPGKEREGVARI
NTISGRPWYADSVKGRFTISQDNSKNTVYLQMNSLKPEDTAIYYCTLTTANSRGFCSGGYNYKGQGTQVTVS<u>GGTS</u>
<u>GGGGSGGGGSGGGGSAAA</u>MAYCWRCTSCCFSERFQNHNPQKEMATSTLQGCSLCLQLAVVVNSLLTPFARCC<u>WPEF</u>
<u>GGGSGGGGSGGGSAWSHPQFEKGGGSGGGSGGSAWSHPQFEK</u>

*INF-β Secretion Sequence*: Residues 1-22
Linkers: Residues 23-25; 149-170; 227-240
RBC Binding Domain: 26-148
COVID ORF 3b Domain: 171-226
Dual Strep Tag: 241-269

NanoSpikeORF3b (SEQ ID NO: 11-12)
*MTNKCLLQIALLLCFSTTALSM*<u>GAP</u>QVQLQESGGGSVQAGGSLRLSCVASGYTDSTYCVGWFRQAPGKEREGVARI
NTISGRPWYADSVKGRFTISQDNSKNTVYLQMNSLKPEDTAIYYCTLTTANSRGFCSGGYNYKGQGTQVTVS<u>GGTS</u>
<u>GGGGSGGGGSGGGGSAAA</u>RFPNITNLCPFGEVFNATRFASVYAWNRKRISNCVADYSVLYNSASFSTFKCYGVSPT
KLNDLCFTNVYADSFVIRGDEVRQIAPGQTGKIADYNYKLPDDFTGCVIAWNSNNLDSKVGGNYNYLRLFRKSNL
KPFERDISTEIYQAGSTPCNGVEGFNCYFPLQSYGFQPTNGVGYQPYRVVVLSFELLHAPATVCGPKKSTNL<u>EFSG</u>
<u>GGGSGGGGSGGGGSAAA</u>MAYCWRCTSCCFSERFQNHNPQKEMATSTLQGCSLCLQLAVVVNSLLTPFARCCW<u>EFG</u>
<u>GGSGGGSGGGSAWSHPQFEKGGGSGGGSGGSAWSHPQFEK</u>

*INF-β Secretion Sequence*: Residues 1-22
Linkers: Residues 23-25; 149-170; 377-397; 454-467
RBC Binding Domain: 26-148
COVID Spike Domain: 171-376
COVID ORF 3b Domain: 398-453

Dual Strep Tag: 467-496

NanoControl (SEQ ID NO: 13-14)
*MTNKCLLQIALLLCFSTTALSM*<u>GAP</u>QVQLQESGGGSVQAGGSLRLSCVASGYTDSTYCVGWFRQAPGKEREGVARI
NTISGRPWYADSVKGRFTISQDNSKNTVYLQMNSLKPEDTAIYYCTLTTANSRGFCSGGYNYKGQGTQVTVS<u>GEFG</u>
<u>GGSGGGSGGGSAWSHPQFEKGGGSGGGSGGSAWSHPQFEK</u>

*INF-β Secretion Sequence*: Residues 1-22
Linkers: Residues 23-25; 149-163
RBC Binding Domain: 26-148
Dual Strep Tag: 164-192

NanoLink (SEQ ID NO: 16)
*MTNKCLLQIALLLCFSTTALSM*<u>GAP</u>QVQLVESGGGLMQAGGSLRLSCAVSGRTFSTAAMGWFRQAPGKEREFVAAI
RWSGGSAYYADSVKGRFTISRDKAKNTVYLQMNSLKYEDTAVYYCARTENVRSLLSDYATWPYDYWGQGTQVTVSG
<u>GGGSGGGGSGGGGS</u>IDQVQLVESGGGLMQAGGSLRLSCAVSGRTFSTAAMGWFRQAPGKEREFVAAIRWSGGSAYY
ADSVKGRFTISRDKAKNTVYLQMNSLKYEDTAVYYCARTENVRSLLSDYATWPYDYWGQGTQVTVSSGTGGGSGG
<u>GGSGGGGSGS</u>EPKSCDKTHTCPPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRWQQGNVFSCSVMHEALH

TABLE 1-continued

Polypeptide Constructs

NHYTQKSLSLSPGK<u>PRGGGSGGGSGGGSAAAWSHPQFEKGGGSGGGSGGGSWSHPQFEK</u>

*INF-β Secretion Sequence*: Residues 1-22
Linkers: Residues 23-25; 152-168; 295-314; 547-562
SARS-CoV-2 Spike RBD specific nanobody (H11-D4): 26-151; 169-294
IgG-FC Dimerization domain: 315-546
Dual Strep Tag: 563-591

NanoTrim (SEQ ID NO: 17-18)
*MTNKCLLQLALLLCFSTTALSM*GAPQVQLVESGGGLMQAGGSLRLSCAVSGRTFSTAAMGWFRQAPGKEREFVAAI
RWSGGSAYYADSVKGRFTISRDKAKNTVYLQMNSLKYEDTAVYYCARTENVRSLLSDYATWPYDYWGQGTQVTVSG
GGGSGGGGSGGGGSIDQVQLVESGGGLMQAGGSLRLSCAVSGRTFSTAAMGWFRQAPGKEREFVAAIRWSGGSAYY
ADSVKGRFTISRDKAKNTVYLQMNSLKYEDTAVYYCARTENVRSLLSDYATWPYDYWGQGTQVTVS<u>SGT</u>⬚⬚⬚⬚⬚⬚⬚
⬚⬚⬚⬚⬚⬚⬚⬚⬚⬚⬚⬚⬚⬚⬚⬚⬚⬚⬚⬚⬚⬚⬚⬚⬚⬚⬚⬚⬚⬚⬚⬚⬚⬚⬚⬚⬚⬚⬚⬚⬚⬚⬚⬚⬚⬚<u>PRGGGSGGGSGGGSAAAWSHP</u>
<u>QFEKGGGSGGGSGGGSWSHPQFEK</u>

*INF-β Secretion Sequence*: Residues 1-22
Linkers: Residues 23-25; 152-168; 295-297; 360-375
SARS-CoV-2 Spike RBD specific nanobody (H11-D4): 26-151; 169-294
Hinge-isoleucine zipper domain (trimerization domain): 298-359
Dual Strep Tag: 376-404

Odd number SEQ ID NO are nucleotide sequences; event numbers are polypeptide sequences The fusion proteins listed in Table 1 can be expressed in mammalian cells and particularly in human cell lines. In one embodiment the proteins are expressed in human embryonic kidney 293 cells (HEK 293). In another aspect, the proteins are expressed in Expi293F™ Cells (Thermo Fisher Scientific). The proteins are secreted into the media and are purified using affinity chromatography. In one aspect, the proteins are purified using Strep-Tactin®X (IBA) resin or beads on a column or batch format. The purified proteins were desalted and concentrated. Further polishing steps can be performed using ion exchange, gel filtration, or other chromatographic methods known in the art.

The diagnostic assays described herein require a minimal amount of whole blood (e.g., from a finger prick). Alternatively, subject plasma or serum can be used when combined with human red blood cells (e.g., from the subject or washed human red blood cells of blood group O). A small amount of blood (e.g., 10-20 μL is typically combined with the test or control solutions (concentration of NanoSpike or other constructs: 20-60 μg/mL) at a ratio of ~1:1 in an appropriate vessel (microfuge tub) or directly on a test card; gently mixed; and the reaction mixture is spread over the test card field (~1 cm² diameter). The test card is rotated manually or with a mechanical rotor at 80-100 rpm for up to about 2-5 minutes and immediately read under direct light. The presence of hemagglutination (aggregation of red blood cells) is a positive result that indicates the presence of subject antibodies against SARS-CoV-2 antigens (e.g., surface glycoprotein, nucleocapsid, ORF8, OR3b, or a combination thereof).

The assay method described herein was validated using 40 COVID19-positive subjects (and 42 control subjects), with 98% sensitivity and 98% specificity. This assay enables simple, rapid, sensitive, specific, and inexpensive diagnosis and identification of subjects with SARS-CoV-2-specific antibodies, either as result of previous infection or successful vaccination. Information provided by this test is be valuable for epidemiological surveillance and decisions related to forthcoming vaccination efforts.

One embodiment described herein is a nucleotide sequence encoding a polypeptide, wherein the polypeptide comprises a human red blood cell binding antibody domain (RBD) and a SARS CoV-2 virus protein domain (CVD). In one aspect, the RBD comprises a glycophorin A-binding nanobody comprising 90-99% identity to SEQ ID NO: 22. In another aspect, the CVD comprises one or more of a spike protein, a nucleocapsid protein, ORF8 protein, ORF3b protein, or envelope protein comprising 90-99% identity to all or a portion of SEQ ID NO: 24, 26, 28, or 30.

In one aspect, the polypeptide has the structure:

SS-GAP-RBD-GL2-CVD-GL3-AFT or

SS-GL1-RBD-GL2-CVD-GL3-CVD-GL4-AFT;

wherein:
SS is a secretion signal domain;
RBD is a glycophorin A-binding nanobody domain;
GAP, GL1, GL2, GL3, and GL4 are linker domains;
CVD is a SARS CoV-2 virus polypeptide domain comprising a spike protein, nucleocapsid protein, ORF8 protein, ORF3b protein, or envelope protein domains; and
AFT is an affinity purification tag sequence.

In another aspect, the SS comprises 90-99% identity to SEQ ID NO: 20. In another aspect, the GAP, GL1, GL2, GL3, or GL4 comprises 90-99% identity to one or more of SEQ ID NO: 38, 40, 42, 44, or 46. In another aspect, the AFT comprises 90-99% identity to one or more of SEQ ID NO: 58, 60, 62, or 64. In another aspect, the nucleotide sequence has 90% to 99% identity to SEQ ID NO: 1, 3, 5, 7, 9, or 11. In another aspect, the nucleotide sequence is one of SEQ ID NO: 1, 3, 5, 7, 9, or 11.

Another embodiment described herein is a polynucleotide vector comprising a nucleotide sequence described herein.

Another embodiment described herein is a cell comprising a polynucleotide vector comprising a nucleotide sequence described herein.

Another embodiment described herein is a polypeptide encoded by a nucleotide sequence described herein.

Another embodiment described herein is a polypeptide encoded by a nucleotide sequence described herein, wherein the polypeptide has 90% to 99% identity to SEQ ID NO: 2, 4, 6, 8, 10, or 12.

Another embodiment described herein is a polypeptide encoded by a nucleotide sequence described herein, wherein the polypeptide is SEQ ID NO: 2, 4, 6, 8, 10, or 12.

Another embodiment described herein is a diagnostic reagent or research tool comprising a polypeptide encoded by the nucleotide sequence described herein.

Another embodiment described herein is a method or means for manufacturing a nucleotide sequence as described herein or a polypeptide encoded by the nucleotide sequence, the process comprising: transforming or transfecting a cell with a nucleic acid comprising the nucleotide sequence; growing the cells; optionally, harvesting the cells and isolating quantities of the nucleotide sequence; inducing expression of a polypeptide encoded by the nucleotide sequence; harvesting the cells; and isolating and purifying the polypeptide.

Another embodiment described herein is a nucleotide sequence or a polypeptide encoded by the nucleotide sequence, each produced by a method or means described herein.

Another embodiment described herein is a nucleotide sequence encoding a diagnostic control polypeptide, wherein the polypeptide comprises: (a) a glycophorin A-binding nanobody domain comprising 90-99% identity to SEQ ID NO: 22; (b) one or more anti-SARS Co-V-2 nanobody domains comprising 90-99% identity to SEQ ID NO: 32 and one or more multimerization domains comprising 90-99% identity to SEQ ID NO: 34 o4 36.

In one aspect, the polypeptides have the structure:

SS-GAP-RBD-GL5-AFT;

SS-GAP-anti-CVD-GL6-anti-CVD-GL7-IgGFC-GL8-AFT; or

SS-GAP-anti-CVD-GL6-anti-CVD-SGT-HIZD-GL8-AFT;

wherein:

SS is a secretion signal domain;

RBD is a glycophorin A-binding nanobody domain;

GAP, GL5, GL6, GL7, GL8, and SGT are linker domains;

Anti-CVD is an anti-SARS CoV-2 surface glycoprotein receptor binding domain nanobody domain;

IgGFC is a human immunoglobulin FC dimerization domain;

HIZD is a Hinge-isoleucine zipper trimerization domain; and

AFT is an affinity purification tag sequence.

In another aspect, the SS comprises 90-99% identity to SEQ ID NO: 20. In another aspect, the GAP, SGT, GL5, GL6, GL7, or GL8 comprises 90-99% identity to one or more of SEQ ID NO: 38, 48, 50, 52, 54, or 56. In another aspect, the AFT comprises 90-99% identity to one or more of SEQ ID NO: 58, 60, 62, or 64. In another aspect, the nucleotide sequence has 90% to 99% identity to SEQ ID NO: 13, 15, or 17. In another aspect, the nucleotide sequence is one of SEQ ID NO: 13, 15, or 17.

Another embodiment described herein is a polynucleotide vector comprising a nucleotide sequence encoding a diagnostic control polypeptide as described herein.

Another embodiment described herein is a cell comprising a polynucleotide vector comprising a nucleotide sequence encoding a diagnostic control polypeptide as described herein.

Another embodiment described herein is a diagnostic control polypeptide as described herein.

Another embodiment described herein is a diagnostic control polypeptide having 90% to 99% identity to SEQ ID NO: 14, 16, or 18.

Another embodiment described herein is a diagnostic control polypeptide having the polypeptide sequence of SEQ ID NO: 14, 16, or 18.

Another embodiment described herein is a diagnostic reagent or research tool comprising a polypeptide encoded by a nucleotide sequence described herein.

Another embodiment described herein is a diagnostic or control polypeptide comprising the amino acid sequence of SEQ ID NO: 2, 4, 6, 8, 10, 12, 14, 16, or 18.

Another embodiment described herein is a method for evaluating whether a subject is infected or has been infected with SARS-CoV-2, the method comprising: (a) providing a sample of a biological fluid from a subject in need of diagnosis; (b) combining the biological fluid with a diagnostic polypeptide comprising 90 to 99% identity to the amino acid sequence of SEQ ID NO: 2, 4, 6, 8, 10, 12 to form a subject sample; (c) optionally, combining a negative control reagent or a positive control polypeptide comprising 90 to 95% identity to the amino acid sequence of SEQ ID NO: 14 (negative control) or SEQ ID NO: 16 or 18 (positive controls), with the biological fluid and a diagnostic polypeptide comprising 90 to 99% identity to the amino acid sequence of SEQ ID NO: 2, 10, or 12 to form one or more control samples; (d) permitting the subject sample and control samples to incubate for a period of time; (e) evaluating the results by visualization, imaging, optical density, impedance, or microscopy; and (f) optionally, comparing the subject sample and control samples to validate the subject sample results; wherein the presence of hemagglutination in the subject sample is a positive diagnostic indication of SARS-CoV-2 infection, and the absence of hemagglutination in the subject sample is a negative diagnostic indication of SARS-CoV-2 infection. In one aspect, the biological fluid is whole blood, plasma, or serum. In another aspect, when the biological fluid is plasma or serum, washed human red blood cells of blood group O are combined with the subject sample and the diagnostic or control polypeptides in steps (b) or (c). In another aspect, wherein the diagnostic or control polypeptides have a concentration of about 10 μg/mL to about 100 μg/mL. In another aspect, the subject sample and/or control samples in steps (b) and/or (c) are dispensed on a test card, glass slide, microtiter plate, or other substrate prior to step (d). In another aspect, when the subject sample has a positive diagnostic indication of SARS-CoV-2 infection, the method further comprises: (g) administering one or more therapeutics or treatments to the subject.

Another embodiment described herein is a kit comprising: (a) one or more diagnostic or control polypeptides comprising the amino acid sequence of SEQ ID NO: 2, 4, 6, 8, 10, 12, 14, 16, or 18; (b) a test substrate; and (c) optionally, a label or instructions for use. In one aspect, the kit further comprises one or more of alcohol saturated towelettes; finger prick lances, capillaries, or gloves.

Another embodiment described herein is the use of a polypeptide comprising 90 to 99% identity to the amino acid sequence of SEQ ID NO: 2, 4, 6, 8, 10, 12, 14, 16, or 18 for the diagnosis of SARS-CoV-2 in a subject in need of diagnosis thereof.

Another embodiment described herein is a polynucleotide vector comprising one or more nucleotide sequences described herein. In one aspect, the nucleotide sequence comprises 85% to 100% identity to SEQ ID NO: 1, 3, 5, 7, 9, 11, 13, 15, or 17 and encodes a polypeptide having 85% to 100% identity to SEQ ID NO: 2, 4, 6, 8, 10, 12, 14, 16, or 18.

Another embodiment described herein is a cell comprising one or more nucleotide sequences described herein or a polynucleotide vector described herein encoding one or more polypeptides. In one aspect, the nucleotide sequence has 85% to 100% identity to SEQ ID NO: 1, 3, 5, 7, 9, 11, 13, 15, or 17 and the encoded polypeptide has 85% to 100% identity to SEQ ID NO: 2, 4, 6, 8, 10, 12, 14, 16, or 18.

Another embodiment is a diagnostic or control polypeptide encoded by a nucleotide sequence described herein. In one aspect, the nucleotide sequence has 85% to 100% identity to SEQ ID NO: 1, 3, 5, 7, 9, 11, 13, 15, or 17 and the encoded polypeptide has 85% to 100% identity to SEQ ID NO: 2, 4, 6, 8, 10, 12, 14, 16, or 18. In another aspect, the diagnostic polypeptide is selected from SEQ ID NO: 2, 4, 6, 8, 10, or 12. In another aspect the control polypeptide is selected from SEQ ID NO: 14, 16, or 18

Another embodiment described herein is a process for manufacturing one or more of the nucleotide sequence described herein or a polypeptide encoded by the nucleotide sequence described herein, the process comprising: transforming or transfecting a cell with a nucleic acid comprising a nucleotide sequence described herein; growing the cells; optionally isolating additional quantities of a nucleotide sequence described herein; inducing expression of a polypeptide encoded by a nucleotide sequence of described herein; isolating the polypeptide encoded by a nucleotide described herein.

Another embodiment described herein is a means for manufacturing one or more of the nucleotide sequences described herein or a polypeptide encoded by the nucleotide sequence described herein, the process comprising: transforming or transfecting a cell with a nucleic acid comprising a nucleotide sequence described herein; growing the cells; optionally isolating additional quantities of a nucleotide sequence described herein; inducing expression of a polypeptide encoded by a nucleotide sequence of described herein; isolating the polypeptide encoded by a nucleotide described herein.

Another embodiment described herein is a nucleotide sequence or a polypeptide encoded by the nucleotide sequence produced by the method or the means described herein Another embodiment described herein is the use of an effective amount of a polypeptide encoded by one or more of the nucleotide sequences described herein having 85% to 100% identity to SEQ ID NO: 1, 3, 5, 7, 9, 11, 13, 15, 17.

Another embodiment described herein is a research tool comprising a polypeptide encoded by a nucleotide sequence described herein.

Another embodiment described herein is an analytical reagent comprising a polypeptide encoded by a nucleotide sequence described herein.

The polynucleotides described herein include variants that have substitutions, deletions, and/or additions that can involve one or more nucleotides. The variants can be altered in coding regions, non-coding regions, or both. Alterations in the coding regions can produce conservative or non-conservative amino acid substitutions, deletions, or additions. Especially preferred among these are silent substitutions, additions, and deletions, which do not alter the properties and activities of the binding.

Further embodiments described herein include nucleic acid molecules comprising polynucleotides having nucleotide sequences about 50%, 55%, 60%, 65%, 70%, 75%, 80%, 85%, 90%, 91%, 92%, 93%, 94%, 95%, 96%, 97%, 98%, or 99% identical, and more preferably at least about 90-99% or 100% identical to (a) nucleotide sequences, or degenerate, homologous, or codon-optimized variants thereof, encoding polypeptides having the amino acid sequences in SEQ ID NO: 2, 4, 6, 8, 10, 12, 14, 16, or 18 (b) nucleotide sequences, or degenerate, homologous, or codon-optimized variants thereof, encoding polypeptides having the amino acid sequences in SEQ ID NO: 2, 4, 6, 8, 10, 12, 14, 16, or 18; and (c) nucleotide sequences capable of hybridizing to the complement of any of the nucleotide sequences in (a) or (b) above and capable of expressing functional polypeptides of amino acid sequences in SEQ ID NO: 2, 4, 6, 8, 10, 12, 14, 16, or 18.

By a polynucleotide having a nucleotide sequence at least, for example, 90-99% "identical" to a reference nucleotide sequence encoding a polypeptide of SEQ ID NO: 2, 4, 6, 8, 10, 12, 14, 16, or 18 is intended that the nucleotide sequence encoding the polynucleotide be identical to the reference sequence except that the polynucleotide sequence can include up to about 10 to 1 point mutations, additions, or deletions per each 100 nucleotides of the reference nucleotide sequence encoding a polypeptide of SEQ ID NO: 2, 4, 6, 8, 10, 12, 14, 16, or 18.

In other words, to obtain a polynucleotide having a nucleotide sequence about at least 90-99% identical to a reference nucleotide sequence, up to 10% of the nucleotides in the reference sequence can be deleted, added, or substituted, with another nucleotide, or a number of nucleotides up to 10% of the total nucleotides in the reference sequence can be inserted into the reference sequence. These mutations of the reference sequence can occur at the 5'- or 3'-terminal positions of the reference nucleotide sequence or anywhere between those terminal positions, interspersed either individually among nucleotides in the reference sequence or in one or more contiguous groups within the reference sequence. The same is applicable to polypeptide sequences about at least 90-99% identical to a reference polypeptide sequence.

As noted above, two or more polynucleotide sequences can be compared by determining their percent identity. Two or more amino acid sequences likewise can be compared by determining their percent identity. The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, *Advances in Applied Mathematics* 2: 4 82-489 (1981). This algorithm can be extended to use with peptide sequences using the scoring matrix developed by Dayhoff, *Atlas of Protein Sequences and Structure*, M. O. Dayhoff ed., 5 suppl. 3: 353-358, National Biomedical Research Foundation, Washington, D.C., USA, and normalized by Gribskov, *Nucl. Acids Res.* 14(6): 6745-6763 (1986).

For example, due to the degeneracy of the genetic code, one having ordinary skill in the art will recognize that a large number of the nucleic acid molecules having a sequence at least 50%, 55%, 60%, 65%, 70%, 75%, 80%, 85%, 90%, 91%, 92%, 93%, 94%, 95%, 96%, 97%, 98%, 99%, or 100% identical to the nucleic acid sequence shown in SEQ ID NO: 1, 3, 5, 7, 9, 11, 13, 15, or 17, or degenerate, homologous, or codon-optimized variants thereof, will encode a polypeptide having a sequence at least 50%, 55%, 60%, 65%, 70%, 75%, 80%, 85%, 90%, 91%, 92%, 93%, 94%, 95%, 96%, 97%, 98%, 99%, or 100% identical to the polypeptide sequence shown in SEQ ID NO: 2, 4, 6, 8, 10, 12, 14, 16, or 18.

The polynucleotides described herein include those encoding mutations, variations, substitutions, additions, deletions, and particular examples of the polypeptides described herein. For example, guidance concerning how to make phenotypically silent amino acid substitutions is provided in Bowie, J. U. et al., "Deciphering the Message in Protein Sequences: Tolerance to Amino Acid Substitutions," *Science* 247: 1306-1310 (1990), wherein the authors indicate that proteins are surprisingly tolerant of amino acid substitutions.

Thus, fragments, derivatives, or analogs of the polypeptides of SEQ ID NO: 2, 4, 6, 8, 10, 12, 14, 16, or 18 can be (i) ones in which one or more of the amino acid residues (e.g., 1, 2, 3, 4, 5, 7, 8, 9, 10, 11, 12, 13, 14, 15, 16, 17, 18, 19, 20, 25, 30, 35, 40, 45, or 50 residues, or even more) are substituted with a conserved or non-conserved amino acid residue (preferably a conserved amino acid residue). Such substituted amino acid residues may or may not be one encoded by the genetic code, or (ii) ones in which one or more of the amino acid residues includes a substituent group (e.g., 1, 2, 3, 4, 5, 7, 8, 9, 10, 15, 20, 25, 30, 35, 40, 45, or 50 residues or even more), or (iii) ones in which the mature polypeptide is fused with another polypeptide or compound, such as a compound to increase the half-life of the polypeptide (for example, polyethylene glycol), or (iv) ones in which the additional amino acids are fused to the mature polypeptide, such as an IgG Fc fusion region peptide or leader or secretory sequence or a sequence which is employed for purification of the mature polypeptide or a proprotein sequence. Such fragments, derivatives, and analogs are deemed to be within the scope of those skilled in the art from the teachings herein.

In addition, fragments, derivatives, or analogs of the polypeptides of SEQ ID NO: 2, 4, 6, 8, 10, 12, 14, 16, or 18 can be substituted with one or more conserved or non-conserved amino acid residue (preferably a conserved amino acid residue). In some cases these polypeptides, fragments, derivatives, or analogs thereof will have a polypeptide sequence at least 50%, 55%, 60%, 65%, 70%, 75%, 80%, 85%, 90%, 91%, 92%, 93%, 94%, 95%, 96%, 97%, 98%, 99% or 100% identical to the polypeptide sequence shown in SEQ ID NO: 2, 4, 6, 8, 10, 12, 14, 16, or 18 and will comprise functional or non-functional proteins or enzymes. Similarly, additions or deletions to the polypeptides can be made either at the N- or C-termini or within non-conserved regions of the polypeptide (which are assumed to be non-critical because they have not been photogenically conserved).

As described herein, in many cases the amino acid substitutions, mutations, additions, or deletions are preferably of a minor nature, such as conservative amino acid substitutions that do not significantly affect the folding or activity of the protein or additions or deletions to the N- or C-termini. Of course, the number of amino acid substitutions, additions, or deletions as killed artisan would make depends on many factors, including those described herein. Generally, the number of substitutions, additions, or deletions for any given polypeptide will not be more than about 100, 90, 80, 70, 60, 50, 40, 30, 25, 20, 19, 18, 17, 16, 15, 14, 13, 12, 11, 10, 9, 8, 7, 5, 6, 4, 3, 2, or 1.

It will be apparent to one of ordinary skill in the relevant art that suitable modifications aid adaptations to the compositions, formulations, methods, processes, apparata, assemblies, and applications described herein can be made without departing from the scope of any embodiments or aspects thereof. The compositions, apparata, assemblies, and methods provided are exemplary and are not intended to limit the scope of any of the disclosed embodiments. All the various embodiments, aspects, and options disclosed herein can be combined in any variations or iterations. The scope of the compositions, formulations, methods, apparata, assemblies, and processes described herein include all actual or potential combinations of embodiments, aspects, options, examples, and preferences described herein. The compositions, formulations, apparata, assemblies, or methods described herein may omit any component or step, substitute any component or step disclosed herein, or include any component or step disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. All patents and publications cited herein are incorporated by reference herein for the specific teachings thereof.

REFERENCES

1. Kontou et al., "Antibody Tests in Detecting SARS-CoV-2 Infection: A Meta-Analysis," *Diagnostics* (Basel) 10(5): 319 (2020).
2. Gudbjartsson et al., "Humoral Immune Response to SARS-CoV-2 in Iceland," *N. Engl. J. Med.* 383(18):1724-1734 (2020).
3. Hachim et al., "ORF8 and ORF3b antibodies are accurate serological markers of early and late SARS-CoV-2 infection," *Nat. Immunol.* 21(10):1293-1301 (2020).
4. Huo et al., "Neutralizing nanobodies bind SARS-CoV-2 spike RBD and block interaction with ACE2," *Nat. Struct. Mol. Biol.* 27(9): 846-854 (2020).
5. Tillib et al., "Formatted single-domain antibodies can protect mice against infection with influenza virus (H5N2)," *Antiviral Res.* 97(3):245-254 (2013).
6. Redecke et al., "Hematopoietic progenitor cell lines with myeloid and lymphoid potential," *Nat. Methods* 10(8): 795-803 (2013).
7. Lee et al., "Production of specific antibodies against SARS-coronavirus nucleocapsid protein without cross reactivity with human coronaviruses 229E and OC43," *J. Vet. Sci.* 11(2): 165-167 (2010).
8. Lee et al., "Detection of antibodies against SARS-Coronavirus using recombinant truncated nucleocapsid proteins by ELISA," *J. Microbiol. Biotechnol.* 18(10): 1717-1721 (2008).
9. Dutta et al., "Search for potential target site of nucleocapsid gene for the design of an epitope-based SARS DNA vaccine," *Immunol. Let.* 118(1): 65-71 (2008).
10. Gupta and Chaudhary, "Whole-blood agglutination assay for on-site detection of human immunodeficiency virus infection," *J. Clin. Microbiol.* 41(7): 2814-2821 (2003).
11. Kemp et al., "Autologous red cell agglutination assay for HIV-1 antibodies: simplified test with whole blood," *Science* 241(4871):1352-1354 (1988).
12. Gupta and Chaudhary, "Expression, purification, and characterization of an anti-RBCFab-p24 fusion protein for hemagglutination-based rapid detection of antibodies to HIV in whole blood," *Protein Expr. Purif.* 26(1): 162-170 (2002).
13. Habib et al., "V(H)H (nanobody) directed against human glycophorin A: a tool for autologous red cell agglutination assays," *Anal. Biochem.* 438(1): 82-89 (2013).
14. Tai et al., "Characterization of the receptor-binding domain (RBD) of 2019 novel coronavirus: implication for development of RBD protein as a viral attachment inhibitor and vaccine," *Cell. Mol. Immunol.* 17(6): 613-620 (2020).
15. Ravichandran et al., "Antibody signature induced by SARS-CoV-2 spike protein immunogens in rabbits," *Sci. Transl. Med.* 12(550): eabc3539 (2020).
16. Grzelak et al., "A comparison of four serological assays for detecting anti-SARS-CoV-2 antibodies in human serum samples from different populations," *Sci. Transl. Med.* 12(559): eabc3103 (2020).

EXAMPLES

Example 1

Plasmids

DNA encoding expressed proteins was synthesized by commercial suppliers (Thermo Fisher Scientific/Invitrogen, Synbio, Biomatic) and cloned by standard molecular biology methods into the mammalian expression vector pcDNA3.1(+) (Invitrogen). All coding sequences were confirmed by Sanger sequencing.

Protein Expression

All proteins were expressed in Expi293F™ cells (Thermo Fisher Scientific) using the ExpiFectamine™ 293 Transfection Kit following the manufacturer's instructions (Thermo Fisher Scientific). In brief, cells were cultured at 37° C. and 8% $CO_2$ in 25 mL of Expi293 expression medium (Thermo Fisher Scientific) in 125 mL bottles on a 25 mm orbital shaker (120 rpm) until reaching a density of $4.5-5.5\times10^6$/mL. Cells were seeded at $3\times10^6$/mL in 25 mL per 125 mL flasks for transfection. 25 µg of DNA and 80 µL of Epifectamine was added to 1.5 mL and 1.4 mL Opti-Plex complexation buffer (Thermo Fisher Scientific), respectively. After a 3-5 min incubation at room temperature (RT), the two solutions were combined, gently mixed, incubated for 15 min at RT and added dropwise to cells. After overnight culture, Epifectamine transfection enhancer 1 (150 µL) and Epifectamine transfection enhancer 2 (1.5 mL) was added, and cell suspensions were harvested two days later.

Protein Purification

Cell suspensions were centrifuged at 450 g for 5 min and protein-containing supernatant was cleared using 0.2 µm filter bottles. To remove biotin (interfering with affinity purification), 3 mL of 10× buffer W (1M Tris-HCl pH 8.0, 1.5 M NaCl, 10 mM EDTA) was added to the supernatant along with 600 µL of BioLock solution (IBA), followed by ultracentrifugation at 20,000×g for 20 min at 4° C. The resulting supernatant was loaded on columns containing 700 µL of washed Strep-Tactin® XT matrix (IBA). The columns were rinsed five times with 1 mL ice-cold PBS, proteins were eluted with 3×500 µL of buffer BXT (IBA), concentrated on Amicon Ultra3k concentration columns (3 kD cutoff) at 14,000×g at 4° C. and desalted by centrifugation at 1500×g for 2 min using TBS-equilibrated Zeba Spin desalting columns (0.5 mL, 7 k MWCO, Thermo Fisher Scientific). 3-10 µg of each purified proteins was analyzed by SDS PAGE and Sypro Ruby staining (Thermo Fisher Scientific).

Example 2

Design, Expression and Purification of Recombinant Proteins

Figure 3:
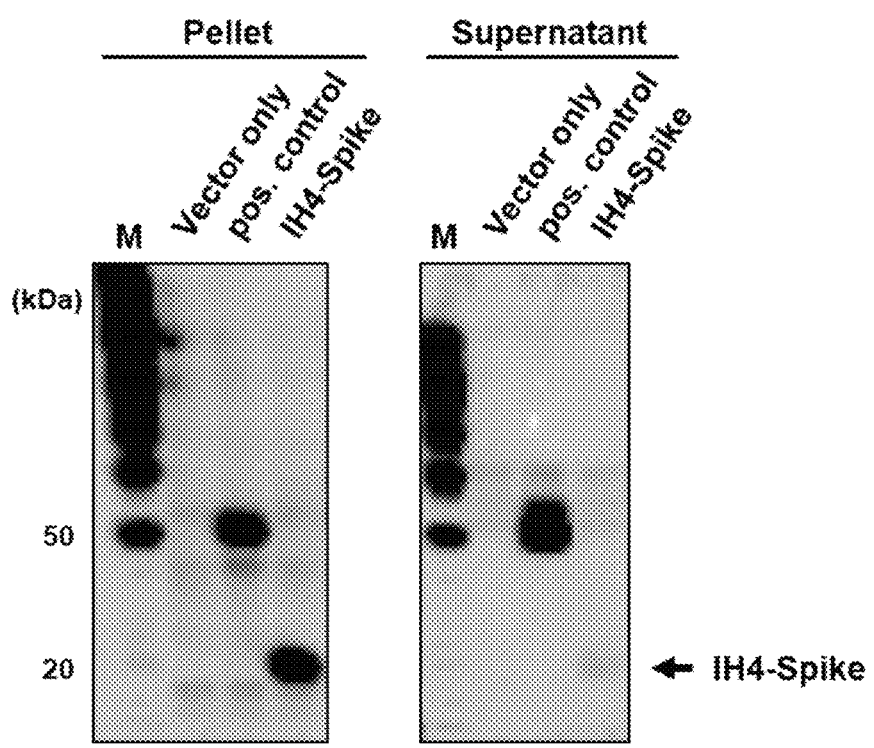
FIG. 3 shows a fusion protein of the IH4 nanobody and the Spike RBD is not efficiently secreted. A fusion construct of the IH4 nanobody (SEQ ID NO: 65-66) and the Spike-RBD (IH4-Spike) was transfected into HEK293T cells along with a negative (vector) control and a positive control construct, and protein expression was analyzed in the cell pellet and the supernatant. Note the almost complete lack or IH4-Spike in the supernatant. Vector only-transfected cells (vector only) and cells transfected with a secreted control protein (positive control) show expected results.
Figure 4:
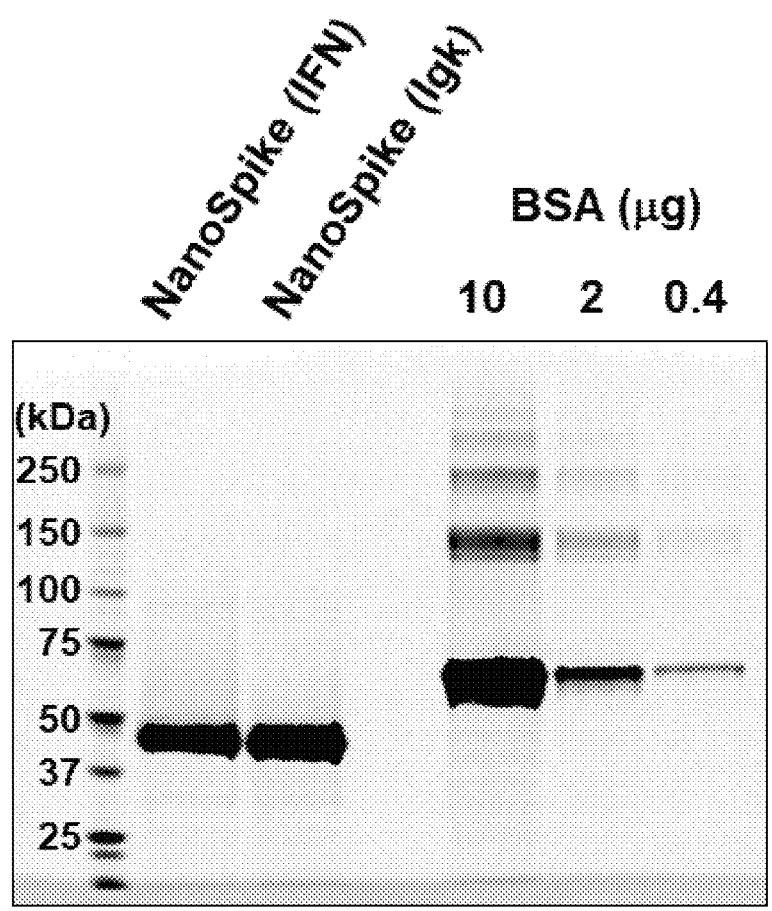
FIG. 4 shows two mutations in the IH4 nanobody permit efficient secretion of Spike-RBD fusion proteins. Fusion constructs with modified forms of IH4 (IH4vs2) (SEQ ID NO:21-22), i.e., IH4vs2-Spike (i.e., "NanoSpike"; SEQ ID NO:1-2) and a As used herein, a subject is "in need of treatment" if such subject would benefit biologically, medically, or in quality of life from such treatment. A subject in need of treatment does not necessarily present symptoms, particular in the case of preventative or prophylaxis treatments. In one aspect, the subject may need diagnosis of a condition prior to treatment. Embodiments described herein can be used to make or confirm such a diagnosis.
Figure 5:
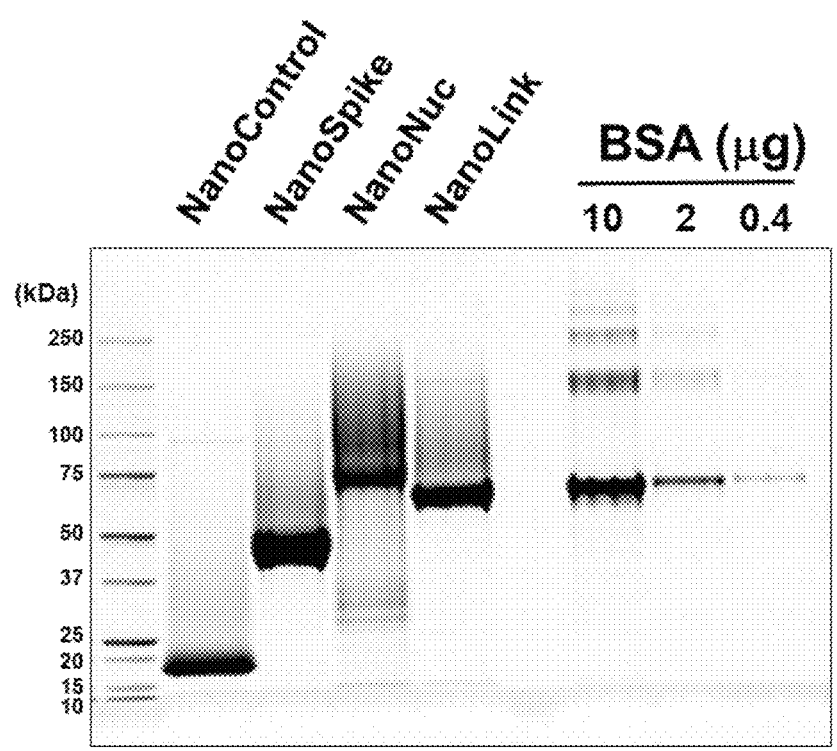

Due to the known robustness of nanobodies and the availability of required sequence information. Methodologically, a modified form of the IH4 nanobody (IH4vs2) was fused to the receptor-binding domain of the Spike protein of SARS-CoV-2, which has been shown in various analyses to represent a highly immunogenic region [6-8]. Mammalian cells were used for protein expression. The SARS Co-V-2 surface "spike" glycoprotein is physiologically targeted to the secretory pathway, which is likely required for proper protein folding and accompanied by glycosylation, which in turn may be relevant for the antibody response and thus test specificity [9]. To allow for proper targeting to the secretory pathway, a secretion signal derived from interferon-β was fused to the N-terminus of the fusion protein (FIG. 1). A tandem Strep-tag was fused to the C-terminus to allow for efficient one-step protein purification. Flexible glycine-serine-containing linkers were placed between the functional units of the fusion protein to avoid interference of the different domains. A similar protein lacking the Spike RBD was cloned as negative control (FIG. 1). The proteins were expressed first in small scale, then in larger scale experiments in either ExpiCho-S™ or Expi293F™ cells (Thermo Fisher Scientific), both of which are optimized for high density growth in suspension and used extensively in the pharmaceutical industry. As shown for experiments based on Expi293F™ cells, protein expression and Strep-tag-based one-step purification was very efficient, resulting in virtually homogenous protein preparations for both the NanoSpike and the NanoControl protein (FIG. 3-5). Around 2 mg of protein were obtained from 30 mL of cell culture, reflecting a highly efficient process.

Example 3

Functional Activity of Recombinant Proteins in Hemagglutination Assays

Figure 6:
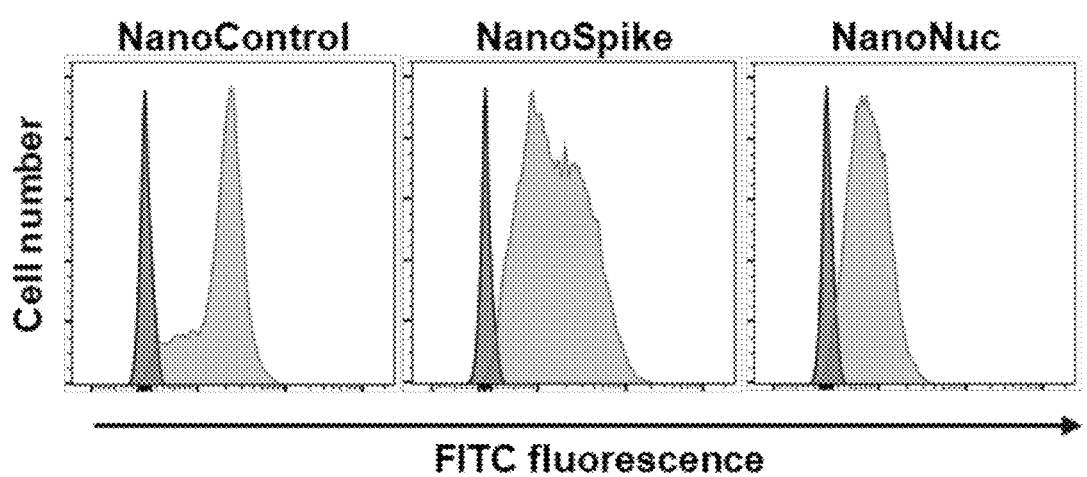
Figure 7:
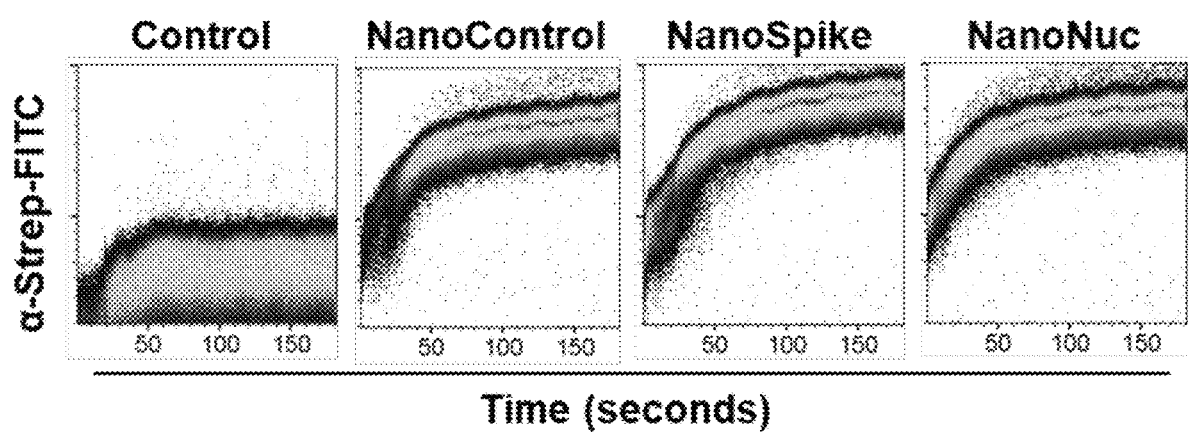

To determine whether the NanoSpike protein binds to red blood cells, different concentrations of the NanoSpike protein were incubated with human whole blood, followed by visualization using FITC-conjugated anti-Strep-tag antibodies and flow cytometry (FIG. 6-7). As expected, NanoSpike bound efficiently and in a concentration-dependent manner to RBC.

In order to determine if NanoSpike cross-linking induces visible hemagglutination of RBC, the NanoSpike protein was added to a small drop (10 µL) of human whole blood, either in the absence of antibodies, anti-Strep antibodies (crosslinking) or anti-CD4 antibodies (negative control). Indeed, in the presence of NanoSpike, anti-Strep antibodies induced instant hemagglutination in a concentration-dependent way. anti-Strep antibodies alone or anti-Strep antibodies in the presence of αCD4 antibodies showed no effect, demonstrating specificity. Given that the anti-Strep antibodies is a monoclonal IgG1 antibodies, these data also suggest that the valency of IgG is sufficient to trigger agglutination (as opposed to the higher valency of IgM).

To obtain proof of principle for NanoSpike activity in the presence of physiological αSpike antibodies, whole blood of a confirmed COVID19 patient was combined with Nano- Spike or NanoControl protein. Indeed, similar to the anti-Strep antibody-treated samples, NanoSpike mediated instant hemagglutination. NanoSpike expressed from ExpiCho-S and Expi293F cells showed the same activity. As the protein amount obtained from Expi293F cells was slightly higher, these cells were used for further expression. Of note, NanoControl protein did not exhibit any agglutination, even during extended periods of time, suggesting that agglutination is solely governed by the Spike RBD moiety, respectively antibodies directed against Spike. This experiment was confirmed with two patients two weeks after being tested PCR-positive (not shown).

Example 4

To further substantiate the initial testing described above, five plasma samples from COVID19 patients with ELISA-positive αSARS-CoV-2 antibody titers was tested, along with five confirmed antibody-negative control samples. Plasma was used for these assays because it was immediately available from frozen stocks maintained at a reference laboratory (ARUP). For these assays, washed RBC from a healthy donor were used and combined NanoSpike (or NanoControl) protein along with plasma from test samples. All COVID19-positive samples showed immediate hemagglutination in the presence of NanoSpike, but not the NanoControl protein, while all COVID19-negative samples remained without detectable hemagglutination. Even though blood plasma is not the intended major type of material typically used for the assay (i.e., the preferred sample is finger stick capillary blood), it has the advantage that it can be titrated independent of RBC and was useful to assess the sensitivity of the assay at different antibodies concentrations. This facilitated the testing and optimization of other viral proteins fused to the Nanobody (e.g., NanoNuc, NanoORF8, NanoORF3b, NanoSpikeORF8, NanoSpikeORF3b).

Example 5

Figure 8:
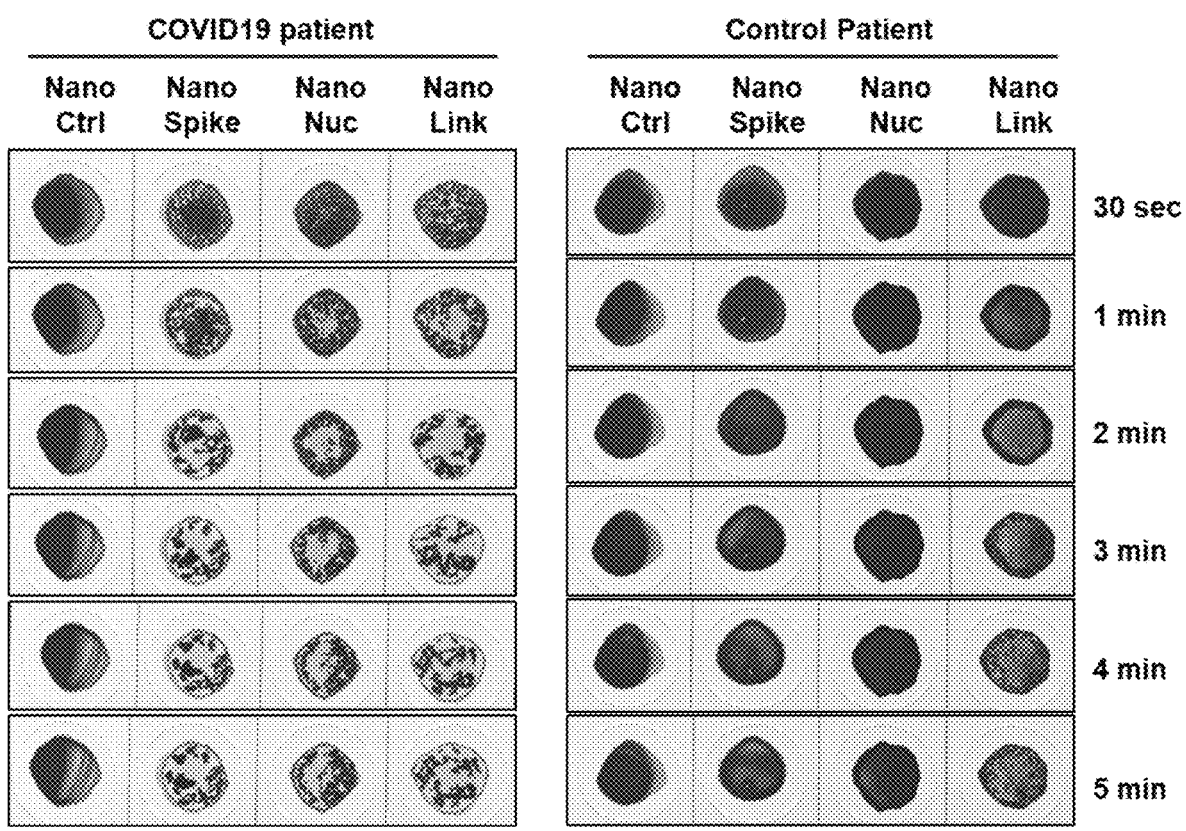

The assay was further validated using serum from patients which had been tested with an FDA-approved Spike-ELISA (Euroimmun). Forty ELISA-positive and forty-two ELISA-negative cases were enrolled. NanoControl, NanoSpike and NanoLink recombinant proteins (30 µg/mL) were added to washed RBC along with the subject serum and the presence or absence of hemagglutination was observed and documented (FIG. 8). The number of cases that were correctly identified by the NanoSpike test (in a blinded analysis) are shown in Table 2.

Based on these assays, specificity, and sensitivity were calculated according to standard formulas: Sensitivity=number of true test-positive divided by (number of true test-positive plus number of false negatives). Specificity=number of true test-negatives divided by (number of true test-negatives plus number of false positives).

TABLE 2

NanoSpike identifies sero-positive COVID19 patients with high specificity and sensitivity.

| | Euroimmune (Spike) ELISA (82 patients) | |
|---|---|---|
| ELISA (Number of cases) | 40 (test-positive) | 42 (test-negative) |
| NanoSpike Agglutination (number of correct identifications) | 39 | 41 |
| NanoSpike Agglutination (number of incorrect identifications) | 1 | 1 |
| Specificity (%) | 98 | |
| Sensitivity (%) | 98 | |

Example 6

NanoSpike Assay Methodology
Assay Reagents/Components:
Subject sample: blood, serum, plasma, or other biological fluid sample (described below)
NanoSpike, NanoNuc, NanoORF8, NanoORF3b, NanoSpikeORF8, NanoSpikeORF3b, or other Nanobody (IH4vs2)-conjugated proteins (20-60 µg/mL): glycophorin targeting nanobody conjugated to SARS-CoV-2 proteins
NanoControl (20-60 µg/mL): Negative control, glycophorin targeting nanobody alone
NanoLink (20-60 µg/mL): Positive control, test substance (20-60 µg/mL); SARS-CoV-2 Spike-targeting nanobody construct (based on the H11-D4 nanobody) fused to the Hinge-FC part of IgG1 protein. This compound mimics dimerizing anti-Spike antibodies.
NanoTrim (20-60 µg/mL): Positive control, test substance (20-60 µg/mL), SARS-CoV-2 Spike-targeting nanobody construct (based on the H11-D4 nanobody) fused to trimerizing Hinge-isoleucine zipper domain. This compound mimics multimerizing anti-Spike antibodies.
Miscellaneous Items: Test cards; gloves; alcohol (70% isopropanol) towelettes; finger prick lances; bandages; pipets, pipet tips, microfuge tubes, magnifying means, bright light; biohazard disposal receptacle; etc.
Specimen Collection
Total Blood
  Blood was collected in vacutainers or collection tubes containing EDTA by venipuncture or finger-stick.
Plasma
  Blood was collected in vacutainers containing EDTA by venipuncture and plasma was separated by centrifugation.
Serum
  Blood was collected in vacutainers containing no anticoagulants by venipuncture and plasma was separated by centrifugation after the blood had clotted.
Test Procedures (at room temperature, ~25° C.):
Total Blood
  A small amount of blood, e.g., 10-20 µL, was combined with test or control solutions at a ratio of ~1:1, gently mixed, and the reaction mixture was spread over the test card field (~1 cm² diameter).
  The test card was rotated manually or with a mechanical rotor at 80-100 rpm for 2-5 minutes and immediately read under direct light.
  The presence of hemagglutination was a positive result. The absence of hemagglutination was a negative result. Results were compared to positive and/or negative control samples using the same subject sample.
Plasma and Serum
  A small amount of plasma or serum, e.g. 5-10 µL, was combined with a small amount, e.g., 5-10 µL, of washed human red blood cells (RBC) of blood group O. RBCs can be used pure or diluted with PBS up to 1:10.

The test or control solutions are added to the plasma/serum/RBC mixture at a ratio of 1:1, gently mixed and the reaction mixture was spread over the test field (~1 cm² diameter).

The test card was rotated manually or with a mechanical rotor at 80-100 rpm for 2-5 minutes and immediately read under direct light.

The presence of hemagglutination was a positive result. The absence of hemagglutination was a negative result. Results were compared to positive and/or negative control samples using the same subject sample.

Hemagglutination can be visually read on cardboard test cards or on glass slides. Alternative assay systems include the use of microtiter plates, gel immunodiffusion, ouchterlony, or automated systems that can detect agglutination, e.g., by still or video imaging, optical density, impedance, microscopy, or using specific applications developed for this purpose.

Exemplary Cost Analysis

One advantage of the assays described herein is their simplicity and low costs. Based on regular prices (not wholesale), estimated material costs for protein expression and purification amount to ~$0.019/assay, and additional equipment (also regular retail prices), including lancets, capillaries, and ethanol wipes amount to ~$0.30/assay. While overhead costs for personnel aid logistics need to be accounted, it is expected that up-scaled protein production and wholesale prizes for equipment will further reduce production costs.

What is claimed:

1. A method for evaluating whether a subject is infected or has been infected with SARS-CoV-2, the method comprising:
(a) providing a sample of a biological fluid from a subject in need of diagnosis;
(b) combining the biological fluid with one or more diagnostic or control polypeptide comprising:
a diagnostic polypeptide comprising one or more of a polypeptide sequence of SEQ ID NO: 22 and one or more SARS COV-2 virus protein domains (CVD) selected from one or more of a spike protein, a nucleocapsid protein, an ORF8 protein, an ORF3b protein, or an envelope protein;
a control polypeptide comprising one or more of:
(i) a glycophorin A-binding nanobody domain comprising the polypeptide sequence of SEQ ID NO: 14; or
(ii) one or more anti-SARS Co-V-2 nanobody domains comprising a polypeptide sequence having at least 90-99% identity to SEQ ID NO: 32 and one or more multimerization domains comprising a polypeptide sequence having at least 90-99% identity to SEQ ID NO: 34 or 36;

(c) permitting the subject sample and control samples to incubate for a period of time;

(d) evaluating the results by visualization, imaging, optical density, impedance, or microscopy; and wherein the presence of hemagglutination in the subject sample is a positive diagnostic indication of SARS-CoV-2 infection, and the absence of hemagglutination in the subject sample is a negative diagnostic indication of SARS-CoV-2 infection.

2. The method of claim 1, wherein the CVD comprises a polypeptide having at least 90-99% identity to all or a portion of SEQ ID NO: 24, 26, 28, or 30.

3. The method of claim 1, wherein the polypeptide has the structure:

SS-GAP-RBD-GL2-CVD-GL3-AFT or

SS-GL1-RBD-GL2-CVD-GL3-CVD-GL4-AFT;

wherein:
SS is a secretion signal domain;
RBD is the glycophorin A-binding nanobody domain;
GAP, GL1, GL2, GL3, and GL4 are linker domains;

CVD is the SARS COV-2 virus polypeptide domain comprising a spike protein, a nucleocapsid protein, an ORF8 protein, an ORF3b protein, or an envelope protein domain; and AFT is an affinity purification tag sequence.

4. The method of claim 3, wherein the SS comprises a polypeptide sequence having at least 90-99% identity to SEQ ID NO: 20.

5. The method of claim 3, wherein the GAP, GL1, GL2, GL3, or GL4 comprises a polypeptide sequence having at least 90-99% identity to one or more of SEQ ID NO: 38, 40, 42, 44, or 46.

6. The method of claim 3, wherein the affinity purification tag (AFT) comprises a polypeptide sequence having at least 90-99% identity to one or more of SEQ ID NO: 58, 60, 62, or 64.

7. The method of claim 1, wherein the polypeptide has a polypeptide sequence having at least 90% to 99% identity to SEQ ID NO: 2, 4, 6, 8, 10, or 12.

8. The method of claim 1, wherein the diagnostic polypeptide has a polypeptide sequence selected from SEQ ID NO: 2, 4, 6, 8, 10, or 12.

9. The method of claim 1, wherein the diagnostic polypeptide is encoded by a nucleotide sequence having at least 90% to 99% identity to SEQ ID NO: 1, 3, 5, 7, 9, or 11.

10. The method of claim 1, wherein the diagnostic polypeptide is encoded by a nucleotide sequence of SEQ ID NO: 1, 3, 5, 7, 9, or 11.

11. The method of claim 1, wherein the control polypeptide is encoded by a nucleotide sequence having at least 90% to 99% identity to SEQ ID NO: 13, 15, or 17.

12. The method of claim 1, wherein the control polypeptide is encoded by a nucleotide sequence selected from SEQ ID NO: 13, 15, or 17.

13. The method of claim 1, wherein the control polypeptide has a polypeptide sequence of at least 90% to 99% identity to SEQ ID NO: 16 or 18.

14. The method of claim 1, wherein the control polypeptide has a polypeptide sequence selected from SEQ ID NO: 16 or 18.

15. The method of claim 1, wherein the biological fluid is whole blood, plasma, or serum.

16. The method of claim 15, wherein when the biological fluid is plasma or serum, washed human red blood cells of blood group O are combined with the subject sample and the diagnostic or control polypeptides in steps (b) or (c).

17. The method of claim 1, wherein the diagnostic or control polypeptides have a concentration of about 10 μg/mL to about 100 μg/mL.

18. The method of claim 1, wherein the subject sample in step (b) is dispensed on a test card, glass slide, microtiter plate, or other substrate prior to step (c).

19. The method of claim 1, wherein when the subject sample has a positive diagnostic indication of SARS-CoV-2 infection, the method further comprises:

administering one or more therapeutics or treatments to the subject.

* * * * *